United States Patent
Mueller et al.

(10) Patent No.: US 11,560,549 B2
(45) Date of Patent: Jan. 24, 2023

(54) INTEGRATION SITES IN CHO CELLS

(71) Applicant: Boehringer Ingelheim International GmbH, Ingelheim am Rhein (DE)

(72) Inventors: Markus Mueller, Ingelheim am Rhein (DE); Jochen Schaub, Ingelheim am Rhein (DE); Christian Bernloehr, Ingelheim am Rhein (DE); Jennifer Koenitzer, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 335 days.

(21) Appl. No.: 16/637,914

(22) PCT Filed: Aug. 10, 2018

(86) PCT No.: PCT/EP2018/071733
§ 371 (c)(1),
(2) Date: Feb. 10, 2020

(87) PCT Pub. No.: WO2019/030373
PCT Pub. Date: Feb. 14, 2019

(65) Prior Publication Data
US 2020/0216815 A1    Jul. 9, 2020

(30) Foreign Application Priority Data
Aug. 11, 2017 (EP) .................... 17185988

(51) Int. Cl.
*C12N 5/071* (2010.01)
*C12N 15/63* (2006.01)
*C12N 15/90* (2006.01)

(52) U.S. Cl.
CPC .......... *C12N 5/0682* (2013.01); *C12N 15/63* (2013.01); *C12N 15/907* (2013.01); *C12N 2310/20* (2017.05); *C12N 2510/02* (2013.01)

(58) Field of Classification Search
CPC ............... C07K 16/00; C07K 2319/81; C07K 2317/14; C12N 9/22; C12N 2310/20; C12N 2800/30; C12N 5/0682; C12N 15/907; C12N 2510/02; C12N 15/63
See application file for complete search history.

(56) References Cited

FOREIGN PATENT DOCUMENTS

| WO | 2000017337 A1 | 3/2000 |
| WO | 2014205192 A2 | 12/2014 |
| WO | 2016064999 A1 | 4/2016 |

OTHER PUBLICATIONS

Lattenmayer et al., "Identification of transgene integration loci of different highly expressing recombinant CHO cell lines by FISH", Cytotechnology, 51(3), pp. 171-182 (Nov. 15, 2006).
Notification of Transmittal of the International Search Report and Written Opinion of the International Searching Authority, or the Declaration, International Search Report and Written Opinion in International Application No. PCT/EP2018/071733, dated Sep. 19, 2018 (12 pages).
Seong Lee et al., "Site-specific integration in CHO cells mediated by CRISPR/Cas9 and homology-directed DNA repair pathway", Scientific Reports, 5(1), pp. 1-11 (Feb. 25, 2015).

*Primary Examiner* — Ganapathirama Raghu
(74) *Attorney, Agent, or Firm* — McNeill Baur PLLC

(57) ABSTRACT

The present invention relates to the identification of a genomic integration site for heterologous polynucleotides in Chinese Hamster Ovary (CHO) cells resulting in high RNA and/or protein production. More specifically it relates to CHO cells comprising at least one heterologous polynucleotide stably integrated into the S100A gene cluster of the CHO genome and to methods for the production of said CHO cells. Further, the invention relates to a method for the production of a protein of interest using said CHO cell and to the use of said CHO cell for producing a protein of interest at high yield. Integration within these specific target regions leads to reliable, stable and high yielding production of an RNA and/or protein of interest, encoded by the heterologous polynucleotide.

19 Claims, 5 Drawing Sheets
Specification includes a Sequence Listing.

A)

B)

A)

B)

INTEGRATION SITES IN CHO CELLS

CROSS-REFERENCE TO RELATED APPLICATIONS

This application is a national phase entry pursuant to 35 U.S.C. § 371 of International Application No. PCT/EP2018/071733, filed Aug. 10, 2018, which claims priority to European Application No. EP 17185988.7, filed Aug. 11, 2017, the entire contents of which are incorporated by reference herein for all purposes.

TECHNICAL FIELD

The present invention relates to the identification of a genomic integration site for heterologous polynucleotides in Chinese Hamster Ovary (CHO) cells resulting in high RNA and/or protein production. More specifically it relates to CHO cells comprising at least one heterologous polynucleotide stably integrated into the S100A gene cluster of the CHO genome and to methods for the production of said CHO cells. Further, the invention relates to a method for the production of a protein of interest using said CHO cell and to the use of said CHO cell for producing a protein of interest at high yield. Integration within these specific target regions leads to reliable, stable and high yielding production of an RNA and/or protein of interest, encoded by the heterologous polynucleotide.

TECHNOLOGICAL BACKGROUND

Chinese hamster ovary (CHO) cells are the most popular host cells for the recombinant production of therapeutic proteins. Classical cell line development procedures rely on the random integration (RI) of expression vectors followed by selection and screening of subclones for optimal productivity behavior. Random integration is associated with a large heterogeneity in the resulting cell population, owing to unpredictable chromosomal positioning effects, variable copy numbers and stability issues. High producer cells account for only a small proportion of the randomly transfected cells and tend to be outgrown by low producer cells. Hence, a large number of clones need to be screened in order to identify and isolate one individual clone suitable for sustained biopharmaceutical protein production and fermentation process development.

Positional effects on the expression of heterologous genes can result from, e.g., chromatin structure, genomic imprinting or the presence of transcriptional regulator elements, such as genomic enhancer elements, silencer elements or promoter elements in the vicinity of the integration site (C. Wilson et al. Annu. Rev. Cell Biol. 1990, 6, 679-714). Many of these elements within the genome are not known or characterized, and the potential of a genomic locus in a cell line development process therefore hard to predict.

By replacing classical random integration with targeted integration (TI) of the protein expression vector into one or more pre-determined genomic locus/loci, these disadvantages can be overcome. Targeted integration makes the cell line development process much more predictable as all subclones will have identical genomic set ups negating the need for extensive screening procedures.

The challenge for a cell line development process that relies on targeted integration lies in the identification of a suitable genomic locus, often called a "hot spot". The ideal site(s) will support sufficient levels of protein expression from single or low copy numbers, exhibit long term stable expression levels without excessive down-regulation, be amplifiable using metabolic selection markers such as DHFR or GS in conjunction with MTX or MSX, and will be located so that integration of transgenes does not negatively impact cell growth or protein product profiles.

The S100A6 gene is part of the S100A gene cluster encoding a group of known calcium-binding proteins, e.g. S100A1, S100A13, S100A14, S100A16, S100A3, S100A2, S100A4, S100A5 and S100A6. The cluster comprises a "side cluster" including the S100A1, S100A13, S100A14 and S100A16 genes and a "main cluster", which includes the S100A3, S100A4, S100A5 and S100A6 genes.

In the present invention, it is shown that the stable integration of heterologous polynucleotides within the S100A gene cluster of the CHO cell genome increases the production of a heterologous gene product. Specifically, stable integration within the upstream and downstream regions flanking the S100A3/A4/A5/A6 main gene cluster, enables a predictable, high level and stable production of a heterologous gene product, including recombinant proteins, such as antibodies and fusion proteins, or regulatory RNAs, such as shRNAs or miRNAs.

SUMMARY OF THE INVENTION

In the present invention a Chinese hamster ovary (CHO) cell, comprising at least one heterologous polynucleotide, stably integrated into the S100A gene cluster of the CHO cell genome is provided, wherein the at least one heterologous polynucleotide is integrated upstream of the S100A3/A4/A5/A6 main gene cluster, into a genomic target region corresponding to the sequence of SEQ ID NO: 1; and/or the at least one heterologous polynucleotide is integrated downstream of the S100A3/A4/A5/A6 main gene cluster, into a genomic target region corresponding to the sequence of nucleotides 1 to 15,120 of SEQ ID NO: 2. Preferably the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

More preferably the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2. Even more preferably the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1; and/or the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In one embodiment the at least one heterologous polynucleotide is stably integrated into the CHO cell genome as part of an expression cassette. The at least one heterologous polynucleotide may code for a RNA and/or a protein. The RNA may be an mRNA, a miRNA or a shRNA. The protein may be a therapeutic protein, preferably a therapeutic protein selected from the group consisting of an antibody, a fusion protein, a cytokine and a growth factor.

The at least one heterologous polynucleotide may also be a marker gene selected from the group consisting of a reporter gene and a selection marker gene. Preferably the marker gene is stably integrated into the CHO cell genome as part of an expression cassette and the expression cassette is flanked by recognition sites for a site specific recombinase or a sequence specific DNA editing enzyme such as a site specific nuclease.

The CHO cell according to the invention may be a CHO-DG44 cell, a CHO-K1 cell, a CHO-DXB11 cell, a CHO-S cell, a CHO glutamine synthetase (GS)-deficient cell or a derivative of any of these cells.

In one embodiment the genomic target region consists of any one of the sequences defined in SEQ ID NO: 1 and/or SEQ ID NO: 2 above or a sequence having at least 80% sequence identity thereto.

The at least one heterologous polynucleotide may be stably integrated into one or both alleles of the S100A gene cluster of the CHO cell genome.

In another aspect the invention provides for a method for the production of a CHO cell, comprising the steps of (a) providing a CHO cell; (b) introducing a heterologous polynucleotide into said CHO cell, wherein the heterologous polynucleotide is stably integrated into the S100A gene cluster of the CHO cell genome, wherein said heterologous polynucleotide is integrated upstream of the S100A3/A4/A5/A6 main gene cluster, into a genomic target region corresponding to the sequence of SEQ ID NO: 1; and/or said heterologous polynucleotide is integrating downstream of the S100A3/A4/A5/A6 main gene cluster, into a genomic target region corresponding to the sequence of nucleotides 1 to 15,120 of SEQ ID NO: 2.

Preferably the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2. More preferably the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2. Even more preferably the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1, nucleotides 17,100 to 18,380 of SEQ ID NO: 1; and/or the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In one embodiment the genomic target region consists of any one of the sequences defined in SEQ ID NO: 1 and/or SEQ ID NO: 2 above or a sequence having at least 80% sequence identity thereto.

In a preferred embodiment the at least one heterologous polynucleotide is stably integrated into the CHO cell genome as part of an expression cassette and the expression cassette may be flanked by recognition sites for a site specific recombinase or a sequence specific DNA editing enzyme (e.g., a site specific nuclease).

In one embodiment the at least one heterologous polynucleotide is stably integrated into the CHO cell genome as part of an expression cassette. The at least one heterologous polynucleotide may code for a RNA and/or a protein. The RNA may be an mRNA, a miRNA or a shRNA. The protein may be a therapeutic protein, preferably a therapeutic protein selected from the group consisting of an antibody, a fusion protein, a cytokine and a growth factor.

The at least one heterologous polynucleotide may also be a marker gene selected from the group consisting of a reporter gene and a selection marker gene. Preferably the marker gene is stably integrated into the CHO cell genome as part of an expression cassette and the expression cassette is flanked by recognition sites for a site specific recombinase or a sequence specific DNA editing enzyme (e.g., a site specific nuclease).

The at least one heterologous polynucleotide may be stably integrated into one or both alleles of the S100A gene cluster of the CHO cell genome.

In one embodiment the heterologous polynucleotide is introduced into the CHO cell genome using (a) a sequence specific DNA editing enzyme, preferably a site specific nuclease, more preferably selected from the group consisting of zinc finger nucleases (ZFNs), meganucleases, transcription activator-like effector nucleases (TALENs) and CRISPR associated nucleases; or (b) a site-specific recombinase, preferably selected from the group consisting of lambda integrase, PhiC31 integrase, Cre, Dre and Flp.

In another embodiment the method may further comprise the steps of (a) providing a CHO cell; (aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme (e.g., a site specific nuclease), wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrated downstream of the S100A3/A4/A5/A6 main gene cluster, into a genomic target region corresponding to the sequence of nucleotides 1 to 15,120 of SEQ ID NO: 2; and introducing an expression cassette comprising a second heterologous polynucleotide into said CHO cell by replacing the expression cassette comprising the first heterologous polynucleotide of step aa).

In yet another aspect the invention provides a method for the production of a protein of interest in a CHO cell comprising (a) providing the CHO cell of the invention; (b) culturing the CHO cell of step a) in a cell culture medium at conditions allowing production of the protein of interest; (c) harvesting the protein of interest, and (d) optionally purifying the protein of interest.

The CHO cell used in the methods according to the invention may be a CHO-DG44 cell, a CHO-K1 cell, a CHO-DXB11 cell, a CHO-S cell, a CHO glutamine synthetase (GS)-deficient cell or a derivative of any of these cells.

In yet another aspect of the invention a use of the CHO cell of the invention producing a protein of interest at high yield is provided.

DETAILED DESCRIPTION OF PREFERRED EMBODIMENTS

Figure 1:
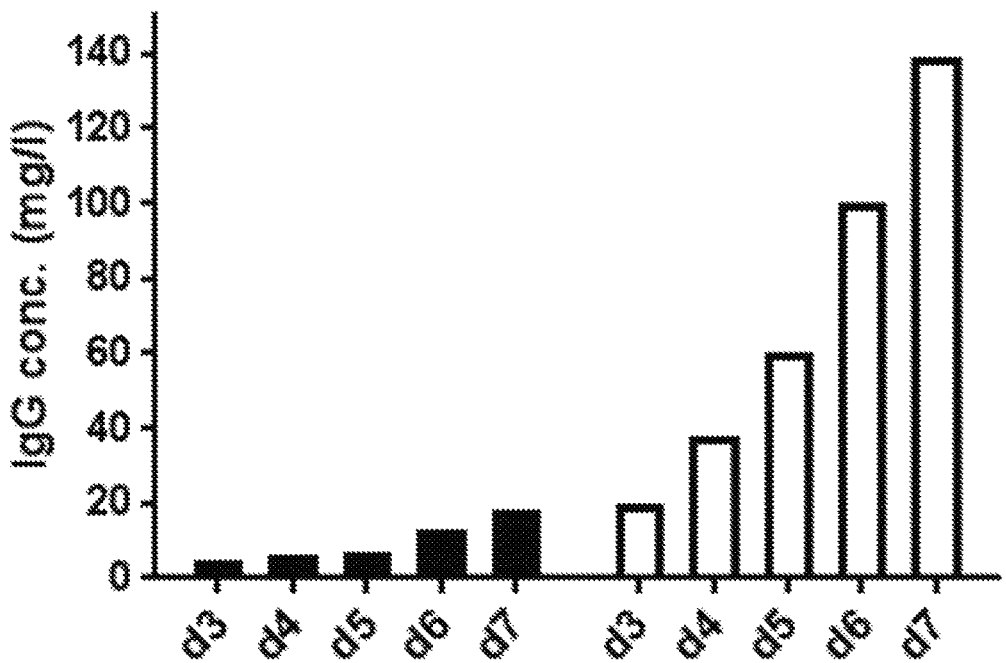
FIG. 1: Random versus targeted integration via ZFN (Pool data) in CHO cells. (A) Shown are IgG1 antibody concentrations from randomly integrated (black bars) versus targeted integrated (white bars) CHO-DG44 cell pools after 3-7 days of fed-batch culture. (B) Shown are IgG1 antibody concentrations from randomly integrated (black bars) versus targeted integrated (white bars) CHOZN GS cell pools after 8-10 days of fed-batch culture. TI pools were enriched using FACS cell sorting, metabolic selections and a second round of FACS. Targeted integration was zinc finger nuclease (ZFN) mediated using zinc finger nuclease pair (ZFN) 13 designed to integrate downstream of the S100A3/A4/A5/A6 main gene cluster.
Figure 1:
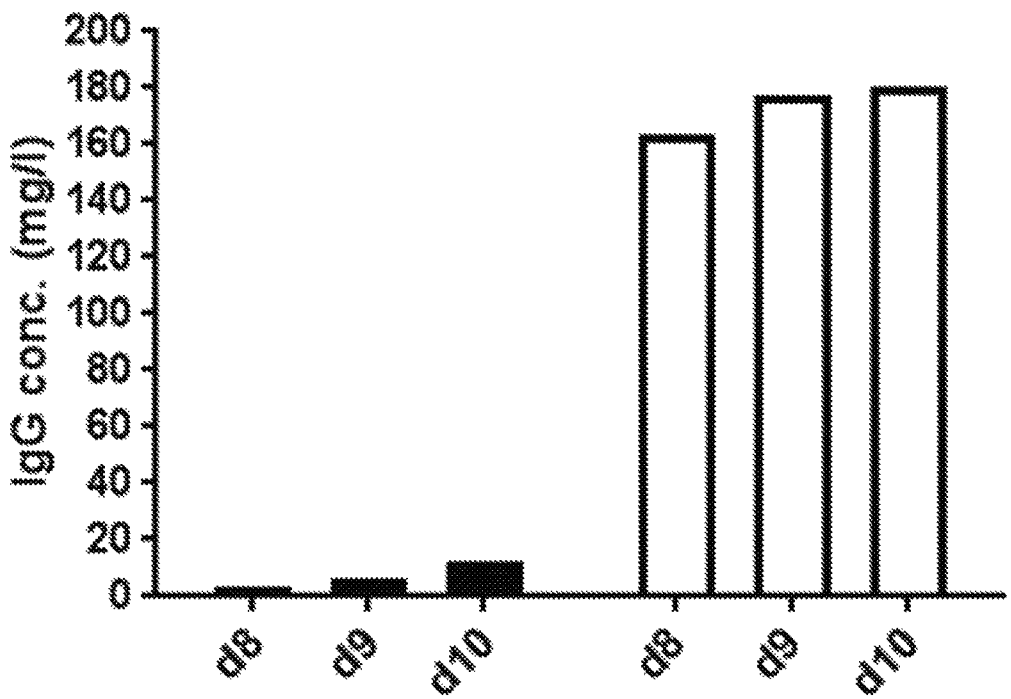

The general embodiments "comprising" or "comprised" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "homologue" or "homologous" as used in the present invention means a polypeptide molecule or a nucleic acid molecule, which is at least 80% identical in sequence with the original sequence or its complementary sequence. Preferably, the polypeptide molecule or nucleic acid molecule is at least 90% identical in sequence with the reference sequence or its complementary sequence. More preferably, the polypeptide molecule or nucleic acid molecule is at least 95% identical in sequence with the reference sequence or its complementary sequence. Most preferably, the polypeptide molecule or a nucleic acid molecule is at least 98% identical in sequence with the reference sequence or its complementary sequence. A homologous protein further displays the same or a similar protein activity as the original sequence.

The term "corresponding to the sequence" or "corresponds to the sequence", as used herein includes the defined sequence of *Cricetulus griseus* CHO-K1 having the sequence or the sequence between the defined nucleotides of SEQ ID NO: 1 or SEQ ID NO: 2, but also natural variations thereof. The skilled person will understand that genomic sequences of CHO cell lines vary and may therefore not be identical with the sequences obtained from NCBI database with the NCBI Reference Sequence: NW_003613854.1, and as shown in SEQ ID NOs: 1 and 2 due to, e.g., allelic variation. However, using sequence alignment, the skilled person would know how to identify the sequence in a specific CHO cell line corresponding to the sequence as defined in SEQ ID NO: 1 or 2, i.e., the homologous region. Such corresponding sequence would have at least 80% identity with the sequence defined in SEQ ID NO: 1 or with the sequence defined in SEQ ID NO: 2, preferably at least 90% identity with the sequence defined in SEQ ID NO: 1 or with the sequence defined in SEQ ID NO: 2 or is identical with SEQ ID NO: 1 or SEQ ID NO: 2. The corresponding sequence may also contain recombinant insertions, such as a heterologous polynucleotide, which is not to be considered for determining the corresponding sequence.

The term "protein" is used interchangeably with "amino acid residue sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties. The term "polypeptide" typically refers to a sequence with more than 10 amino acids and the term "peptide" means sequences with up to 10 amino acids in length. However, the terms may be used interchangeably. The protein of interest according to the present invention is preferably a therapeutic protein.

The term "protein of interest" broadly refers to any protein that is of specific relevance in an industrial protein production process. Proteins of interest include, but are not limited to heterologous therapeutic proteins, marker proteins or proteins of the host cell having a function in e.g. protein secretion, post-translational protein modification, translation, transcription, cell cycle regulation or nutrient metabolism.

The term "therapeutic protein" refers to proteins that can be used in medical treatment of humans and/or animals. These include, but are not limited to antibodies, growth factors, blood coagulation factors, vaccines, interferons, hormones and fusion proteins.

The term "genomic DNA", or "genome" is used interchangeably and refers to the heritable genetic information of a host organism. The genomic DNA comprises the DNA of the nucleus (also referred to as chromosomal DNA) but also of other cellular organelles (e.g., mitochondria).

The term "gene" as used herein refers to a DNA or RNA locus of heritable genomic sequence which affects an organism's traits by being expressed as a functional product or by regulation of gene expression. Genes and polynucleotides may include introns and exons as in genomic sequence, or just the coding sequences as in cDNAs, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA), double stranded RNA (dsRNA), genomic DNA, cDNA, cRNA, recombinant DNA or recombinant RNA and derivatives thereof, such as those containing modified backbones. Preferably, a polynucleotide, particularly to be stably integrated into the CHO genome is a DNA or cDNA. Polynucleotides according to the invention can be prepared in different ways (e.g. by chemical synthesis, by gene cloning etc.) and can take various forms (e.g. linear or branched, single or double stranded, or a hybrid thereof, primers, probes etc.). The term "nucleotide sequence" or "nucleic acid sequence" refers to both the sense and antisense strands of a nucleic acid as either individual single strands or in the duplex.

The term "heterologous polynucleotide" as used herein refers to a polynucleotide derived from a different organism or a different species from the recipient, i.e., a CHO cell. In the context of the present invention the skilled person would understand that it refers to a DNA or cDNA. A heterologous polynucleotide may also be referred to as transgene. Thus, it may be a gene or open reading frame (ORF) coding for a heterologous protein. In the context of the CHO cell "heterologous polynucleotide" refers to a polynucleotide derived from a different cell line, preferably a cell line not derived from *Cricetulus griseus*. The term "heterologous" when used with reference to portions of a nucleic acid may also indicate that the nucleic acid comprises two or more sequences that are not found in the same relationship to each other in nature. Heterologous may therefore also refer to a CHO derived polynucleotide sequence, such as a gene or transgene, or a portion thereof, being inserted into the CHO genome in a location in which it is not typically found, or a gene introduced into a cell of an organism in which it is not typically found.

"Heterologous polynucleotide", "heterologous gene" or "heterologous sequences" can be introduced into a target cell directly or preferably by using an "expression vector", preferably a mammalian expression vector. Methods used to construct vectors are well known to the person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in (Sambrook J, et al., 1989. Molecular Cloning: A Laboratory Manual. Cold Spring Harbor: Cold Spring Harbor Laboratory Press) and references cited therein. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses and bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art and some are commercially available from companies such as Stratagene, La Jolla, Calif.; Invitrogen, Carlsbad, Calif.; Promega, Madison, Wis. or BD Biosciences Clonetech, Palo Alto, Calif. Usually expression vectors also comprise an expression cassette encoding a selectable marker, allowing selection of host cells carrying said expression marker.

The term "producing" or "highly producing", "production", "production and/or secretion", "producing", "production cell" or "producing at high yield" as used herein relates to the production of the RNA and/or protein encoded by a heterologous polynucleotide. An "increased production and/or secretion" or "production at high yield" relates to the expression of the heterologous RNA and/or protein and means an increase in specific productivity, increased titer, increased overall productivity of the cell culture or a combination thereof. Preferably, the titer or the overall productivity and the titer are increased. Increased titer as used herein relates to an increased concentration in the same volume, i.e., an increase in total yield. The produced heterologous RNA, heterologous protein or therapeutic protein may be, for example, a small regulatory RNA or an antibody, preferably a micro RNA, a small hairpin RNA, a monoclonal antibody, a bispecific antibody or a fragment thereof, or a fusion protein.

The term "enhancement", "enhanced", "enhanced", "increase" or "increased", as used herein, generally means an increase by at least about 10% as compared to a control cell, for example an increase by at least about 20%, or at least about 30%, or at least about 40%, or at least about 50%, or at least about 75%, or at least about 80%, or at least about 90%, or at least about 100%, or at least about 200%, or at least about 300%, or any integer decrease between 10-300% as compared to a control cell. As used herein, a "control cell" or "control mammalian cell" is the same CHO cell in which the same heterologous polynucleotide has been introduced randomly. This may be determined in cell clones or preferably in a cell pool without clonal selection.

As used herein, the term "expression cassette" refers to the part of a vector comprising one or more genes encoding for a RNA (heterologous RNA) or a protein (heterologous protein) and the sequences controlling their expression. Thus it comprises a promoter sequence, an open reading frame and a 3' untranslated region, typically containing a polyadenylation site. Preferably, the vector is an expression vector comprising one or more gene encoding for the recombinant secreted therapeutic protein. It may be part of a vector, typically an expression vector, including a plasmid or a viral vector. It may also be integrated into a chromosome by random or targeted integration, such as by homologous recombination. An expression cassette is prepared using cloning techniques and does therefore not refer to a natural occurring gene structure.

A "promoter" or "promoter sequence" is a DNA regulatory region capable of binding RNA polymerase in a cell and initiating transcription of a downstream (3' direction) coding sequence. The promoter sequence is bounded at its 3' terminus by the transcription initiation site and extends upstream (5' direction) to include up to 1.5 kb. Typically, a promoter is about 100 to 1000 base pairs long. A promoter sequence comprises a transcription initiation site, as well as protein binding domains (consensus sequences) responsible for the binding of RNA polymerase. Eukaryotic promoters often, but not always, contain "TATA" boxes and "CAT" boxes. Promoter sequences often contain additional consensus sequences recognized by proteins involved in regulating expression of the respective gene. Regulation of gene expression by a promoter can occur by enhancing or inhibiting binding of a regulatory protein. Enhancing or inhibiting the binding or a regulatory protein can occur by many different means, including but not limited to, base modifications (i.e., methylation) and protein modification (i.e., phosphorylation).

The terms "upstream" and "downstream" refer to a relative position in DNA or RNA. Each strand of DNA or RNA possesses a 5' end and a 3' end, relating to the terminal carbon position of the deoxyribose or ribose units. By convention, "upstream" means towards the 5' end of a polynucleotide, whereas "downstream" means towards the 3' end of a polynucleotide. In the case of double stranded DNA, e.g. genomic DNA, the term "upstream" means towards the 5' end of the coding strand, whereas "downstream" means towards the 3' end of the coding strand.

The term "coding strand", "sense strand" or "non-template strand" refers to the strand of the double stranded DNA whose base sequence corresponds to the base sequence of the RNA which is transcribed from a gene.

The term "small regulatory RNA" refers to small non-coding RNA polynucleotides that influence the expression of target genes, usually by binding to their respective mRNAs. These small regulatory RNAs include, but are not limited to small interfering RNAs (siRNAs), micro RNAs (miRNAs) and short hairpin RNAs (shRNAs).

The term "ribonucleic acid", "RNA" or "RNA oligonucleotide" as used herein describes a molecule consisting of a sequence of nucleotides, which are built of a nucleobase, a ribose sugar, and a phosphate group. RNAs are usually single stranded molecules and can exert various functions. The term ribonucleic acid specifically comprises messenger RNA (mRNA), transfer RNA (tRNA), ribosomal RNA (rRNA), short interfering RNA (siRNA), small hairpin RNA (shRNA) and micro RNA (miRNA), each of which plays a specific role in biological cells. It includes small non-coding RNAs, such as microRNAs (miRNA), short interfering RNAs (siRNA), small hairpin RNA (shRNA), and Piwi-interacting RNAs (piRNA). The term "non-coding" means that the RNA molecule is not translated into an amino acid sequence.

The term "RNA interference" (RNAi) refers to sequence-specific or gene-specific suppression of gene expression (protein synthesis), without generalized suppression of protein synthesis. RNAi may involve degradation of messenger RNA (mRNA) by an RNA-induced silencing complex (RISC), preventing translation of the transcribed mRNA. The suppression of gene expression caused by RNAi may be transient or it may be more stable, even permanent. RNAi may be mediated by miRNA, siRNA or shRNA. Preferably the RNAi according to the invention is gene-specific (only one gene is targeted). Gene-specific RNAi may be mediated by siRNA or shRNA.

The terms "microRNA" or "miRNA" are used interchangeably herein. microRNAs are small, about 22 nucleotide-long (typically between 19 and 25 nucleotides in length) non-coding single stranded RNAs. miRNAs typically target more than one gene. microRNAs are encoded in the genome of eukaryotic cells and are typically transcribed by RNA Polymerase III as long primary transcripts that are then processed in several steps first into ~70nt-long hairpin-loop structures and subsequently into the ~22nt RNA duplex. The active mature strand is then loaded into the RNA-induced silencing complex (RISC) in order to block translation of target proteins or degradation of their respective mRNAs. Targeting with miRNAs allows for mismatches and mRNA translational repression is mediated by incomplete complementarity (i.e., imperfect base paring between the antisense strand of the RNA duplex of the small interfering RNA and the target mRNA), while siRNA and shRNA are specific for their targets due to complete sequence complementarity (i.e., perfect base pairing between the antisense strand of the RNA duplex of the small interfering RNA and the target mRNA). Typically, miRNAs bind in the 3'untranslated region (3'UTR) and are not gene-specific, but target multiple mRNAs. The term "microRNA" as used herein relates to endogenous genomic mammalian miRNAs, such as human miRNAs. The prefix "hsa" indicates, e.g., the human origin of a microRNA. They may be introduced into a mammalian host cell using an expression vector comprising genomic microRNA sequence(s) for transient or stable expression of miRNA in the mammalian host cell. Means for cloning genomic microRNA into an expression vector are known in the art. They include, cloning genomic miRNA sequences with approximately 300 bp flanking regions into a mammalian expression vector, such as pBIP-1, operably linked to a promoter. Alternatively one or more microRNAs may be cloned as polynucleotides encoding engineered pre-miRNA sequences (i.e., short hairpins) into a mammalian expression vector. For example, a mature miRNA sequence may be cloned into a given sequence encoding an optimized hairpin loop sequence and 3' and 5' flanking regions, such as derived from the murine miRNA mir-155 (Lagos-Quintana et al., 2002. Curr. Biol. 30; 12(9):735-9). A DNA oligonucleotide is designed, which encodes the miRNA sequence, the mentioned loop and the antisense sequence of the respective mature miRNA with a two nucleotide depletion to generate an internal loop in the hairpin stem. Furthermore, overhangs are added for cloning at both ends to fuse the DNA oligonucleotide to the 3' and 5' flanking regions. miRNAs as used herein further comprise non-canonical miRNAs. These RNAs can be derived from 'housekeeping' non-coding RNAs (ncRNA) including ribosomal RNA (rRNA) or transfer RNA (tRNA) and function in a miRNA-like manner. These RNAs can also originate from mammalian mitochondrial ncRNAs and are termed mitochondrial genome-encoded small RNAs (mitosRNAs).

As used herein, the terms "small interfering" or "short interfering RNA" or "siRNA" refer to an RNA duplex of nucleotides that is targeted to a desired gene and is capable of inhibiting the expression of a gene with which it shares homology. It is formed from long double stranded RNA (dsRNA) or shRNA. The RNA duplex typically comprises two complementary single-stranded RNAs of 19, 20, 21, 22, 23, 24, 25, 26, 27, 28 or 29 nucleotides that form 17, 18, 19, 20, 21, 22, 23, 24, 25, 26 or 27 base pairs and possess 3' overhangs of two nucleotides, preferably the RNA duplex comprises two complementary single stranded RNAs of 19-27 nucleotides that form 17-25 base pairs and possess 3' overhangs of two nucleotides. siRNA is "targeted" to a gene, wherein the nucleotide sequence of the duplex portion of the siRNA is complementary to a nucleotide sequence of the mRNA of the targeted gene. The siRNA or a precursor thereof is always exogenously introduced into the cell, e.g., directly or by transfection of a vector having a sequence encoding said siRNA, and the endogenous miRNA pathway is harnessed for correct processing of siRNA and cleavage or degradation of the target mRNA. The duplex RNA can be expressed in a cell from a single construct.

As used herein, the term "shRNA" (small hairpin RNA) refers to an RNA duplex wherein a portion of the siRNA is part of a hairpin structure (shRNA). The shRNA can be processed intracellularly into a functional siRNA. In addition to the duplex portion, the hairpin structure may contain a loop portion positioned between the two sequences that form the duplex. The loop can vary in length. In some embodiments the loop is 4, 5, 6, 7, 8, 9, 10, 11, 12, 13 or 14 nucleotides in length. The hairpin structure can also contain 3' or 5' overhang portions. In some aspects, the overhang is a 3' or a 5' overhang of 0, 1, 2, 3, 4 or 5 nucleotides in length. In one aspect of this invention, a nucleotide sequence comprised in the vector serves as a template for the expression of a small hairpin RNA, comprising a sense region, a loop region and an antisense region. Following expression the sense and antisense regions form a duplex. shRNA is always exogenously introduced, e.g., by transfection of a vector having a sequence encoding said shRNA, and the endogenous miRNA pathway is harnessed for correct processing of the siRNA and cleavage or degradation of the target mRNA. Use of a vector having a sequence encoding a shRNA has the advantage over use of chemically synthesized siRNA in that the suppression of the target gene is typically long-term and stable.

Typically siRNA and shRNA mediate mRNA repression by complete sequence complementarity (i.e., perfect base paring between the antisense strand of the RNA duplex of the small interfering RNA and the target mRNA) and are therefore specific for their target. The antisense strand of the RNA duplex may also be referred to as active strand of the RNA duplex. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. More preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides.

A "vector" is a nucleic acid that can be used to introduce a heterologous polynucleotide into a cell. One type of vector is a "plasmid", which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA or RNA segments can be introduced into the viral genome. Preferably the vector is a non-episomal mammalian vector integrating into the genome of a host cell upon introduction into the host cell and culturing under selective pressure, and thereby are replicated along with the host genome. A vector can be used to direct the expression of a chosen polynucleotide in a cell.

The term "encodes" and "codes for" refers broadly to any process whereby the information in a polymeric macromolecule is used to direct the production of a second molecule that is different from the first. The second molecule may have a chemical structure that is different from the chemical nature of the first molecule. For example, in some aspects, the term "encode" describes the process of semi-conservative DNA replication, where one strand of a double-stranded DNA molecule is used as a template to encode a newly synthesized complementary sister strand by a DNA-dependent DNA polymerase. In other aspects, a DNA molecule can encode an RNA molecule (e.g., by the process of transcription that uses a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein the term "gene cluster" refers to a segment of genomic DNA that encompasses a set or family of closely related genes which code for a group of related, or similar proteins and which are usually grouped together on the same chromosome. A gene cluster encompasses a segment of genomic DNA, wherein all the coding sequences for the group of proteins are located, including regions preceding (leader) and following (trailer) the coding sequences as well as intervening sequences (introns) between individual coding sequence fragments (exons) and further genetic elements in the broadest sense, including, but not limited to, transcriptional regulator elements, promoter elements, enhancer elements and repressor elements. Generally, the gene cluster encompasses the entire genomic segment limited by the first (5') protein coding gene of the gene cluster and the last (3') protein coding gene of the gene cluster.

The "S100A gene cluster" refers to a segment of Chinese hamster genomic DNA that codes for the group of calcium binding proteins S100A1, S100A3, S100A4, S100A5, S100A6, S100A13, S100A14 and S100A16. The segment comprises the most upstream gene coding for the S100A1 protein and the most downstream gene coding for the S100A6 protein. The term "S100A3/A4/A5/A6 main gene cluster" refers to a segment of genomic DNA that is encompassed by the S100A gene cluster and reaches from the gene coding for the S100A3 protein to the gene coding for the S100A6 protein (SEQ ID NO: 4). "S100A1" refers to the protein S100A1 from *Cricetulus griseus* and the gene coding for it (the S100A1 gene; NCBI Gene ID: 100769478). "S100A3" refers to the protein S100A3 from *Cricetulus griseus* and the gene coding for it (the S100A3 gene, NCBI Gene ID: 100770814). "S100A4" refers to the protein S100A4 from *Cricetulus griseus* and the gene coding for it (the S100A4 gene, NCBI Gene ID: 100770532). "S100A5" refers to the protein S100A5 from *Cricetulus griseus* and the gene coding for it (the S100A5 gene, NCBI Gene ID: 100771097). "S100A6" refers to the protein S100A6 from

*Cricetulus griseus* and the gene coding for it (the S100A6 gene; NCBI Gene ID: 100771384). "S100A13" refers to the protein S100A13 from *Cricetulus griseus* and the gene coding for it (the S100A13 gene; NCBI Gene ID: 100769763). "S100A14" refers to the protein S100A14 from *Cricetulus griseus* and the gene coding for it (the S100A14 gene; NCBI Gene ID: 100770053). "S100A16" refers to the protein S100A16 from *Cricetulus griseus* and the gene coding for it (the S100A16 gene; NCBI Gene ID: 100753026).

The term "allele" refers to any one of the different forms of a gene, genetic target region or generally DNA sequence at a single locus, i.e., chromosomal location. This includes coding sequences, non-coding sequences and regulatory sequences. Different alleles within a genome are not necessarily identical in nucleotide sequence.

The term "antibody" refers to a protein consisting of one or more polypeptides substantially encoded by immunoglobulin genes. The recognized immunoglobulin genes include the kappa, lambda, alpha, gamma, delta, epsilon and mu constant regions genes as well as the myriad immunoglobulin variable region genes. The terms "antibody" and "immunoglobulin" are used interchangeably and are used to denote, without being limited thereto, glycoproteins having the structural characteristics noted above for immunoglobulins.

The term "antibody" is used herein in its broadest sense and encompasses monoclonal antibodies (including full length monoclonal antibodies), polyclonal antibodies, chimeric antibodies, humanized antibodies, human antibodies, multispecific antibodies (e.g. bispecific antibodies), single domain antibodies, and antibody fragments (such as Fv, Fab, Fab', F(ab)2 or other antigen-binding subsequences of antibodies). The term "antibody" also encompasses antibody conjugates and fusion antibodies. Full length "antibodies" or "immunoglobulins" are generally heterotetrameric glycoproteins of about 150 kDa, composed of two identical light and two identical heavy chains. Each light chain is linked to a heavy chain by one covalent disulphide bond, while the number of disulphide linkages varies between the heavy chains of different immunoglobulin isotypes. Each heavy and light chain also has regularly spaced intrachain disulphide bridges. Each heavy chain has an amino terminal variable domain (VH) followed by three carboxy terminal constant domains (CH). Each light chain has a variable N-terminal domain (VL) and a single C-terminal constant domain (CL). The term "antibody" further refers to a type of antibody comprising a plurality of individual antibodies having the same specificity (variable domain) and having the same constant domains.

A "fusion protein" is defined as a protein which contains the complete sequences or any parts of the sequences of two or more originally separate natural or modified heterologous proteins or a composition of complete sequences or any parts of the sequences of two or more originally separate natural or modified heterologous proteins. Fusion proteins can be constructed by genetic engineering approaches by fusing the two or more genes, or parts thereof, that originally encode the two or more originally separate natural or heterologous proteins, or parts thereof. This results in a fusion protein with functional properties derived from each of the original proteins. Fusion proteins include, but are not limited to Fc fusion proteins.

The term "cytokine" refers to small proteins, which are released by cells and act as intercellular mediators, for example influencing the behavior of the cells surrounding the secreting cell. Cytokines may be secreted by immune or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

As used herein, "growth factor" refers to proteins or polypeptides that are capable of stimulating cell growth. They include, but are not limited to, insulin, epidermal growth factor (EGF), ephrins (Eph), Erythropoietin, glia-cell stimulating factor (GSF); colony-stimulating factors (CSF) including macrophage colony-stimulating factor (M-CSF), granulocyte macrophage colony-stimulating factor (GM-CSF), and granulocyte colony-stimulating factor (G-CSF); stem cell growth factor (SCGF) (also called Steel Factor); stromal cell-derived factor (SDF), effective fragments thereof, and combinations thereof; and vascular endothelial growth factor (VEGF). Other growth factors can include hepatocyte growth factor (HGF), Angiopoietin-1, Angiopoietin-2, b-FGF, and FLT-3 ligand, and effective fragment thereof.

The term "expression" as used herein refers to transcription and/or translation of a heterologous nucleic acid sequence within a host cell. The level of expression of a gene product of interest in a host cell may be determined on the basis of either the amount of corresponding RNA that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

The term "gene product" refers to both the RNA polynucleotide and polypeptide that is encoded by a gene or DNA polynucleotide.

A "marker gene" as used herein means a polynucleotide, the expression of which in a cell confers a selectable or distinguishable phenotype (e.g., antibiotic resistance, expression of a fluorescent protein or reporter gene, modified metabolism) to the cell.

As used herein, a "reporter gene" is a polynucleotide encoding a protein whose expression by a host cell can be detected and quantified. Thus, a measurement of the level of expression of the reporter is typically indicative of the level of activation of the promoter element that directs expression of the gene encoding the reporter (reporter gene) within the host cell genome. For example, a reporter gene can encode a protein, for example, an enzyme whose activity can be quantified, for example, alkaline phosphatase (AP), chloramphenicol acetyltransferase (CAT), Renilla luciferase or firefly luciferase protein(s). Reporters also include fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives).

A "selectable marker gene" or "selection marker gene" is a gene which encodes a selectable marker and allows the specific selection of cells which contain this gene, typically by the addition of a corresponding "selecting agent" to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or ganciclovir leads to the elimination thereof. The selectable marker genes useful in this invention also include the amplifiable selectable markers. The literature describes a large number of selectable marker genes including bifunctional (positive/negative) markers (see for example WO 92/08796 and WO 94/28143). Examples of selectable markers which are useful in the present invention include, but are not limited to the genes of aminoglycoside phosphotransferase (APH), hygromycine phosphotransferase (HYG), dihydrofolate reductase (DHFR), thymidine kinase (TK), glutamine synthetase, asparagine synthetase and genes which confer resistance to neomycin (G418/Geneticin), puromycin, histidinol D, bleomycin, phleomycin, blasticidin and zeocin. Also included are genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains, which are deemed to be selective.

Selection may also be made by fluorescence activated cell sorting (FACS) using for example a cell surface marker, bacterial β-galactosidase or fluorescent proteins (e.g. green fluorescent proteins (GFP) and their variants from Aequorea victoria and Renilla reniformis or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" or "selective agent" refers to a substance that interferes with the growth or survival of a cell, unless a certain selectable marker gene product is present in the cell which alleviates the effect of the selection agent. For example, to select for the presence of an antibiotic resistance gene like APH (aminoglycoside phosphotransferase) in a transfected cell the antibiotic Geneticin (G418) is used.

The "amplifiable selectable marker gene" usually codes for an enzyme, which is needed for the growth of eukaryotic cells under certain cultivation conditions. For example, the amplifiable selectable marker gene may code for dihydrofolate reductase (DHFR) or glutamine synthetase (GS).

In this case the marker gene is amplified, if a host cell transfected therewith is cultivated in the presence of the selecting agent methotrexate (MTX) or methionine sulphoximine (MSX), respectively. Sequences linked to the amplifiable selectable marker gene (i.e., sequences physically proximal thereto) are co-amplified together with the amplifiable selectable marker gene. Said co-amplified sequences may be introduced on the same expression vector or on separate vectors.

The following Table 1 gives non-limiting examples of amplifiable selectable marker genes and the associated selecting agents, which may be used according to the invention. Suitable amplifiable selectable marker genes are also described in an overview by Kaufman (Kaufman R J, 1990. Methods Enzymol. 185:537-566).

TABLE 1

Amplifiable selectable marker genes

| Amplifiable selectable marker gene | Accession number | Selecting agent |
| --- | --- | --- |
| dihydrofolate reductase (DHFR) | M19869 (hamster) E00236 (mouse) | methotrexate (MTX) |
| metallothionein | D10551 (hamster) M13003 (human) M11794 (rat) | cadmium |
| CAD (carbamoylphosphate synthetase:aspartate transcarbamylase:dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D1277 (human) J02811 (rat) | adenine, azaserin, coformycin |
| UMP-synthase | J03626 (human) | 6-azauridine, pyrazofuran |
| IMP 5'-dehydrogenase | J04209 (hamster) J04208 (human) M33934 (mouse) | mycophenolic acid |
| xanthine-guanine-phosphoribosyltransferase | X00221 (*E. coli*) | mycophenolic acid with limiting xanthine |
| mutant HGPRTase or mutant thymidine-kinase | J00060 (hamster) M13542, K02581 (human) J00423, M68489 (mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |

TABLE 1-continued

Amplifiable selectable marker genes

| Amplifiable selectable marker gene | Accession number | Selecting agent |
|---|---|---|
| P-glycoprotein 170 (MDR1) | AF016535 (human) J03398 (mouse) | several drugs, e.g. adriamycin, vincristin, colchicine |
| ribonucleotide reductase | M124223, K02927 (mouse) | aphidicoline |
| glutamine-synthetase (GS) | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoromethylornithine |
| HMG-CoA-reductase | L00183, M12705 (hamster) M11058 (human) | compactin |
| N-acetylglucosaminyl-transferase | M55621 (human) | tunicamycin |
| threonyl-tRNA-synthetase | M63180 (human) | borrelidin |
| Na⁺K⁺-ATPase | J05096 (human) M14511 (rat) | ouabain |

According to the invention a preferred amplifiable selectable marker gene is a gene which codes for a polypeptide with the function of GS or DHFR.

The term "site specific recombinase" refers to proteins that recognize specific nucleotide sequences (recognition sites), cleave the DNA backbone at these sites, perform a rearrangement and re-ligate the cleaved nucleotide sequences. Said recombinases for example allow the excision of the DNA between a pair of recognition sites and the subsequent integration of a polynucleotide of interest instead of the excised DNA fragment, thereby providing a precise site-specific exchange of genetic information. Several site-specific recombinases are known in the art. For instance, Cre recombinase recognizes either loxP recombination sites or lox511 recombination sites which are hetero-specific, which means that loxP and lox511 do not recombine together. The Cre/lox system is, e.g., described in Odell et al., Plant Physiol. 1994, 106 (2), 447-58. Flp recombinase recognizes frt recombination sites as, e.g., described in Lyznik et al., Nucleic Acids Res. 1996, 24(19), 3784-9. The phiC31 integrase recognizes attachment (att) sites, such as attB (donor) and attP (acceptor) as, e.g., described in Groth et al., Proc. Natl. Acad. Sci. U.S.A. 2000, 97(11), 5995-6000. The Dre recombinase recognizes rox sites as, e.g., described in U.S. Pat. No. 7,422,889. The Int recombinase from bacteriophage lambda (lambda integrase) and its recombination sites are described in Landy, Annu. Rev. Biochem. 1989, 58, 913-49.

According to the invention, a "sequence specific DNA editing enzyme" or a "site specific nuclease" is a protein that enables the cleavage of DNA at defined nucleotide sequences (recognition sites). Said cleavage may occur on one or both of two complementary DNA strands and thus allow, for example targeted mutagenesis, targeted deletion of specific genomic DNA sequences or result in the site-directed recombination of the cleaved target DNA with a heterologous polynucleotide. The sequence specificity of said editing enzymes may result from one or more sequence specific DNA binding protein domains within the editing enzyme, or from the enzyme binding a guide polynucleotide (e.g. guide RNA) that directs it to a DNA sequence with at least partial complementarity to said guide polynucleotide. The recognition site of said editing enzymes may therefore be altered by engineering the DNA binding protein domains, or using alternative guide polynucleotides. Multiple sequence specific DNA editing enzymes are known in the art, non-limiting examples of which are zinc finger nucleases (ZFNs), meganucleases, transcription activator-like effector nucleases (TALENs) and CRISPR associated nucleases.

The term "stable integration" or "stably integrated" as used in the patent refers to a heterologous polynucleotide being introduced into a host cell genome, as opposed to transiently introduced polynucleotides that remain separate from the genomic DNA of the host cell. Stable integration may occur by homologous recombination or other types of recombination. Stable integration may comprise a step of transient introduction of a heterologous polynucleotide into a host cell.

Stable Integration of at Least One Heterologous Polynucleotide into the S100A Gene Cluster The present invention relates to a CHO cell comprising at least one heterologous polynucleotide, stably integrated into the S100A gene cluster of the CHO cell genome, wherein (a) the at least one heterologous polynucleotide is integrated upstream of the S100A3/A4/A5/A6 main gene cluster, into a genomic target region corresponding to the sequence of SEQ ID NO: 1 (referred to as upstream genomic target region); and/or (b) the at least one heterologous polynucleotide is integrated downstream of the S100A3/A4/A5/A6 main gene cluster, into a genomic target region corresponding to the sequence of nucleotides 1 to 15,120 of SEQ ID NO: 2 (referred to as downstream genomic target region).

The S100A3/A4/A5/A6 main gene cluster refers to the genomic region encompassing the Chinese hamster genes coding for the S100 calcium binding protein A3 (S100A3), the S100 calcium binding protein A4 (S100A4), the S100 calcium binding protein A5 (S100A5) and the S100 calcium binding protein A6 (S100A6) in the above order, i.e., the region from the start of S100A3 to the end of S100A6

(corresponding to 1,782,882 to 1,810,338 of *Cricetulus griseus* unplaced genomic scaffold, CriGri_1.0 scaffold682, whole genome shotgun sequence of the CHO-K1 cell line; NCBI Reference Sequence: NW_003613854.1, corresponding to the sequence of SEQ ID NO: 4, or a homologous thereof). The genomic target region upstream of the S100A3/A4/A5/A6 main gene cluster refers to a genomic region corresponding to the sequence of SEQ ID NO: 1. The genomic target region downstream of the S100A3/A4/A5/A6 main gene cluster refers to a genomic region corresponding to the sequence of nucleotides 1 to 15,120 of SEQ ID NO: 2.

In one embodiment the at least one heterologous polynucleotide is stably integrated into the upstream genomic target region corresponding to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; preferably into the upstream genomic target region corresponding to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, and more preferably into the upstream genomic target region corresponding to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1.

In another embodiment the at least one heterologous polynucleotide is stably integrated into the downstream genomic target region corresponding to nucleotides 1 to 13,160 of SEQ ID NO: 2, nucleotides 1 to 12,000 of SEQ ID NO: 2 or nucleotides 1 to 10,260 of SEQ ID NO: 2, preferably into the downstream genomic target region corresponding to nucleotides 660 to 10,260 of SEQ ID NO: 2, nucleotides 1,320 to 10,260 of SEQ ID NO: 2 or nucleotides 1,480 to 10,260 of SEQ ID NO: 2; and more preferably into the downstream genomic target region corresponding to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In another embodiment the at least one heterologous polynucleotide is stably integrated into the upstream genomic target region and into the downstream genomic target region as disclosed above. Wherein the at least one heterologous polynucleotide integrated into the upstream genomic target region and the at least one heterologous polynucleotide stably integrated into the downstream, genomic target region may be the same or different.

The skilled person will understand that a single copy, a plurality of copies of one heterologous polynucleotide, or two or more different heterologous polynucleotides may be stably integrated into the upstream genomic target region, into the downstream genomic target region, or into the upstream genomic target region and the downstream genomic target region.

The at least one heterologous polynucleotide may be stably integrated into one or both alleles of the genomic target region(s).

In another aspect the present invention relates to a method for the production of a CHO cell comprising the steps of (a) providing a CHO cell; (b) introducing a heterologous polynucleotide into said CHO cell, wherein the heterologous polynucleotide is stably integrated into the S100A gene cluster of the CHO cell genome, wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrating downstream of the S100A3/A4/A5/A6 main gene cluster, into a genomic target region corresponding to the sequence of nucleotides 1 to 15,120 of SEQ ID NO: 2.

In one embodiment the at least one heterologous polynucleotide is stably integrated into the upstream genomic target region corresponding to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; preferably into the upstream genomic target region corresponding to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, and more preferably into the upstream genomic target region corresponding to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1.

In another embodiment the at least one heterologous polynucleotide is stably integrated into the downstream genomic target region corresponding to nucleotides 1 to 13,160 of SEQ ID NO: 2, nucleotides 1 to 12,000 of SEQ ID NO: 2 or nucleotides 1 to 10,260 of SEQ ID NO: 2, preferably into the downstream genomic target region corresponding to nucleotides 660 to 10,260 of SEQ ID NO: 2, nucleotides 1,320 to 10,260 of SEQ ID NO: 2 or nucleotides 1,480 to 10,260 of SEQ ID NO: 2; and more preferably into the downstream genomic target region corresponding to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In another embodiment the heterologous polynucleotide stably integrated into the genome of the CHO cell of the invention or the CHO cell produced by the method of the invention is integrated upstream of the S100A3/A4/A5/A6 main gene cluster, into a genomic target region having the sequence of SEQ ID NO: 1, or at least 80% homology thereto; and/or (ii) said heterologous polynucleotide is integrated downstream of the S100A3/A4/A5/A6 main gene cluster, into a genomic target region having the sequence of nucleotides 1 to 15,120 of SEQ ID NO: 2 or at least 80% homology thereto.

In one embodiment the at least one heterologous polynucleotide is stably integrated into the upstream genomic target region having the sequence of nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1, or at least 80% homology thereto; preferably into the upstream genomic target region having the sequence of nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, or at least 80% homology thereto, and more preferably into the upstream genomic target region having the sequence of nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1, or at least 80% homology thereto.

In another embodiment the at least one heterologous polynucleotide is stably integrated into the downstream genomic target region having the sequence of nucleotides 1 to 13,160 of SEQ ID NO: 2, nucleotides 1 to 12,000 of SEQ ID NO: 2 or nucleotides 1 to 10,260 of SEQ ID NO: 2, or at least 80% homology thereto, preferably into the downstream genomic target region having the sequence of nucleotides 660 to 10,260 of SEQ ID NO: 2, nucleotides 1,320 to 10,260 of SEQ ID NO: 2 or nucleotides 1,480 to 10,260 of SEQ ID NO: 2, or at least 80% homology thereto; and more preferably into the downstream genomic target region having the sequence of nucleotides 3,180 to 10,260 of SEQ ID NO: 2, nucleotides 4,920 to 9,000 of SEQ ID NO: 2 or nucleotides 6,720 to 8,460 of SEQ ID NO: 2, or at least 80% homology thereto.

In another embodiment the heterologous polynucleotide stably integrated into the genome of the CHO cell of the invention or the CHO cell produced by the method of the invention is stably integrated into the upstream genomic target region and into the downstream genomic target region as disclosed above. Wherein the at least one heterologous polynucleotide integrated into the upstream genomic target region and the at least one heterologous polynucleotide stably integrated into the downstream, genomic target region may be the same or different.

The skilled person will understand that a single copy, a plurality of copies of one heterologous polynucleotide, or two or more different heterologous polynucleotides may be stably integrated into the upstream genomic target region, into the downstream genomic target region, or into the upstream genomic target region and the downstream genomic target region.

The at least one heterologous polynucleotide may be stably integrated into one or both alleles of the genomic target region(s).

Methods for stable integration are well known in the art. Briefly, stable integration is commonly achieved by transiently introducing the at least one heterologous polynucleotide or a vector containing the at least one heterologous polynucleotide into the CHO host cell, which facilitates the stable integration of said heterologous polynucleotide(s) into the CHO cell genome. Typically the heterologous polynucleotide is flanked by homology arms, i.e., sequences homologous to the region upstream and downstream to the integration site. A vector to introduce the heterologous polynucleotide into the CHO cell of the invention may be chosen from a great variety of suitable vector systems, such as plasmids, retroviruses, cosmids, EBV-derived episomes, and the like. Various shuttle vectors may be used, e.g., vectors which may autonomously replicate in a plurality of host microorganisms such as E. coli and Pseudomonas sp. Before their introduction into the CHO host cell, circular vectors may be linearized to facilitate integration into the CHO cell genome. Methods for the introduction of vectors into CHO cells are well known in the art and include transfection with biological methods, such as viral delivery, with chemical methods, such as using cationic polymers, calcium phosphate, cationic lipids or cationic amino acids; with physical methods, such as electroporation or microinjection; or with mixed approaches, such as protoplast fusion.

To enable identification or selection of recombinant cells, the at least one heterologous polynucleotide may be integrated together with a selection marker gene or a reporter gene, preferably present on the same vector. Further, the vector often includes a marker outside the homology arms allowing to identify random integration.

In one embodiment the heterologous polynucleotide stably integrated into the genome of the CHO cell of the invention, or the CHO cell produced by the method of the invention are part of an expression cassette. An expression cassette comprises at least one heterologous polynucleotide coding for a gene product, such as a RNA and/or a protein, operably linked to a promoter and optionally further means controlling the expression of the gene product(s). Such means include, but are not limited to enhancers, termination signals, polyadenylation signals and a 3' untranslated region, typically containing a polyadenylation site. The promoter may be a weak promoter, or a strong promoter supporting high level expression of the gene product of interest. Said promoters include, but are not limited to CMV (cytomegalovirus) promoters, SV40 (Simian vacuolating virus 40) promoters, the RSV (Rous Sarcoma Virus) promoters, adenovirus promoters (e.g., the adenovirus major late promoter (AdMLP), CHEF-1 (CHO-derived elongation factor-1) promotors, polyoma and strong mammalian promoters such as native immunoglobulin and actin promoters or the natural promoter of the at least one heterologous polynucleotide. Preferably, the promoter is a CMV promoter or an SV40 promoter, most preferably a CMV promoter. Examples for polyadenylation signals are BGH polyA, SV40 late or early polyA; alternatively, 3'UTRs of immunoglobulin genes etc. can be used. The skilled person will further understand that the 3' untranslated region may be engineered to support high level expression, e.g., by removing instability elements, such as AREs (adenylate-uridylate rich elements).

In some embodiments, the gene product may be placed under the control of an amplifiable genetic selection marker, such as dihydrofolate reductase (DHFR), glutamine synthetase (GS). The amplifiable selection marker gene can be on the same expression vector as the secreted therapeutic protein expression cassette. Alternatively, the amplifiable selection marker gene and the secreted therapeutic protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of the gene product in the host cell or the producer cell may be achieved, e.g., by cloning multiple copies of a heterologous polynucleotide into an expression vector. Cloning multiple copies of the heterologous polynucleotide into an expression vector and amplifying the secreted therapeutic protein expression cassette as described above may further be combined.

The at least one heterologous polynucleotide encoding a gene product of interest may comprise a full length or a truncated gene, a fusion or tagged gene, and can be a cDNA, a genomic DNA, or a DNA fragment, preferably a cDNA. It can comprise the native sequence, i.e., naturally occurring form(s), or can be mutated or otherwise modified as desired. These modifications include codon optimizations to optimize codon usage in the selected host cell, humanization, fusion or tagging. The skilled person will understand that if more than one heterologous polynucleotide is stably integrated into the genome of the CHO cell of the invention or the CHO cell produced by the method of the invention, they may be encoded by more than one expression cassettes, or as part of the same expression cassette separated, e.g., by an IRES (internal ribosome entry site) sequence.

In another embodiment, the heterologous polynucleotide encodes at least one protein of interest and/or at least one RNA of interest. RNAs of interest include, but are not limited to messenger RNAs (mRNAs) and small regulatory RNAs, such as microRNAs (miRNAs) or small hairpin RNAs (shRNAs). Preferably, the RNA of interest is selected from the group consisting of an mRNA, a miRNA or an shRNA, more preferably an mRNA or an shRNA. The small regulatory RNA may interfere with the expression of one or more host cell protein(s), by binding to (a) target region(s) within mRNAs coding for said host cell protein(s).

The person of skill will understand that small regulatory RNAs encoded by the heterologous polynucleotide may be used to interfere with relevant processes in the host cell, such as nutrient metabolism, nutrient uptake, transcription, translation, protein folding, the unfolded protein response, apoptosis, inter- or intracellular signaling, cell cycle control, cell growth or protein secretion. Thus, the invention can be advantageously used to engineer CHO host cells to improve their characteristics in cell culture or protein production.

The RNA of interest and/or the protein of interest may be constitutively or conditionally expressed. For example, expression of the RNA of interest or protein of interest may be silent during growth phase and switched on during protein production phase.

The protein of interest encoded by the at least one heterologous polynucleotide stably integrated into the genome of the CHO cell of the invention or the CHO cell produced or used by the method of the invention may be a therapeutic protein selected from the group consisting of an antibody, a fusion protein, a cytokine or a growth factor, a lymphokine, an adhesion molecule, a receptor and a derivative or fragment thereof, and any other polypeptide that can serve as agonists or antagonists and/or have therapeutic or diagnostic use. Preferably the therapeutic protein is a secreted therapeutic protein. The therapeutic protein encoded by the heterologous polynucleotide may be a recombinant protein, preferably a secreted recombinant protein. Preferably, the therapeutic protein is selected from the group consisting of an antibody, a fusion protein, a cytokine or a growth factor, more preferably an antibody or a fusion protein and most preferably an antibody. Multimeric proteins, such as antibodies, may be encoded by one or more heterologous polynucleotides as part of one or more expression cassette(s).

The person of skill will understand that the at least one polynucleotide stably integrated into the genome of the CHO cell of the invention or the CHO cell produced by the method of the invention may code for both, at least one RNA of interest and at least one protein of interest, advantageously combining said modification of relevant processes in the CHO cell with the expression of a heterologous protein of interest to facilitate high level and/or stable protein production, high level and/or stable protein secretion and/or a specific amount and quality of posttranslational protein modification(s).

In another embodiment, the at least one heterologous polynucleotide stably integrated into the genome of the CHO cell of the invention or the CHO cell produced by the method of the invention is a marker gene. Such a marker gene may be any gene that enables a distinction between recombinant and non-recombinant cells and/or the quantification of the expression level of a gene product of interest. The marker gene may be a reporter gene or a selection marker gene. Selection markers may compensate for metabolic defects of the utilized CHO host cell, e.g. glutamine synthetase (GS) deficiency. Reporter genes may be alkaline phosphatase (AP), chloramphenicol acetyltransferase (CAT), Renilla luciferase or firefly luciferase protein(s). Reporter genes also include genes coding for fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives). In a preferred embodiment, the reporter gene may be a fluorescent protein, such as GFP or EGFP. The selection marker may further be an antibiotic resistance gene or metabolic marker gene like aminoglycoside phosphotransferase (APH), hygromycine phosphotransferase (HYG), dihydrofolate reductase (DHFR), thymidine kinase (TK), glutamine synthetase, asparagine synthetase and genes which confer resistance to neomycin (G418/Geneticin), puromycin, histidinol D, bleomycin, phleomycin, blasticidin and zeocin. In preferred embodiments, the selection marker gene is dihydrofolate reductase (DHFR) or glutamine synthetase (GS).

In some embodiments, the at least one heterologous polynucleotide stably integrated into the genome of the CHO cell of the invention or the CHO cell produced or used by the method of the invention is part of an expression cassette. Preferably, the expression cassette is flanked by recognition sites (recognition sequence) for a site specific recombinase or a sequence specific DNA editing enzyme such as a site specific nuclease. More preferably, it is flanked by recognition sites for a site specific recombinase. Site specific recombinases are well known in the art and include, without being limited thereto, lambda integrase, PhiC31 integrase, Cre, Dre and Flp, or any derivatives thereof. Thus, the expression cassette may be flanked by recognition sites for lambda integrase, PhiC31 integrase, Cre, Dre, Flp or any derivatives thereof. Site specific nucleases include, but are not limited to zinc finger nucleases (ZFNs), meganucleases, transcription activator-like effector nucleases (TALENs) and CRISPR associated nucleases. It is well known in the art that site specific nucleases may be engineered to specifically bind a target sequence within the CHO cell genome. This facilitates the targeted exchange of DNA segments within the expression cassette enclosed by said recognition sites. The use of site specific recombinases or site specific nucleases for the targeted integration of heterologous polynucleotides into host cell genomes is routinely practiced and the respective methods are well known in the art. In some embodiments, the expression cassette comprising recognition sites for site specific recombinases or site specific nucleases may allow re-targeting of a defined genomic target region, to create multiple CHO production cells for multiple gene products, such as RNAs of interest or proteins of interest.

In a specific embodiment the at least one heterologous polynucleotide stably integrated into the genome of the CHO cell of the invention or the CHO cell produced by the method of the invention is a marker gene and the marker gene is stably integrated into the CHO cell genome as part of an expression cassette and the expression cassette is flanked by recognition sites for a site specific recombinase or a sequence specific DNA editing enzyme (e.g., a site specific nuclease), preferably a site specific recombinase, as described above. This allows the expression cassette comprising a marker gene to be easily exchanged against an expression cassette comprising a heterologous polynucleotide coding for an RNA or a therapeutic protein of interest. Such a replacement DNA coding for a marker gene that can be easily exchanged against an expression cassette comprising heterologous polynucleotide coding a protein of interest is also referred to as "landing pad" herein.

In one embodiment, the method for the production of a CHO cell according to the invention comprises the steps of (a) providing a CHO cell; (aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme (e.g., a site specific nuclease), wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrated downstream of the S100A3/A4/A5/A6 main gene cluster, into a genomic target region corresponding to the sequence of nucleotides 1 to 15,120 of SEQ ID NO: 2; and (b) introducing an expression cassette comprising a second heterologous polynucleotide into said CHO cell by replacing the expression cassette comprising the first heterologous polynucleotide of step (aa). Preferably the second heterologous polynucleotide codes for a RNA or a therapeutic protein, preferably for a therapeutic protein, more preferably a secreted protein of interest.

Said first heterologous polynucleotide preferably encodes a marker gene selected from the group consisting of a reporter gene and a selection marker gene. In specific embodiments, the reporter gene may be a fluorescent protein, such as GFP. The selection marker may be dihydrofolate reductase (DHFR) or glutamine synthetase (GS). Reporter and selection marker genes may also be combined.

Preferably, said first heterologous polynucleotide is integrated by targeted integration using a site-specific nuclease, more preferably by using a site-specific nuclease selected from the group of zinc finger nucleases (ZFNs), meganucleases, transcription activator-like effector nucleases (TALENs) and CRISPR associated nucleases, even more preferably by using a zinc finger nuclease (ZFN), a transcription activator-like effector nuclease (TALEN) or a CRISPR associated nuclease.

Said first heterologous polynucleotide may further be part of an expression cassette flanked by recognition sites for a site-specific recombinase. Preferably, it comprises recognition sites for a site specific recombinase selected from the group consisting of lambda integrase, PhiC31 integrase, Cre, Dre and Flp.

Further, an expression cassette comprising a second heterologous polynucleotide may be introduced into the CHO cell by replacing the expression cassette comprising said first heterologous polynucleotide. Preferably, said second heterologous polynucleotide encodes at least one RNA and/or at least one protein. More preferably it encodes an mRNA, miRNA or shRNA and/or a therapeutic protein. Said expression cassette comprising a second heterologous polynucleotide may be stably introduced into the CHO cell genome by targeted integration, preferably by using a site specific nuclease, or a site specific recombinase, more preferably by using a site specific recombinase, most preferably by using a site specific recombinase selected from the group consisting of lambda integrase, PhiC31 integrase, Cre, Dre and Flp.

In a preferred embodiment, the method for the production of a CHO cell comprises introducing an expression cassette encompassing a first heterologous polynucleotide comprising a marker gene and recognition sites for a site-specific recombinase, wherein said first polynucleotide is stably integrated into the CHO cell genome by targeted integration, using a site specific nuclease. Further, said expression cassette encompassing the first heterologous polynucleotide is replaced by an expression cassette comprising a second heterologous polynucleotide, coding for a RNA of interest, and/or protein of interest, by targeted integration, using a site specific recombinase. In a preferred embodiment the expression cassette comprising the first heterologous polynucleotide and the expression cassette comprising the second heterologous polynucleotide, are flanked by the same recognition site for a site specific recombinase.

The person skilled in the art will understand that such a method provides a CHO cell comprising a genomic target site which is re-targetable to introduce any heterologous polynucleotides within a genomic locus supporting stable and high level expression of a gene product of interest by readily available DNA recombination methods. This may greatly reduce the time and cost associated with generating and identifying CHO production cell clones in a cell line development process.

CHO Cells

The CHO cell of the invention or the CHO cell produced by the method of the invention may be any Chinese hamster ovary cell capable of growing in culture and capable of expressing a RNA of interest or a protein of interest. Commonly used CHO cells for large-scale industrial production are often engineered to improve their characteristics in the production process, or to facilitate selection of recombinant cells. Such engineering includes, but is not limited to increasing apoptosis resistance, reducing autophagy, increasing cell proliferation, altered expression of cell-cycle regulating proteins, chaperone engineering, engineering of the unfolded protein response (UPR), engineering of secretion pathways and metabolic engineering.

Preferably, CHO cells that allow for efficient cell line development processes are metabolically engineered, such as by glutamine synthetase (GS) knockout and/or dihydrofolate reductase (DHFR) knockout to facilitate selection with methionine sulfoximine (MSX) or methotrexate, respectively.

Preferably, the CHO cell of the invention or the CHO cell produced by the method of the invention is a CHO-DG44 cell, a CHO-K1 cell, a CHO-DXB11 cell, a CHO-S cell, a CHO glutamine synthetase (GS)-deficient cell or a derivative of any of these cells.

TABLE 2

Exemplary CHO production cell lines

| Cell line | Order Number |
|---|---|
| CHO | ECACC No. 8505302 |
| CHO wild type | ECACC 00102307 |
| CHO-K1 | ATCC CCL-61 |
|  | ECACC 85051005 |
| CHOZN ® | Merck SAFC |
|  | GS -/- and DHFR -/- |
| CHO-DUKX | ATCC CRL-9096 |
| (=CHO duk⁻, CHO/dhfr⁻⁻,CHO-DXB11) | |
| CHO-DUKX 5A-HS-MYC | ATCC CRL-9010 |
| CHO-DG44 | Urlaub G, et al., 1983. *Cell*. 33:405-412. |
| CHO Pro-5 | ATC CRL-1781 |
| CHO-S | Life Technologies A1136401; CHO-S is derived from CHO variant Tobey et al. 1962 |

CHO cells are most preferred, when being established, adapted, and completely cultivated under serum free conditions, and optionally in media, which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), serum-free CHO Medium (Sigma), and protein-free CHO Medium (Sigma) are exemplary appropriate nutrient solutions. Any of the media may be supplemented as necessary with a variety of compounds, non-limiting examples of which are recombinant hormones and/or other recombinant growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. For the growth and selection of genetically modified cells expressing a selectable gene a suitable selection agent is added to the culture medium.

Protein Production

In one embodiment, the CHO cell of the invention or the CHO cell produced by the method of the invention is be used for the production of a protein of interest. The protein of interest is produced by culturing the CHO cells of the invention for a period of time sufficient to allow for expression of the antibody molecule in the host cells. Following expression, the protein of interest is harvested and may be purified. Preferably, the protein of interest is recovered from the culture medium as a secreted protein and purified using techniques well known in the art.

By way of example, state-of-the art purification methods useful for obtaining the recombinant secreted therapeutic protein of the invention include, as a first step, removal of cells and/or particulate cell debris from the culture medium or lysate. The secreted therapeutic protein is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. Antibodies or Fc-fusion proteins, e.g., may be purified by standard protein A chromatography, e.g., using protein A spin columns (GE Healthcare). Protein purity may be verified by reducing SDS PAGE and protein concentrations may be determined by measuring absorbance at 280 nm and utilizing the protein specific extinction coefficient. Finally, the purified recombinant secreted therapeutic protein may be dried, e.g. lyophilized.

In one embodiment, the CHO cell of the invention is used to produce a protein of interest at high yield. Such production at high yield can result from high cell density, or high cell viability. It can also result from high specific cell productivity. However, the skilled person will understand that having high cell density or cell viability only supports a high total yield of the protein of interest in case the specific cell productivity is not substantially affected or even improved. Likewise, having high specific cell productivity only supports a high total yield of the secreted recombinant therapeutic protein in case the cell density or cell viability is not substantially affected or even improved. Production at high yield thus refers to a high degree of overall productivity of the cell culture, typically measured as a concentration (titer), such as mg/mL. The production of the protein of interest according to the invention is high, if being enhanced by at least 10%, at least 20%, at least 30%, at least 40%, at least 50%, at least 75%, at least 100% or at least 200%, compared to a control CHO cell, i.e., a CHO cell comprising the same heterologous polynucleotides randomly integrated into the genome, preferably in preferably in a CHO cell pool without clonal selection.

EXAMPLES

The integration locus was identified by evaluating gene expression data. The gene S100A6, encoding a calcium binding protein, was found to be highly expressed across all experimental conditions and can therefore be used as a marker for a genomic locus supporting high heterologous protein expression. S100A6 is part of a cluster of S100 genes; hence the entire cluster was assessed.

Cell Selection and Maintenance

A proprietary medium was used for the routine passaging of CHO-DG44 cells prior to complementation with an active DHFR cassette. An MTX comprising selection medium was used after transfection to enrich cells which received DHFR expression cassette integration. For CHOZN GS cell lines the commercially available medium CD Fusion (Sigma Aldrich) was used, supplemented with 850 mg/l L-Gln (6 mM). Cell lines were passaged in TPP shaker tubes at 0.3e6 cells/ml on a 2-2-3 (CHO-DG44) or 0.6e6 cells/ml on a 2-2 (CHOZN GS-/-) passaging schedule per week, respectively. Cultures were counted on an automated Vicell instrument.

All of the pools went through metabolic selection by removing hypoxanthine thymidine (HT) supplement from the CHO-DG44 cell line (DHFR-/-) or removing L-Gln from the CHOZN GS cell line (GS-/-). Selection was applied after the transfection process to select against parental cells that did not receive the DHFR or GS donors. Pools that have gone through the selection process were maintained in selection media permanently. When performing selection the cells were seeded at 0.4e6 cells/per ml in a T75 static flask in a total of 10-12 ml. The selection media was normally changed after 7 days by spinning down the whole flask and re-suspending the cells in the same volume of fresh media. When the selected cells "recovered" and resumed growing they were scaled up into TPP tubes as appropriate. The cells were maintained in selection media permanently prior to performance assessment in fed batch.

ZFN Technology for Targeted Integration

The commercially available CompoZr Zinc Finger Nucleases (ZFNs) from SAFC was used for targeted integration according to assay instruction. The respective ZFNs were custom made by SAFC based on the respective target sequence information provided, e.g., of SEQ ID NO: 11 (ZFN 13).

The ZFN nucleotide sequence was unique for each ZFN arm and was linked to a FokI domain. The DNA encoding the ZNF arms was cloned into a pVAX plasmid backbone. The plasmid also contained a GFP or RFP reporter cassette upstream of the ZFN sequence, linked by a 2A peptide for separation during translation. The ZFN arms were transfected as mRNAs. For in-vitro transcription of DNA coded ZFNs into RNA the mMessage mMachine T7 Ultra kit (Ambion) was used according to the manufacturer's instructions. Thus, of the two mRNAs used for transfection one encoded a ZNF arm specific for a sequence (e.g., ZNF13) and GFP and the other encoded a ZNF arm targeting the complementary sequence and RFP. GFP or RFP were expressed in conjunction with transfection of the ZFN arms in order to allow for quick and easy enrichment of the transfected pools by flow cytometry. Cells that have received both ZFN arms were GFP and RFP positive. These double positive cells were collected in order to create a pool enriched for ZFN activity.

Transfection Protocol

For transfection a Bio-Rad Gene Pulser for electroporation was used. 1e6 cells in 2 mm cuvettes were transfected using ~20 ug of total DNA and/or mRNA (settings: 115V, 950 uF, ∞ Resistance). The ZFNs are always transfected as mRNA and the donor plasmids containing the protein of interest were transfected as DNA. Cells are transfected and cultured in the same medium. Following transfection cells were cultured for 2-3 weeks to allow for washout of any transient plasmid.

Cel I Assay—ZFN Activity

To measure the cleavage efficiency of ZFNs in the cell, the CEL-I or SURVEYOR nuclease assay was performed. In brief the target region was PCR amplified using genomic DNA purified from the transfected pool as the template. In the presence of active ZFNs, the genomic DNA is converted to a mixture of wild-type and NHEJ products (insertions or deletions at the target site). The PCR product was denatured under high temperatures and allowed to hybridize by gradually lowering the temperature. Some wild-type and NHEJ products hybridize to form double strand DNA with mismatches around the cleavage site, which can be cleaved by an enzyme called CEL-I or SURVEYOR resulting in cleavage products that can be separated and visualized by electrophoresis.

Junction PCR (jPCR)

jPCR was used to identify sequence integration into the genome. The primers were designed to amplify the 5' or 3' ends of the donor molecule at the border of the flanking genomic DNA sequence. One primer is specific to the genomic sequence near the ZFN cut site and the second primer is specific to the donor sequence. In case the donor DNA has integrated in the correct orientation at the specified locus a PCR product is obtained. jPCR can create non-specific bands especially in pools with a combination of TI and RI events. Furthermore, the TI donors can integrate in either orientation relative to the genomic loci. Unless otherwise noted, the jPCR was performed using primers which screen for donors that have integrated cleanly in the forward orientation. The resulting TI jPCR bands were routinely confirmed by sequencing. Parental cell line gDNA and/or donor DNA was used as negative controls.

FACS Enrichment of IgG Expressing Cells

Flow Cytometry or Fluorescence Activated Cell Sorting (FACS) was used to enrich for certain sub-populations of cells using a FACS Aria III instrument. Typically cells were sorted for IgG expressing and GFP-negative cells, removing non-expressing cells and GFP expressing cells. Cells were prepared for FACS by spinning down and re-suspending the cells in PBS. For IgG detection cells were incubated with a fluorescently labelled anti-IgG antibody 30 min prior to sorting. A R-Phycoerythrin labelled antibody was used to bind any cells with surface bound IgG.

Productivity/Titer

FACS enriched pools were assessed in a 7 or 13d fed-batch for CHO DG44 or CHOZN GS cells, respectively. The production run and titer assessment for CHO DG44 derived pools was performed with a proprietary basal medium and feed. The production CHOZN GS runs were performed in CD Fusion supplemented with Ex-Cell® CHOZN® Platform Feed. Product concentration was analysed via ForteBio Octet.

Example 1

CHO production cell clones are commonly obtained by randomly integrating heterologous polynucleotides into the host cell genome of CHO cells, i.e. by random integration (RI). Positional effects result in highly heterogeneous cell populations that consist mostly of low producer cells and only a small subpopulation of high producer cells. Additionally, high producer cells tend to be outgrown by low producer cells. To evaluate the potential of the Chinese hamster S100A gene cluster as a site for reliable, high level production of heterologous proteins (i.e. a "hot spot"), a polynucleotide encoding an IgG antibody was stably integrated into the genome of CHO-DG44 and CHOZN GS cells using a zinc finger nuclease pair engineered to be specific for a DNA sequence of SEQ ID NO: 11 (ZFN 13) as described above.

After confirming the ZFN activity and preparing donor plasmids the cells were co-transfected with the non-linearized plasmid containing the expression cassette encoding the IgG antibody and the target specific ZFN 13 pair by electroporation. Thus, the donor plasmid encoding the IgG protein of interest is being linearized randomly or via homologous recombination. Cells were cold shocked for 48 hours at 30° C. to improve ZFN mRNA latency and cutting efficiency. On day four or five after electroporation, genomic DNA was harvested to perform a mismatch-specific nuclease assay, Cel I assay, to confirm ZFN activity.

Following transfection the cells were cultured for 10 to 12 days before sorting to allow for complete washout of any transiently transfected donor plasmid. CHO cells were harvested by centrifugation and re-seeded in medium for metabolic selection, for CHOZN GS cells in a medium lacking L-glutamine and for CHO-DG44 cells in a medium without hypoxanthine and thymidine supplement (HT supplement). The cultures began to recover within 5-10 days. As a control, mock cultures were transfected without plasmid and cultured in parallel. The control cultures did not exhibit growth in any experiment.

Following the metabolic selection process, the cells were sorted based on GFP and IgG expression, using fluorescence-activated cell sorting (FACS) on a FACS Aria III Instrument (BD Biosciences). For IgG detection cells were incubated with a fluorescently labelled anti-IgG antibody 30 min prior to sorting. A R-Phycoerythrin labelled antibody was used to bind any cells with surface bound IgG. CHO cells were sorted into a GFP expressing population (GFP+) and a population with no GFP expression (GFP−). The donor plasmid expressing the antibody flanked by homology arms for targeted integration further contained an expression cassette encoding GFP located outside the homology arms. GFP expression was therefore associated with random integration events and the GFP negative population was enriched for cells where targeted integration occurred. The distribution and percentage of GFP+ vs GFP− cells was a good indicator for the efficiency of targeted integration and also for any positive or deleterious phenotypes at the targeted integration site. For metabolic selection, the GFP negative cell pool and the GFP positive cell pool were each cultured in 30 mL TPP tubes with a basic feed and glucose strategy. The cultures were monitored for viable cell density (VCD), viability and medium glucose levels. IgG titers in diluted supernatants were determined by direct measurement of antibody interaction using a ForteBio Octet system (Pall Biosciences) with previously established standard curves.

Titers from CHO pools obtained by targeted integration (TI) or by random integration using the same polynucleotide encoding an IgG antibody for integration were measured after 3 to 7 days in batch culture for CHO-DG44 cells (FIG. 1A) and after 8 to 10 days for CHOZN GS cells (FIG. 1B). Titers from CHO-DG44 pools obtained by targeted integration were at least 7 fold higher than titers from CHO pool obtained by random integration titers (FIG. 1A), suggesting the region upstream of the S100A3/A4/A5/A6 gene cluster is a hotspot for heterologous polynucleotide integration. Similar results were obtained for CHOZN GS cells showing at least 8 fold higher IgG titers in targeted integrated compared to random integrated cells.

Example 2

Random integration leads to cell pools that are highly heterogeneous in their expression of a heterologous protein. To evaluate if the targeted integration within the Chinese hamster S100A gene cluster leads to more homogenous expression levels and thus to a higher degree of predictability in terms of productivity, individual clones were selected from the TI cell pool and the RI cell pool of Example 1.

Targeted integration and random integration pools of the CHOZN GS cells from Example 1 were used to obtain single cell clones (SCC). The process of single cloning was done by limiting dilution of the enriched TI and RI pools using conditioned medium. Conditioned medium was prepared by culturing cells in a TPP tube at 0.3e6 cells/ml for 48 hours. Cells were sedimented and the conditioned medium was sterile filtered. The seeding was done in an 80:20 mix of cloning media (SAFC fusion platform) and conditioned media using the following steps. Step 1: Serial dilution to less than 1 cell/well were deposited in 96 well plates (200 µl per well). Step 2: Cells were incubated at normal conditions and allowed to grow out for 6-7 days. Step 3: Plates were screened for single colonies of outgrowth. Wells were fed with 20 µl of fresh selection medium. Step 4: Cells were cultured for about 14 days to become confluent in the 96 well plates. The cells were scaled up to a 24 well plate or harvested as needed. Step 5: gDNA for clone screening was obtained at the 96 well stage, if desired. A certain volume of cells was removed from the 96 wells and harvested using Quick Extract for subsequent PCR and sequencing. The remaining cells continued to grow out and were optionally scaled up as described in step 4. Step 6: The desired clonal populations was scaled up to TPP tubes and used for performance assessment.

CHOZN GS single cell clones from random or targeted integration were assessed for protein production following cultivation for 8d in a fed-batch mode before and after 60 passages. The production runs were performed in CD Fusion supplemented with Ex-Cell® CHOZN® Platform Feed. Product concentration was analysed via ForteBio Octet and data were pooled from the same clone before and after 60 passages (n=2 each, total n=4).

Figure 2:
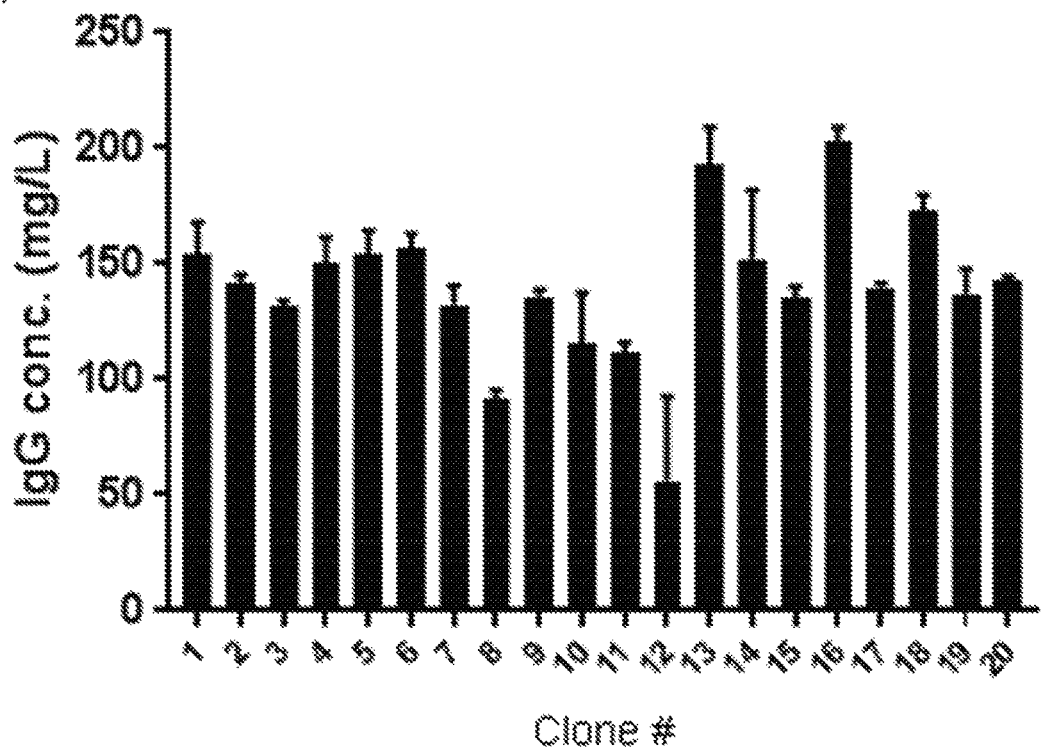
FIG. 2: Productivity assessment of independent single CHOZN GS clones for homogeneity of antibody production following (A) targeted integration via ZFN or (B) random integration. Shown are 20-24 independent clones, which were obtained via limiting dilution following the respective transfection protocol (TI or RI, respectively). Cells were passaged over 60 days in TTP tubes. The bars represent pooled data from IgG titers in µg/ml of individual clones in fed-batch cultures after 8 days following 0 (n=2) and 60 days (n=2) of passaging. Error bars indicate stability of clones passaged for 0 to 60 days. Targeted integration downstream of the S100A3/A4/A5/A6 main gene cluster using ZNF 13 resulted in more homogenous clonal IgG expression levels and more stable expression over 60 days in culture of the single clones.
Figure 2:
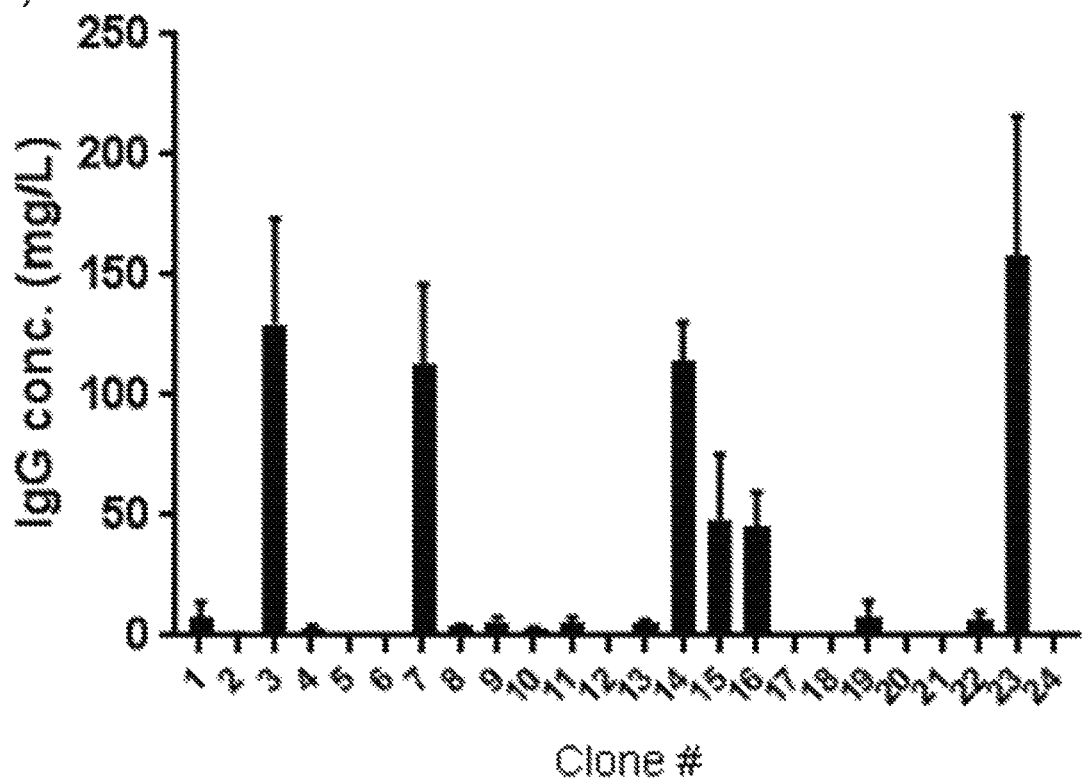

The analysis shows that single clones from populations with targeted integration exhibited highly homogeneous titers (FIG. 2A) compared to single clones from populations with random integration (FIG. 2B), showing that targeted integration within the S100A gene cluster resulted in predictable protein productivity. The targeted integrated clones was further more stable as reflected by the smaller error bars of the pooled data from the same clone before and after 60 passages.

Example 3

Figure 3:
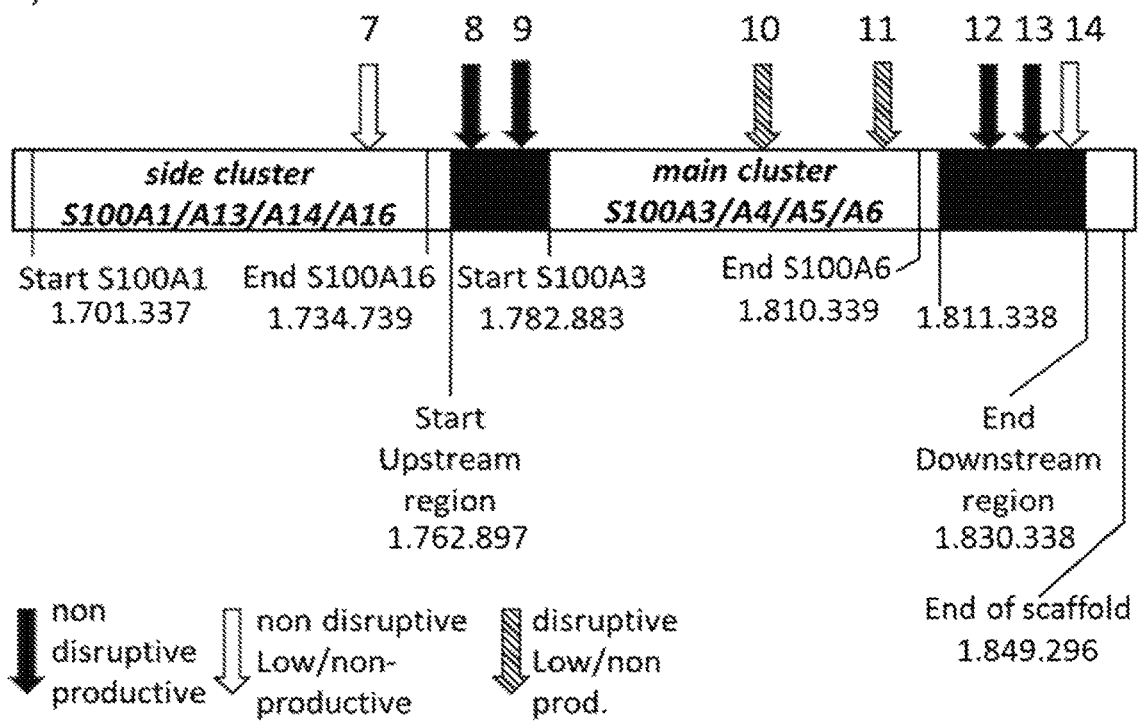
FIG. 3: Effect of integration site on antibody pool titers after TI. (A) Illustration of the location of individual ZFNs and hot spot loci in the S100A gene cluster. Numbers indicate boundaries based on the *Cricetulus griseus* scaffold of CHOZN GS cells having the NCBI Reference Sequence: NW_003613854.1. The arrows indicate the integration site of ZNFs 7 to 14 and are classified into "non disruptive and productive" (black), "non disruptive and low/non-productive" (white) and "disruptive and low/non-productive" (shaded). (B) IgG titers in mg/l are shown for CHO pools obtained using ZNFs 7 to 14 mediating integration into different loci as indicated on the X-axis.
Figure 3:
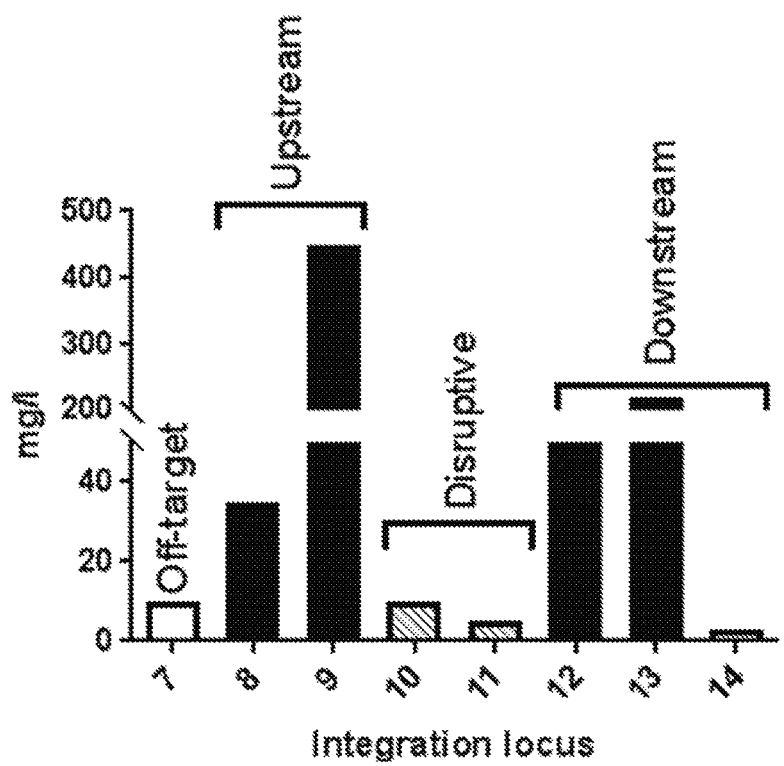

In order to validate the hot spot locus in the S100A gene cluster, a number of additional zinc finger nucleases for TI were designed and generated as shown in Table 3 to create productive pools as described in Example 1. FIG. 3A shows the location of individual ZFNs and hot spot loci in the S100A gene cluster having the NCBI Reference Sequence: NW_003613854.1. Shown are the integration sites of ZNFs 7 to 14 which are classified into "non disruptive and productive", "non disruptive and low/non-productive" and "disruptive and low/non-productive" sites.

Data was generated using CHO-ZN GS cells as described in Example 1. Eight different genomic loci were tested to evaluate whether a certain region relative to the S100A3/A4/A5/A6 main gene cluster is advantageous for the production of a heterologous gene product. It was further tested whether integration into the S100A3/A4/A5/A6 main gene cluster would lead to reduced productivity as predicted (FIG. 3B).

TABLE 3

| Zinc finger nuclease | Targeted sequence | SEQ ID NO: |
|---|---|---|
| ZFN 7 | tttgcttactgcccaggttctg agggaccacctggggctag | SEQ ID NO: 5 |
| ZFN 8 | cagttccctcttctgcaatatt ctctagctttagatgcagaa | SEQ ID NO: 6 |
| ZFN 9 | agcaactgctgtcgctcagagc ttgggaggggtggatggac | SEQ ID NO: 7 |
| ZFN 10 | ccgcgcccaatgctgggagggg gaagaacgggccagagcctg | SEQ ID NO: 8 |
| ZFN 11 | ctgggctgcctgcacctgtgtt ggctaaggctagctggttcag | SEQ ID NO: 9 |
| ZFN 12 | agcagcatctgtttccataaag tggtcaggccccaggtgggg | SEQ ID NO: 10 |
| ZFN 13 | cacaaactgaccctatgaaagt gttcagtaattcagtgccgag | SEQ ID NO: 11 |
| ZFN 14 | ggcttctactgctccagctgag cctgccctgcagtggggagg | SEQ ID NO: 12 |

An off-target ZFN (7) integrating into the side cluster S100A1/A13/A14/A16 (comprising the nucleotide sequence of SEQ ID NO: 3) was expected to have lower expression levels, despite not interrupting any gene, due to being outside of the hotspot. Disruptive ZFNs (10, 11) integrating into the S100A3/A4/A5/A6 main gene cluster (comprising the nucleotide sequence of SEQ ID NO: 4) may damage the endogenous genes and were therefore predicted to either reduce overall achievable titers or to reduce viability. Upstream ZFNs (8 and 9) integrating into the upstream region having the nucleotide sequence of SEQ ID NO: 1 and downstream ZFNs (12, 13, 14) integrating into the downstream region having the nucleotide sequence of SEQ ID NO: 2 were expected to yield the best titers, however it was expected there may be an optimal distance from the main cluster to support protein expression.

To obtain individual cell populations, CHO cells were transfected with donor plasmid and selected as described in Example 1 using the ZFNs as disclosed in Table 3. The antibody produced was the same as in Example 1. Titers of CHO pools were measured in the supernatant after 8 days of culture as described above.

The actual titers resulting from targeted integration at the respective loci are shown in FIG. 3A. Off-target TI and disruptive TI (ZFNs, 7, 10, 11) did not support protein expression. Both upstream and downstream TI pools resulted in antibody titers, however, there were differences observed indicating optimal integration distances in relation to the S100A3/A4/A5/A6 main gene cluster. ZFN pair 8 supported good protein productivity, but the ZFN pair 9 site in the upstream integration region, resulted in the highest pool titers, reaching almost 0.5 g/l. The downstream ZFNs pair 13 and pair 12 both showed good protein productivity, but the more distant pair 13 relative to the S100A3/A4/A5/A6 main gene cluster showed higher titers. Further ZFN pair 14 seemed to be too far away to support adequate productivity. In conclusion, the titers showed that targeted integration disrupting genes within the S100A3/A4/A5/A6 main gene cluster or targeted outside the immediate vicinity of the S100A3/A4/A5/A6 main gene cluster resulted in low IgG production of the resulting cell populations, while integration into the region upstream and downstream of the S100A3/A4/A5/A6 main gene cluster resulted in high IgG production of the resulting cell populations. This confirms that the S100A3/A4/A5/A6 main gene cluster is a suitable genomic target region supporting high level and reliable protein production for integration sites within genomic target regions in close distance upstream or downstream of the S100A3/A4/A5/A6 protein coding genes.

Example 4

For better applicability and easier integration of target sequences, cells may be provided comprising a "landing pad" as a replacement, such as a marker gene, at the desired location, which may be simply exchanged against the target sequence using, e.g., site directed recombination technology such as Flp-FRT recombination or Cre-lox recombination.

A proprietary CHO-K1 GS cell line was used for the FRT-mediated retargeting of ZFN Locus 13 (SEQ. ID NO: 11) (landing pad approach). The respective FRT-flanked construct (see FIG. 4A) was inserted using ZFN technology analogous to the method described in Example 1. Slight adaptions to meet CHO-K1 GS demands were applied to the protocol. The FRT-landing pad construct contained FRT-sites flanking a cassette containing a neomycin resistance gene, an RES sequence and the cytosine deaminase gene (see FIG. 4A). The landing pad was further flanked by an upstream and a downstream homology arm (SEQ ID NO: 13 and SEQ ID NO: 14, respectively) and the linearized construct was co-transfected together with the ZFN pair specific for locus 13 (SEQ. ID NO: 11). Correct integration was confirmed as described above and the landing pad was re-targeted (substituted) via Recombinase mediated cassette exchange (RMCE) by a gene of interest containing vector as described in the following. For routine cell culture a proprietary medium was used, supplemented with 850 mg/l L-Gln (6 mM). For maintenance of the landing pad cells 100 µg/mL G418 was used in addition.

The donor sequence for exchange with the pre-integrated landing pad contained an expression cassette coding for an IgG antibody and an expression cassette coding for hygromycin. The cells stably transfected with the landing pad construct were seeded at $0.5 \times 10^6$ cells/ml 24 h prior to transfection. At the day of transfection the density of the cell culture was adjusted to $6 \times 10^6$ cells/ml in fresh medium. 8 µg of total DNA (target vector and FLP-recombinase expressing plasmid) was diluted in CHO-S-SFMII Medium (Thermo Fisher) supplemented with L-Gln. As transfection agent PEIpro (Polyplus) was used according to the manufacturer's manual. Following transfection the culture was kept for 24 h at 30° C. and 5% $CO_2$. After 24 h the temperature was switched to 36.5° C. and cultured for another 48 hours. Following transfection and selection with hygromycin only RMCE events survived. The pools were screened by junction PCR (jPCR) to confirm events in which the IgG donor has integrated into the landing pad as described above.

Figure 4:
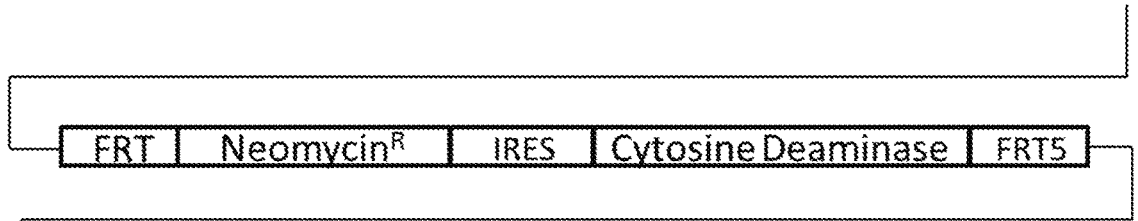
FIG. 4: Targeted integration via landing pad in CHO-K1 GS cells. (A) Schematic illustration of a DNA construct integrated into the CHO genome via ZFN for site specific integration of a landing pad for ZFN locus 13 (SEQ ID NO: 11) comprising homology arms (SEQ ID NOs: 13 and 14), flippase recognition target (FRT) sites FRT and FRT5 and two selection markers separated by an RES sequence. (B) Shown are IgG1 antibody concentrations from targeted integrated CHOZN GS cell pools.
Figure 4:
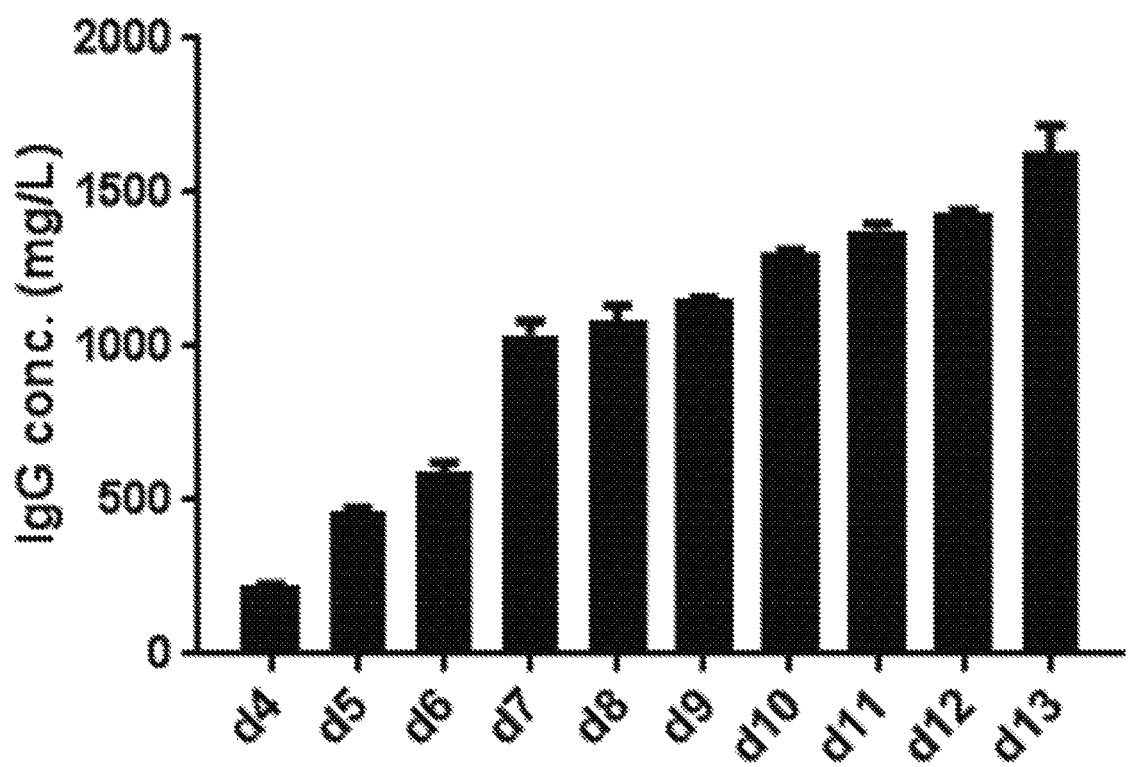

CHO-K1 GS FRT re-targeted pools were cultured for 13 days (fed-batch) using proprietary media. Product concentrations was analysed via FortéBio Octet (Bio-Layer Interferometry (BLI) as described before. As shown in FIG. 4B, IgG concentrations were increasing over time and at a very high level.

Example 5

Figure 5:
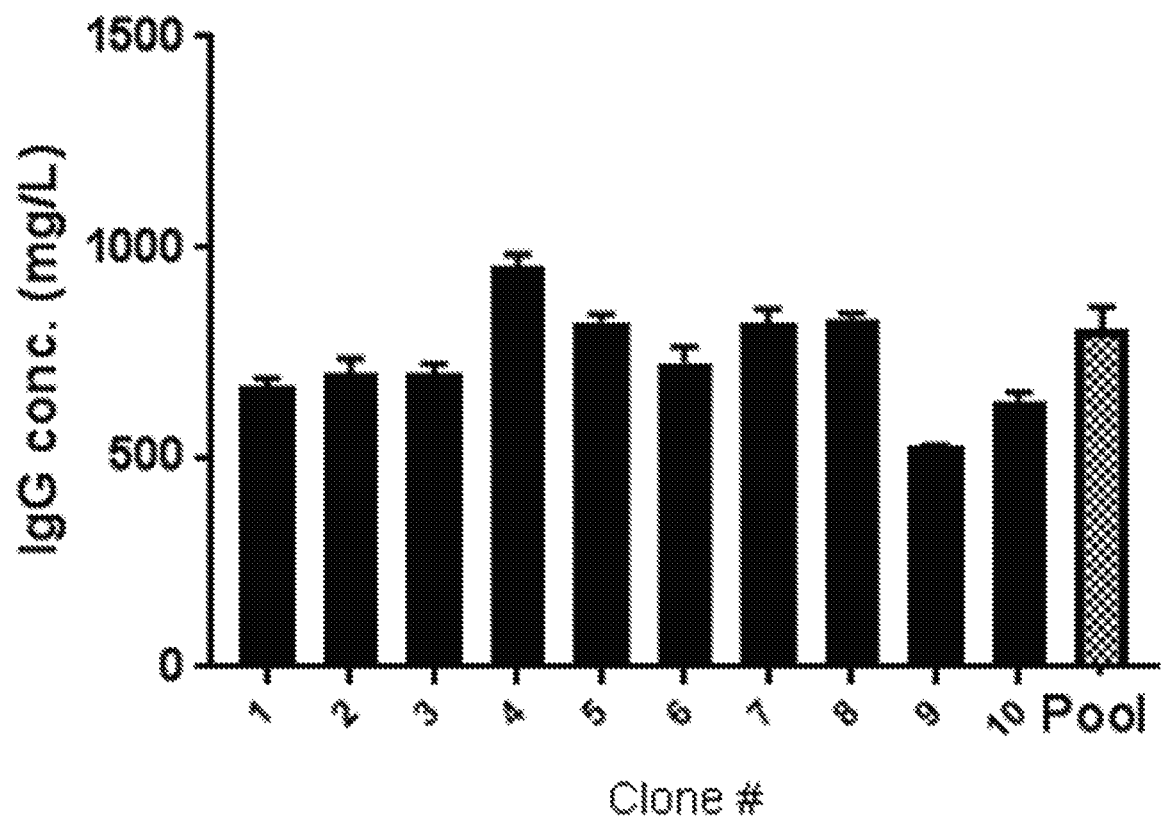
FIG. 5: Productivity assessment of independent CHO-K1 GS single clones for antibody production following targeted integration via landing pad. Shown are IgG antibody concentrations of 10 independent single clones (black bars) and IgG antibody concentration (shaded) of the cell pool.

The IgG expressing FRT targeted cells generated in Example 4 showed high homogeneity on a single clone level (FIG. 5). CHO-K1 GS FRT re-targeted pools were created as described in Example 4. The process of single cell cloning was done by limiting dilution according to Example 2 with slight adaptions to the CHO-K1 GS cell line.

Single-cell clones from CHO-K1 GS FRT re-targeted pools (Example 4) were cultured for 11 days in fed-batch mode using proprietary media. CHO-K1 GS cells were grown in shake flasks at 110 rpm, 36.5° C. and 5% $CO_2$. The cell lines were passaged in TPP shaker tubes at $0.3 \times 10^6$ cells/ml. Cultures are counted on automated Vi-Cell (Beckman Coulter) or Cedex Hi-Res (Roche Innovatis) instruments. As a control the respective pool was co-cultivated. Product concentration was analysed via FortéBio Octet (Bio-Layer Interferometry (BLI).

The invention is encompassed by the following items:

1. A Chinese hamster ovary (CHO) cell, comprising at least one heterologous polynucleotide, stably integrated into the S100A gene cluster of the CHO cell genome, wherein
    a) the at least one heterologous polynucleotide is integrated upstream of the S100A3/A4/A5/A6 main gene cluster, into a genomic target region corresponding to the sequence of SEQ ID NO: 1; and/or
    b) the at least one heterologous polynucleotide is integrated downstream of the S100A3/A4/A5/A6 main gene cluster, into a genomic target region corresponding to the sequence of nucleotides 1 to 15,120 of SEQ ID NO: 2.

2. The CHO cell of item 1, wherein
    a) the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or
    b) the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

3. The CHO cell of item 1 or 2, wherein
    a) the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or
    b) the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2.

4. The CHO cell of any one of items 1 to 3, wherein
   a) the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1; and/or
   b) the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

5. The CHO cell of any one of the preceding items, wherein the at least one heterologous polynucleotide is stably integrated into the CHO cell genome as part of an expression cassette.

6. The CHO cell of any one of the preceding items, wherein the at least one heterologous polynucleotide codes for a RNA and/or a protein.

7. The CHO cell of item 6, wherein the RNA is a mRNA, a miRNA or a shRNA.

8. The CHO cell of item 6, wherein the at least one heterologous polynucleotide codes for a therapeutic protein, preferably a therapeutic protein selected from the group consisting of an antibody, a fusion protein, a cytokine and a growth factor.

9. The CHO cell of item 6, wherein the at least one heterologous polynucleotide is a marker gene selected from the group consisting of a reporter gene and a selection marker gene.

10. The CHO cell of item 9, wherein the marker gene is stably integrated into the CHO cell genome as part of an expression cassette and the expression cassette is flanked by recognition sites for a site specific recombinase or a sequence specific DNA editing enzyme.

11. The CHO cell of any one of the preceding items, wherein the CHO cell is a CHO-DG44 cell, a CHO-K1 cell, a CHO-DXB11 cell, a CHO-S cell, a CHO glutamine synthetase (GS)-deficient cell or a derivative of any of these cells.

12. The CHO cell of any of the preceding items, wherein the genomic target region consists of any one of the sequences according to claims 1 to 11 or a sequence having at least 80% sequence identity thereto.

13. The CHO cell of any one of the preceding items wherein the at least one heterologous polynucleotide is stably integrated into one or both alleles of the S100A gene cluster of the CHO cell genome.

14. A method for the production of a CHO cell, comprising the steps of
   a) providing a CHO cell;
   b) introducing a heterologous polynucleotide into said CHO cell, wherein the heterologous polynucleotide is stably integrated into the S100A gene cluster of the CHO cell genome, wherein
      i) said heterologous polynucleotide is integrated upstream of the S100A3/A4/A5/A6 main gene cluster, into a genomic target region corresponding to the sequence of SEQ ID NO: 1; and/or
      ii) said heterologous polynucleotide is integrated downstream of the S100A3/A4/A5/A6 main gene cluster, into a genomic target region corresponding to the sequence of nucleotides 1 to 15,120 of SEQ ID NO: 2.

15. The method of item 14, wherein
   a) the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or
   b) the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

16. The method of item 14 or 15, wherein
   a) the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or
   b) the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2.

17. The method of any one of items 14 to 16, wherein
   a) the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1, nucleotides 17,100 to 18,380 of SEQ ID NO: 1; and/or
   b) the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

18. The method of any one of items 14 to 17, wherein the at least one heterologous polynucleotide is stably integrated into the CHO cell genome as part of an expression cassette.

19. The method of item 18, wherein the expression cassette is flanked by recognition sites for a site specific recombinase or a sequence specific DNA editing enzyme.

20. The method of any one of items 14 to 19, wherein the at least one heterologous polynucleotide codes for a RNA and/or a protein.

21. The method of item 20, wherein the RNA is a mRNA, a miRNA or a shRNA.

22. The method of item 20, wherein the at least one heterologous polynucleotide codes for a therapeutic protein, preferably a therapeutic protein selected from the group consisting of an antibody, a fusion protein, a cytokine and a growth factor.

23. The method of item 20, wherein the at least one heterologous polynucleotide is a marker gene selected from the group consisting of a reporter gene and a selection marker gene.

24. The method of item 23, wherein the marker gene is stably integrated into the CHO cell genome as part of an expression cassette and the expression cassette is flanked by recognition sites for a site specific recombinase or a sequence specific DNA editing enzyme.

25. The method of any one of items 14 to 24, wherein the heterologous polynucleotide is introduced into the CHO cell genome using
   a) a sequence specific DNA editing enzyme; or
   b) a site-specific recombinase.

26. The method of item 25, wherein
   a) the sequence specific DNA editing enzyme is a site specific nuclease, preferably selected from the group consisting of zinc finger nucleases (ZFNs), meganucleases, transcription activator-like effector nucleases (TALENs) and CRISPR associated nucleases; and/or
   b) the site specific recombinase is selected from the group consisting of lambda integrase, PhiC31 integrase, Cre, Dre and Flp.

27. The method of item 14, comprising the steps of
a) providing a CHO cell;
   aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme, wherein
      i) said heterologous polynucleotide is integrated upstream of the S100A3/A4/A5/A6 main gene cluster, into a genomic target region corresponding to the sequence of SEQ ID NO: 1; and/or
      ii) said heterologous polynucleotide is integrated downstream of the S100A3/A4/A5/A6 main gene cluster, into a genomic target region corresponding to the sequence of nucleotides 1 to 15,120 of SEQ ID NO: 2; and
b) introducing an expression cassette comprising a second heterologous polynucleotide into said CHO cell by replacing the expression cassette comprising the first heterologous polynucleotide of step aa).

28. The method of any one of items 14 to 27, wherein the CHO cell is a CHO-DG44 cell, a CHO-K1 cell, a CHO-DXB11 cell, a CHO-S cell, a CHO glutamine synthetase (GS)-deficient cell or a derivative of any of these cells.

29. A method for the production of a protein of interest in a CHO cell comprising
a) providing the CHO cell of any one of claims 1 to 13;
b) culturing the CHO cell of step a) in a cell culture medium at conditions allowing production of the protein of interest;
c) harvesting the protein of interest, and
d) optionally purifying the protein of interest.

30. Use of the CHO cell of any one of items 1 to 13 for producing a protein of interest at high yield.

SEQUENCE TABLE

SEQ ID NO: 1_Upstream integration locus
SEQ ID NO: 2_Downstream integration locus
SEQ ID NO: 3_Upstream side cluster
SEQ ID NO: 4_Main cluster coding area
SEQ ID NO: 5_Recognition site for ZFN 7
SEQ ID NO: 6_Recognition site for ZFN 8
SEQ ID NO: 7_Recognition site for ZFN 9
SEQ ID NO: 8_Recognition site for ZFN 10
SEQ ID NO: 9_Recognition site for ZFN 11
SEQ ID NO: 10_Recognition site for ZFN 12
SEQ ID NO: 11_Recognition site for ZFN 13
SEQ ID NO: 12_Recognition site for ZFN 14
SEQ ID NO: 13_upstream homology arm landing pad
SEQ ID NO: 14_downstream homology arm landing pad

The invention claimed is:

1. A Chinese hamster ovary (CHO) cell, comprising at least one heterologous polynucleotide stably integrated into the S100A gene cluster of the CHO cell genome, wherein:
the at least one heterologous polynucleotide is integrated upstream of the S100A3/A4/A5/A6 main gene cluster, into an upstream genomic target region corresponding to the sequence of SEQ ID NO: 1.

2. The CHO cell of claim 1, wherein:
the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1.

3. The CHO cell of claim 1, wherein the at least one heterologous polynucleotide is stably integrated into the CHO cell genome as part of an expression cassette.

4. The CHO cell of claim 3, wherein the at least one heterologous polynucleotide comprises a marker gene selected from a reporter gene and a selection marker gene, wherein the marker gene is stably integrated into the CHO cell genome as part of an expression cassette and the expression cassette is flanked by recognition sites for a site specific recombinase or a sequence specific DNA editing enzyme.

5. The CHO cell of claim 1, wherein the at least one heterologous polynucleotide is stably integrated into one or both alleles of the S100A gene cluster of the CHO cell genome.

6. A method for the production of a CHO cell, comprising the steps of
  a) providing a CHO cell; and
  b) introducing at least one heterologous polynucleotide into said CHO cell, wherein the at least one heterologous polynucleotide is stably integrated into the S100A gene cluster of the CHO cell genome, wherein
    the at least one heterologous polynucleotide is integrated upstream of the S100A3/A4/A5/A6 main gene cluster, into an upstream genomic target region corresponding to the sequence of SEQ ID NO: 1.

7. The method of claim 6, wherein:
  the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1.

8. The method of claim 6, wherein the at least one heterologous polynucleotide is stably integrated into the CHO cell genome as part of an expression cassette, wherein the expression cassette is flanked by recognition sites for a site specific recombinase or a sequence specific DNA editing enzyme.

9. The method of claim 6, wherein the at least one heterologous polynucleotide comprises a marker gene selected from a reporter gene and a selection marker gene, wherein the marker gene is stably integrated into the CHO cell genome as part of an expression cassette and the expression cassette is flanked by recognition sites for a site specific recombinase or a sequence specific DNA editing enzyme.

10. The method of claim 6, wherein the at least one heterologous polynucleotide is introduced into the CHO cell genome comprising:
  a) a sequence specific DNA editing enzyme selected from zinc finger nucleases (ZFNs), meganucleases, transcription activator-like effector nucleases (TALENs), and CRISPR associated nucleases; or
  b) a site-specific recombinase selected from lambda integrase, PhiC31 integrase, Cre, Dre, and Flp.

11. The CHO cell of claim 1, wherein the at least one heterologous polynucleotide codes for an RNA, a protein, or an RNA and a protein.

12. The CHO cell of claim 11, wherein
  a) the at least one heterologous polynucleotide codes for an mRNA, a micro RNA (miRNA) or a small hairpin RNA (shRNA);
  b) the at least one heterologous polynucleotide codes for an antibody, a fusion protein, a cytokine or a growth factor; or
  c) the at least one heterologous polynucleotide codes for (i) an mRNA, a miRNA or a shRNA; and (ii) an antibody, a fusion protein, a cytokine or a growth factor.

13. The CHO cell of claim 1, wherein the CHO cell is a CHO-DG44 cell, a CHO-K1 cell, a CHO-DXB11 cell, a CHO-S cell, or a CHO glutamine synthetase (GS)-deficient cell.

14. The method of claim 6, wherein the step of introducing the at least one heterologous polynucleotide into the CHO cell further comprises:
  i) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme, wherein
    said first heterologous polynucleotide is integrated upstream of the S100A3/A4/A5/A6 main gene cluster, into an upstream genomic target region corresponding to the sequence of SEQ ID NO: 1;
  ii) introducing an expression cassette comprising a second heterologous polynucleotide into said CHO cell by replacing the expression cassette comprising the first heterologous polynucleotide of step i).

15. A method for the production of a protein of interest in a CHO cell comprising
  a) providing the CHO cell of claim 1;
  b) culturing the CHO cell of step a) in a cell culture medium at conditions allowing production of the protein of interest; and
  c) harvesting the protein of interest.

16. The method of claim 6, wherein the at least one heterologous polynucleotide codes for an RNA, a protein, or an RNA and a protein.

17. The method of claim 6, wherein
  a) the at least one heterologous polynucleotide codes for an mRNA, a miRNA or a shRNA;
  b) the at least one heterologous polynucleotide codes for an antibody, a fusion protein, a cytokine or a growth factor; or
  c) the at least one heterologous polynucleotide codes for (i) an mRNA, a miRNA or a shRNA; and (ii) an antibody, a fusion protein, a cytokine or a growth factor.

18. The method of claim 6, wherein the CHO cell is a CHO-DG44 cell, a CHO-K1 cell, a CHO-DXB11 cell, a CHO-S cell, or a CHO glutamine synthetase (GS)-deficient cell.

19. The method of claim 15, further comprising purifying the protein of interest.

* * * * *

UNITED STATES PATENT AND TRADEMARK OFFICE
CERTIFICATE OF CORRECTION

PATENT NO. : 11,560,549 B2
APPLICATION NO. : 16/637914
DATED : January 24, 2023
INVENTOR(S) : Markus Mueller et al.

It is certified that error appears in the above-identified patent and that said Letters Patent is hereby corrected as shown below:

In the Claims

In Claim 12 at Column 105, Line 56, insert -- short hairpin RNA; -- before "shRNA);"

Signed and Sealed this
Fourth Day of April, 2023

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 19987
<212> TYPE: DNA
<213> ORGANISM: Cricetulus griseus
<220> FEATURE:
<223> OTHER INFORMATION: Upstream integration locus

<400> SEQUENCE: 1
acagagaaac aagcaagaga gagatgagga ggggaccgat gttagcttta ccagttggtc      60
tggtaagaag agaaaccagg aagtggctgg tgaaggaact ttgggcaaag ctgcagagcc     120
agtgtgactg aagagtggtg ctctgcagcc tggccaacct gagttcaaat ccagctctac     180
tcttaatcta cccggcctct gtttccagat ccactcatca caggaatggc ccacattgtt     240
agagggtgtg agaggtcagg gcttcttacg ctttctcctc tcttagccac tttttgcctg     300
agaaagttat gaaaggccct gtacaggtag atattaaaat agatatatgt taaatgttca     360
cttataataa agattaattt taaaatgata ttttttgtta aaaatgaaac aatttgaata     420
ctaatgagct ggatgtgctt gtttagtttt tattcaatat cttgtttatt tatgagactg     480
taatttagtt acaatgtttc ttccttccct tttctccctt caaactctcc cttgtaccct     540
tccccactgc ttcaaatcct tggcctcttt tttgttaatt gttattgcac acacatatgt     600
atttgtatat acacatatat tcctaagcat aacttgctgg ggctgtataa tgttatttgt     660
atatatgttt tcagggctga ccatttggca ctgaacaacc agttggtgta ctcttcccca     720
ggaagggcca cttctctgct cccagcttta ctcagttgcc tgtcattctt tgtgtagggt     780
tgaggcctca tgggattaac cccatccagt ttggcatgtc aattggtgtc aaacttgttc     840
agcgcttgtt tgggcagtca tgttggtgag acgttacagg tgtagcttct gatgttacta     900
ggagacacag tctcacaaca aactctctga ttctctggct cttacaattt ccagttccct     960
cttctgcaat attctctagc tttagatgca gaagtgtttt gtagatttat ccattgggac    1020
```

```
tggattccac agctctgcat tttgactggt tgtggttttc tgtagtggtc tctgttgcaa    1080
agagaaattt ccttgatgaa aggtgaagaa tatatctgtg gttatatgaa caaatattta    1140
tagattgttg ttagggatta tgctggttta ataaattagt ggttatagat ttctcttcca    1200
ataaccacag ttttcctagc attgagtagt taggtaggat tccagtatca agcatgtttc    1260
ccctcttgtt gaatgggtct taagtccaat tacagagctg ttggttacca ccaaggtatg    1320
tgtgctgcta ctgcaccgtg gggttatcat ggcatgctgg ttgttgccgt ggttcatagg    1380
tggcatagct ggataggatt gttggttgcc tccctctttt ggaagctttc atggtgcctt    1440
ctggtaccat taaagctagt tctcagggag ggagcattta ggatatttcc agatcaaggg    1500
tctctgggac ctgtgtctga atgtttggt gtcttaagca atagggattt acctttata    1560 tcttgaggat agccaagggc aatatgctta cataaatgat tgaatcttgt ctaatatttt    1620
ttctttttga gacagggtct cactgcatgt tcctggttgg cctggaacac actacttta    1680 gatcaggctg gcctcgaact agcagagatt cacttgtctc tgcatctcaa gttgactggg    1740
attaatggtg tgtgctatca tgcccagcca atcttggctg agtatttgat actttcagga    1800
tcaagtcagc aatgcaaaca gcaatattac attttaagt gtttatta tctttatcca    1860 atcttcattt aattagttca tatattcata tattgtattt tgatcatctc caacccaaat    1920
cacctatccc attcccttta gaccctccca tattttcccc tcctctctca tatcctcttt    1980 attttaata acccactgag tccacttagt gctgcttgtg tgctcatggg tgaggggtgc    2040
tctgtgatag catgggcagc ctaccagcaa ccacccgccc tcaagagaaa agactctccc    2100
tcttccagca gccatcaact gccaaaagat cgcctgctgg gttgaagcct ctgagttcct    2160
cttgcatcca cgctgggatg ttgacgggct tgatctcctg cagataatca tagctgtgag    2220
ttcaggagtg caacagctgt gtggtgtcca gaagatagca tttcaagcat ttcctgttgt    2280
cttcctgctc ttacagtcta catccctctc ctttatgctt tctgagcctt ggtgaggaga    2340
agggaaggaa gtagtgactt gacagaaatg tcacattcat ggctgaacac tgaaaagtca    2400
tttattatca gctcttacac aagttatgag tctgctgccc agtgaaaaac gaggtttctc    2460
tgagcaaggc tgagagcagc actaatatat agggttgtga atataaatat tttgaaggca    2520
gtttgacacg tcagtttagc aaaaacagta atagttccct ccacctctac cccagggcct    2580 ataagttttcc tagacatagg cttttgatga ggtacacagt accagacata aattacctgc    2640
tgtggaccgg gcttcaaacc caatcaagtg actggttact cccataactg tcatgccact    2700
attgtatcag gagttacttc ttgctaggca gttaattgtc atagcatgca tgatccacag    2760
gtgggtaaga ccattgatag cttttcttct ctagtagcct gaatagtacc ttctgtcact    2820
ctgaaaacta gctagtaggg aggaaacttc tagatcagtt ccatttcaat ttctccatgt    2880
ttgaaccaag tgtgtgatgt ctttagaaat agcatcttac catctagttg aggtgggcaa    2940
acaagagcaa tgacaatagt ctgtgttgtt ttagggggct ctaaagcttc ccagaccaat    3000
aacgataggg acatagccta actttacat tgggattttc agttagtaac ttatgtcttc    3060
taggaacgca ctagccacct acgtaaggta cctgtgttca aactcctttt aaagttaaaa    3120
aaaagtagct tacaaagttg cgtagtccat aggcttgtgt gtgtgtgtgt gtgtgtgtgt    3180
gtgtgtgtgt gtgtgtgtgt gtttgatata gggttttact atgtatccct gactaacctg    3240
gaactcacta tgtagacctt gaagtcacag agatccaact gccttacagg tatgtgccac    3300
cacttccata gttgccataa gtttttttaa aaaatatttt ttttcatac aactgcaaga    3360
```

-continued

```
accttaacat ggtgagccgg ctcctttacc tctccctgac ctccactatt ttgtgacagg    3420
ttctcatata taccaggctg gccttgaact tacagtgtag ctgagggtga ccttgaactg    3480
agtctcctgc gtgtgctgcc acaccagttt atacagtgcc aggaactaaa accaagactg    3540
tgcacgggaa gcaagcactt tgtcaactaa actacatttc caaggccctc aaaccatgat    3600
tctttttatt gaattttatt tattattatt tttttatttg agacaggatt cctctatgta    3660
gccctgactg tcctggtact caatctgtag accaggctgg ccttgaactc agagattagc    3720
ctgcctctgc cttctgagta atggtattaa aggggcacac catcacacct ggcctcaagc    3780
agcgattctt aaaattaaat atccaaacat aacacattcc aaaaatgtac taatttgtta    3840
ctaatttgcc aaagaatgat gacaggaaaa tattaatagt ctttgttttc taggctggag    3900
agatggcttg gtaattaaaa gagcattagc tgctcttcta gaggaatgag gtccggttct    3960
cagtacccat atggcagccc atgcccacct gtaaatccag ttccagggaa tccaattttc    4020
ctctggtttc tgagggccct tgcacacacc cttccccata tatatataat taaaaataaa    4080
aacaaatctt aaaaaaatta tgtttctact agagcagaaa actttgtgta tacagtgaaa    4140
acgttgcagt tcttaacaca aaacagcctt gggcctgagg agggttttag ccagcattca    4200
ttggcgcttg gagggataat ggctcggata gtgcaaagag cttgtctgtg cccagaaccc    4260
ccaaggctgc agggaagttg tgtgacccca cccctgact cattgtgtgt tagcctttga    4320
attaatcttt ggttgtttgt tctgaaatct cttactattg ccaaagtttt gtgacactac    4380
cctccccgcc aatccagtta caccccaca tagggttgta acacagtttg aaaaaccagg    4440
aattaggtac catgtgaaca atattcaata catttaattt cttcttgcct gcttgctggc    4500 tgccttttt ccttctcaga aggaattatg tgtctgtttt aaagctgggc aggtccagat    4560
cattcttcat cacttcattc aggggtggtc ctgtcctgag agactgattg gctccctgat    4620
ccagcattcc aggaatcgat ttcatgtctt ccccaaagga aagtccctct gtgagtctag    4680
agctggtgac aaataactgg atgtgaatga tggttccccc cttatttctg agacaggacc    4740
tcattcccat attacccagg cctcgaattg accctctgat cctcctacct catgtcctgg    4800
gattacaggt ctgcaccaat agactcagag acatgagtga tcttaaaggg ccatatgagt    4860
aagcctgaca aaggcgtgtg tctctcctgg taaggaatag aattggtata ttttcttct    4920 ttctttcttt cttctttct ttcttctt cttctttct ttcttctt ctttctctct    4980 ctttttttt tgtaaagatc tatttatttt ttttaaacct ttatgtgcag gagtgctttt    5040
cgttccctgt atgtatccgt gtgcctggtg cagtacagcc cttagatcta gagacagcca    5100
attgtgagcc accatgtggg tgctggaaat taacacaggc cctttgcaag aacagccagt    5160
gctcttaacc acagagccat ctctgcagcc ctggtttctt ctttccagtg ctgcttctaa    5220
taacatgtat tggattcttg tgtatgtggc atgtgttgtc tcatttgatc tgtgggttgg    5280
gatagtattc tgctacagat gagtagagtg gtgattaccc tggtgtaaga gcacatagtg    5340
aatgtggcta ctgtgacgct tgctttcttt ctttggtaag ggaccagag tctgccttta    5400 ccacgctggg ccaatcagag tactttgtct ctctggctac ggggaggggc gggatgttgg    5460
ccaatagcag aatagctgaa ccaagcaggg ccaaccagag ttttccctg cattagtaag    5520 cagatcctag gtttatatgg ctggatgaac acatttccta tgtatgtatg tatgtatgta    5580
tgtatgtatg tatgtatgta tgtatgtatg tgcgtatgta tgcttaattc cttgtggcct    5640
ctgaagctag atcactgatt gtgtgaatta ctgcaacact ttgtaaagac aagtttgttc    5700
atttattttg agaaatgtgc ttatgtaccc cagactggca gaggcttatc tccatgtctg    5760
```

```
gatcctgcct ccatttcccc tgggtaagga gtataccact gcattatgg gatgctggag   5820 attaaaccca ggatttcttt tcttttcttt ctttcttttc ttttttagc agatttttta   5880 aatttgaatt agaaacaaga ttgttttaca taacaatccc agttcccttc tccctcccgt   5940
cctcccttaa ccccttacc cccctcccg tcctccaact aaaaccctat ctatcacata   6000
tccttaaacc ctggatttct tgaatgctgg gcaagcaggc tagcaaacta gctttgttga   6060
cacacctttc tgtgatcctg tgagtttgtc tcttagctga agtgctgaat ataaccagca   6120
gcggtaaaaa gcctgaaaga tggattcttt tggatttgca acttgatgat tggtttccca   6180
gccaatcatc ctgggagagc gggaggcagc agcactaggt cagcagacta cttatactct   6240
gtcagtaagc ccagaagcag acaggagaat gaatgggtgc tgcacccggc tctcatcctc   6300
caggcctgcc tacttccccc agctgggccc cacatcctaa aagttatata gtttccccaa   6360
acagggcaac cagatagggt caatggggac atttcctacc atcacactga ggattaaacc   6420
agggcttgtg ctcactgggc atgtactcaa ccatagcgca agatccttag acttttttt   6480 tttctttttt cttttctctt tctttctttc tttctttctt tctttctttt ttaggattca   6540
tttatttatt atatatacag tattctgctt gcatgtatac ctgcaggtca gagagggcac   6600
cagatcacat tatagatagt tgtgagctac catgtggttg ctgggaattg aattcaggac   6660
ttctggaaga cctctgaacc atctctccag ttctcttagc ttttttttt ttttaaact   6720 ttcttttattt tgaagcaggg tcttgttaaa tagatttatt tatttattta tttatttatt   6780
tatttattta tttatttagg tttctctgta gctttggaag ctgtccagga actagctctg   6840
tagacctagt taaagagcgt actccaccac ccgcctgttg ctaaattgtt cttgaatctg   6900
tggccttccc acctcagcct cctgagttgc tagatcagat tttaaaaaag attagttgta   6960
gccgggcatt ggtgtcgcac gccttaatc ccagcacacg ggaggcagag gcaggcggat   7020
ctctgtgagt tcgagaccag cctggtctac aagagctagt ccaggacag cctccaaagc   7080 cacagagaaa ccctgtctcg aaaaacaaaa acaaaacaaa acaaaacaaa aacaaaacaa   7140
aaaaaagatt agttgtattt tgaattatgt atgtgtgtgt atttgagtgg ttatatgcag   7200
gtgtatgtat gtatgtgtgt atatgcagga gtgtttgtgt atgcaggtga tgccggtgtg   7260
tgtgtgtgtg tgtgaatgta gatatgtagg tgtgtgtgtg tgtgtgtgtg tgtgtgtgtg   7320
tgtgtgtgta tgtgtaaata cacatgcaca cttgtggtgg tcagaatcag gaagcatgga   7380
atccccctgg aactggtggt tgtaagatgt ctagcatggg ggctgggaac ggaactctgg   7440
ttttctccaa gtatgggttc ttaattggct atctctgcag cccctgaaag attaaaaaca   7500
ttatggctgg gtttgtagtg tgcacctta accagcactt atgaggcaga ggcagataga   7560
cagatttctg tgtttaaagc caggttggca actggtcagc caaggctaca cggtgagact   7620
ttgtctcaat aaacaaacaa acaaacaaga atgagaataa taagataaag taagaatata   7680
ataaatgttt ttatttctgt gtgtttgagt gtgcacatgc atgtgagcac ctgccagaag   7740
aggcttctga tgtccaggag ctggagtttt aagcaatggt gagctacctg gtgcaggtgc   7800
tgggacctga actccagtcc tctgcaagag caccacaagc tctcaaccat tgagccatct   7860
cttcagcccc tgaaaggtct taattaataa aattaatgct aattattggg tcaagagtta   7920
agtccagatc caagtcttgg ctctttcact gtaactgatc tttgaaacca cttccttatg   7980
agtaacgtct taggttttaa gaacactgct cccactgagt cacctgtgtc actcctgaaa   8040
ctggctgagg tcccttctg gaatgaggaa cttcctgggt tcatgaaca caccaggaca   8100
```

```
tggctctcag gtgaccgctt ctgagaggac tgctaatcac tcatttatgt ggattcctct    8160
cagtgccagt gtcaccaagt aacagtgtcc tgagttccac tgttgttggc cctctctttt    8220
ggcaacttgg ggagcctggc ttcagcctca agcctaccta acactgaggc tttcgtactt    8280
gctaggacag cagccagcct ctggctaggg gaggccatga ggaattgaca gccagggcac    8340
agatactctg agctcttgat tcagacagca ggggtcggag ctctgaacat gagtgaggag    8400
ctgtgggatg tgggagcctg cctctagtcc tgacatctat gatgtggagg acggtgggc    8460 cagatagtag ctctgctcct ttcctgttct caggcaggga gtttaaaagg acagaggata    8520
aagaagtctg actggtttcg gtttaaagta taaaatgttc ccctttgtga caccagaatg    8580
taataaacca tcgtcctttt gtgtgtacac aggctgactc tgatatatga catggaaaac    8640
cacgttttat gggcacattg aaagaacatt cattagctca tgatgcggca ccatgatcct    8700
agctgaaagg aagtatattt tagatgctcc acccagatta atactggagt ctgtcctgcc    8760
attgcaaact gaaaaatgag aacactccga ggttttcgca tagctatgga tcatgtgtgg    8820
tgacaagtgg atgagtaatc acaaatatta ctcaagaaca aaaagattct aagagaaaat    8880
aaagcaggaa ggagacaaac tagcattctt ggagaaagaa ttgaaaaata tgcatagttg    8940
tagaatccca tagatgtgag tagggagact aatgcagcta atatactaag acagcaattt    9000
aattcttaaa tggaaataca ggctggtgtg tagctcagtg gtagagcgct tatccagcat    9060
gtgtgagact ctggcttcca tgccccaaac cacaaaagca aacatataca ggaagaaagc    9120
aggcacatct tagatgttcc acccagatta acattgcagt ctctcttgcc attacacatg    9180
gaactgagga cgagcagagg tttaggcata gttgtggagg aagcagcctc ttctagcatt    9240
ttaatggtaa ctgctataaa attatcatgt agattatttg atttgctatg tataattaaa    9300
atgcattgta attttaagac tctgacattt aaacacattt atactacttg gcaatgatgt    9360
agatcagttg ttattggact ttggatctcc agcccccaaa taatgataca gagacttatt    9420
actaattatg aaagcttggc cttagcttag ccttgtcccc aaagagctct tatagttgaa    9480
attaacctgt ttatattaat ctacattctg ccatgtagct cattacctct gctcagtacc    9540
gtatgtctga ctccatggtt aatgccacct ctcttattcc cagagttcct ctctccctgg    9600
aatccccacc tattctctcc tgcctaccta ttgaccactc agctctttgt taaatcaact    9660
agaaagtgcc ctgacagaga cacatcgtgt ccaaaaagat tatcccacag tagtcagcgg    9720
tgtttgtagg taagttgtag gtcagtggta gagtgcttgc ctagaatgta caaggtcctg    9780
ggttcaagtt ctagcactgg agggaaagag aggacaatgt ttgaataatg tctcatgcta    9840
tgaaagcatt tgctaatttg tattatttga agattctaat gagacagcta tttaatatat    9900
atattgtatt gattcattag tattagaaaa taagtctgct tttctttatg gggcacctttt    9960 tagagaaagt gcattgaata tgctatttcc caattagtat taggaagttc acttaaaaat    10020
cttctcactg ggagagatcg attagtattt caagcaagag cgcagtgact ctgacatccc    10080
ctctccctaa tctggtttgt atactgacat cactcacaat caccatttct ctgcaaattt    10140
ccagttagcc cataaaaaaa tccagtgctt cgaaagttct ttggatggtt cagcaggagt    10200
ttgaatccct caaatgtcac agcggtcttt aagcctattt ccttacaggc tgtcttcctt    10260
agcaatttaa ggaaacaaag agctgttgcc aaggaaaagt gagttggttt tgtttgtttt    10320
gttttgtgtt agatatgtgg tgttttctga tgaagtctct gacacggatg acagtgacat    10380
tggaatatgg aagtcctgta ctctgagaaa gatcacattt ctagatgatg cttttgccac    10440
tgattaactg gatctgcatg tgagtgatgg tttctaagct gtttagtgac agctgcatgt    10500
```

```
ggtgacacag ccggcaatcc tgtcacttgg gagtctgagg cagaaggatc ttgtgttgga    10560
agctgcttta ggttgcatgg tgaggtcctg ttcacaaggg aggggggcggg aacaaaaatc   10620 cagaacagaa caaaacaatc aaccaaattg tatagtaaga cagcaacatt tctcaacttc    10680
agaaacagtt ttctgagtgg cattgtgacc ctgactagga aaggctgcat ccctggagct    10740
tccttctccc cttactgtta ctctgtaacc tcgtggctaa ggcagtcttt cttcatttta    10800
tttgttcaca cttacctatc aatatgtaca cacacacaca cacacacaca cacacacaca    10860
cacacacaaa gttgggtgtc agaggacaat tgtgggaatc gcttctctcc tccccacgt     10920 ggggcccctca ggttggcagc aagctctttg acctgctgag ccttctcact agccccactt   10980
tcccatcatt ttatgtcttt aatctgcctg attctgctgt acagtgaaag gcaagcattt    11040
gacaccagcc ttctgagctt cttcaaaaaa gtgtttgttc attaagtatt cagaatttgt    11100
ttactgatta ccaagagggt gttggttatg ggagcccatt tcacaatgcc tttctctcct    11160
tttgggaatg gaacctaggt cttttctct ccaggaaaat gctctaccac tcaactacag     11220
ctaccttatt cttttatatt ttcaaggcta tttgcgtctt tagttatctt tgtcttagtt    11280
tgttgcaaag gttgctgagg aagagatgca tagggttaaa tgcagggaaa ggggtcaga    11340 gtcccatact ctagggactt ccacgtggtc atttcattgt gttctttcta atcagttttc    11400
actaggatgc aatggtggtt ttggtggtta gaggttgggg aaacaaggag tgttttttctt  11460 ttccttacct catcccctg aagaatgact caagtgaatg gttataaatg gcaacagaga     11520
gacagagaag gcaaagatct gagttttggg gtttggaggg tgctaattat tctcaccttc    11580 ttcccttga agttctgaga agaactcaag caggactccc aatcacagcc atggactaga    11640
tgatgtaatt tggagctgag gctatgttgt ggtttgaatg ttaattctct cctacaggct    11700
catttgtttg aagagttggt tcccagatgg tggcactatc ttgggagact gagagacctt    11760
ttggacttgg ggcctatta cagacttgag gatacagaag ttggcctcat agcccatcct    11820
caggtacatc atgaactctc tgcttcctgg atggtaccct atacctcatg ctcccactgc    11880 caggaaaacca cccacagtca caccttcctc tatgatggat taaatccacc ccaatcgtga   11940
aaccaaatag atccttcctc cttgaagttg tcaagggttg gttagagtga tgaggacata    12000
aagaatagag taatctgttt ctgttataga actgaccaca gcactcagga ggcagagaca    12060
gcttggtcta cagagccagt tccaggatag ccagggcagt tacacagaga aaccctgtct    12120
caacaaacaa aagcaaaaca aaaggaaacc aaaaccaaaa ccaaaccaaa ccacaacaaa    12180
aacaaactga ccatattgtt tttcggtctt tggaggtggt ttttgggagg aatgtggaga    12240
aatttagaat tgtgggctag aagctgggcg ttggtggtgc atgcctttaa tcccagcact    12300
cgggaggcag aggcagttgc atctctgtga gttcgagacc agcctggtct acaagagcta    12360
gttccaggac agcctccaaa gtcacagaga aaccctgtct cgaaaaacca aaaaaaaaa    12420 aaaaaaaaa aaaaaaatg tgggctagaa aggccctaac attctgtagt cagagcttac     12480
tgggccattc tgatgagtgt tcaggagacc atactattga tagaaaaatg gacactgttc    12540
agattcatga ggatttagag tggcagtgca tgcctatgat ccaaattctt ggaaagtgga   12600
ggcaccagga ttgggagttc aaggtcatcc ttggctacac agcaagtttg aggccagctt    12660
gaactacaca atgaagtgtc tcaaaaaaga acaatgaaaa tcaaggaaaa acaaacaaaa    12720
ccaaatacac ctaaaaacaa aacaggaact gtagcagaca ctgggttaga caccatttat    12780
gttacgttca gataaagaaa ttggttatgt gttatttcct aaaactttga gtgaagttga    12840
```

```
attcagaagc aatagagtaa tttgttctgt agagaacatt gccagatggc acagcattca    12900
ggttgtcaca tgactgttga catgtgacaa ccgttagcta tgtttacagt gaaaattctg    12960
atcagatagt ggcttgaaaa aatgtggaag atgaggccgg gtgttggtgg cgcacacctt    13020
taatcccagc actcgggagg cacacagaga aaccctgtct cgaaaaacca aaaaagaaaa    13080
aaaaaagtgg aaaatgcaca gtttaatgtg cacaggacca tgagtcaagg taaagttgca    13140
gaaagagccg ataaggtttt tttgccgaca aagtagctac aattacaaag acaggaacac    13200
aattaaggat taactatgta tgcagcttgc tttggggcag taggaatggc acattaaagg    13260
caagatctac tccctgaagg cttcagggaa taaagctgta tacctgtctg ggagcattca    13320
tttgaaagga gagggtttgc aaaggagagt gcctccactt gggggtttct tgcttgaaaa    13380
tggctgtccc tgattaagtc acacaggcac ttggatacca cagccttagt ccaagtgggt    13440
caggctacat ttcaagttgg cagtaaaaac ttggtgttat tttccgtgtg gtactggttt    13500
ggcagtcaaa caaaactcca ttcatgcaga ggccgatgga agtttgcacc aaggttatac    13560
aaagctgctg aggtcaggca atatgtaaca atgttacact ctccgcatgg agtcctggag    13620
tttgagccga ctgaatgaag ttgagcccag tttcagtggc catcccaggg gttatgagat    13680
gccagaaatt tggactttg cagggactga aaagacccag gccatgaaag agcacacatg    13740
ctacagattg cagggctgga gggatgggag tgtataaacc tgttggagcc cagaagatgc    13800
tgtcatgatc tccagatgct ggtcatggcg tgttgcagag tttggtgtct atctgtttga    13860
atttagtctt tctttagtgt ggtattcttt tgatattttc ccattccttc attttagagt    13920
gggtatgttt gtatcattgt acattgaaag tatgttactt ggttttggt tttccagggg    13980 ctcttagcta aggatttatt ttgagtctca gaagagactt tggacttctg aactatgtta    14040
gaattttaag agtacaggaa ttttttggtc tttatttact tttcactttt ttgtgatata    14100
tatatatata tgtgtgtgtg tgtgtgtatt atataaattt atataataat acacacacac    14160
acacatattt gtatgaatac acgtggaaac cagaggcaag gttgcaatgt tttcctgaat    14220
cactgtctaa cttattatct gaggcagagt ctctcactga acctagagct catccattga    14280
ctagactaac tggcaatccc taacaatcct cctgtcccct gccccccagc actaggctta    14340
catgcatgtg ttgccatacc caactatttg tatgagttct gacaattcag actcaggttc    14400
tcaggtttga gcagcaatca ctttatgaac tgagtcatcc ccccagaaac tccagtgact    14460
tttaaaattg ttctgaatag tgaacggatc ctgcatttag ggatggctat gagaccgtcc    14520
agctaggtta tggttatggt ttgggtggga actgtcttcc acaagctcat gtgtttacaa    14580
acttggtcca cagaaggtag tgctatttca gaaaactaag aaatctttag aagatgggac    14640
ctagctaaag gaagtgggtc actgggagga gttacagcat tgccccgctt ctggttgact    14700 tctttgctt ctggctgatg acatgatgta atcagtgccc aagagtcctt ctatcccaac    14760
atggagttgc tcctgttttc aggctttcct catcaccatg aactgtacta tcttgaataa    14820
tgagtcaaaa caaattcttc tctcttaatt ttcttctttt aggtatttt atcacagtca    14880 tggggaaagt aacttgtgaa ggtcaataag atctttgcag tgctttatgg gtacgcatgt    14940
ttcacctgta tgtttgtctc tgctctgtgt gtatgcagtg ctcaaggagg ccagaagagg    15000
gcactggatc tcctggaagt ggaattacag gttctggaaa cttgggtcct ctggaacaac    15060
agctagtgct gtcaactgca gaaccaccta ccatgtttca agctccaaga gctatcagtc    15120
agtcagtcag tctgtctgtc tgtctgtctg tctgagtgtc tgtctgtctg tctaaatcat    15180
ggacagttgt gtagccattt cctcagaatt taaacatccc tctaaagccc aggcagtaaa    15240
```

```
caaaaagtta catatctcag gaagctccta aaacaagatt cgcagtggtg tctccctgca    15300
ggtaaagaag cagcaaggac ttctgtggag aggagacttg ttgatttgct gagctgcctg    15360
caagcagtgc agggtgtcca atggtgctgt tccaccagtt gttaagcatg ctagggtggg    15420
cttttccata gtgcagcttt gtctgagcca tccatgctcc tgtgagtgag ttcaatacag    15480
acatttgctc accttgcccc aggaaaagtc acacctcccc acagacagaa gctgcccaac    15540
cacaggctcc aggggttgg tagaggaagg gaacagagaa gggtgccctt ctcgtgaggc    15600
tatgttggat gagaaggagc agcatctgtg ggaggggaga acagagtttt ctcatggagg    15660
tggagagggc acacgtggaa tgaattgttc cctcagaaga actcttctga ggaagggtc    15720 atcaagctgc tcccttttcca tcaaaagaag ggagtctctg gtggcactgg agagagctga    15780
tcccatggaa tggtaacaag tcagttttca gaaggttcag gggttgggta gaggactggg    15840
tgtatctgga ggtaggatag tccagggagg agagaaggat ttggctgtga gggacagcac    15900
ttgagcctac agccaccatc tagcagacac ttattttgtg ctaggcacta gggaatggag    15960
ggtttcatga agcttagcat ttatttctag tgggagagat atttaaagtc agaattaata    16020
aaaatgatgc tatagagcca tgagcaacag gctgagggac tggctgggga gcgcctaagt    16080
gtgagcatgg gcctgctcaa gcatgcaggg gacctgggaa atggatttgg ggctgaaccc    16140
agaggaaatg acctttgagg tgagctggaa gggtgattaa ggagcttgtg ctggagctgg    16200
agagatggcc taggggttaa gagcacctgg ctacttttcc agaggaccca ggttcgaaga    16260
ctcacaacag tctataaccc agtccctggg gtctgacacc attttctggt ttccttgggc    16320
actgtatgaa tgtggcacac agacatgcat acattcagat aaacactcat gcatataaca    16380
taaaataata aataaaatct tcaaaaaaaa aaaagaaag aaaggaaatc aaagaggctg    16440
atgggtggct ccactgagga aggctttcca tgagagtaca tggcatgggc agaagttcag    16500
ggtcaggaaa aagtatgacc tataccacag caaagttagt gtgtcaagaa tgggatgcca    16560
tgcctgggtc tcctaaaagt taggagaatt cactgaatgc tgtaatctga agaaatttga    16620
acttttagag ctgaggaggg gttagtgtga ggcccaggag cagggctgga ggagaatgca    16680
gctgggacag atgatttgaa agaggcctaa agcagtgtgg acagagacca gtcatgctta    16740
gaaacaagca ggctgaccag acatctggtt agcagccagg ggaagcagga ggctgggagg    16800
aagccaagcg tctggtttgg gtcacgggta gatggcaatg ttctttgtgg cacagggaa    16860 gcctggttct tccatctgtc tgcctcctga ctccatcctt gctctctgga gactttgctc    16920
agctcctttt cttggtcccc atggcaggat gtttcctgtg gtcgttcctt ggggattagt    16980
agctctccta ggttctgttt tccaactctg tctcattgcc actcctggga ctcagaggag    17040
aagttattat ttgctagtgt aatcactggt gtgctttcag gcaaggaaaa aaagggagtg    17100
ctccctgacc ctctggctcc tacccccctc ccattgtcat tcagcagcta tagacaatgg    17160
taggcgtctg atgtgggcga gatcggtgc ttgtgcagaa atgaatgaga tccagtcttt    17220
actgggagat ggggagctga caaagctttc tgtttagtat atttcaaatc caggctatgg    17280
tacatttgaa gtcaacagga aaggtgcca ggagtggagg tgccgagaag acaggctcct    17340
ggaccccagt gtgccgaca cttgagacta cttttgctgga cagatggagg ttggtctgag    17400
cagcaactat ccttaaggcc ttctggcatc actggtggct ggagcatgca gatgtttaac    17460
actgctaagt cacctgtctt taaatttttt ctcctcccctt attggttggg tgggaacatg    17520
tcctggagcc ccaattttca tttctgtcaa gaagggtgag attgtccacc ttcctgggac    17580
```

-continued

```
tgcctcatga actatgtggg gccatctatg gaagcccttg acacatagta ggtactccga    17640
agccacagga atgcacacac ccttaggagc agcaatcaag aatgtaaggc atgggttctt    17700
acaagaatgt aacgaccatg ctacaagggg agactcatgg gtatgattta tagagcggat    17760
catgaatgaa ttaatgcaat ttgataagaa aaagaacttc aaagcttatt ttggggtgca    17820
tgggatatta aaagtgatcc tcgtggcgaa aaggcttagg ctctgaggtg tggtaccact    17880
tacccaacat tgcagggtga gccagggaca gcacccagac ttacacctgg ggcgctgcta    17940
gtgaggccat ttctcttttc attgaactgc tccccaaggg gtgagtgagc caacttgggc    18000
agtgtccagg ctcccatttc tgacacctcc tgctgcccct aatcctaccc caggcataga    18060
aacgggttcc tgatatcagg tttccagttc agtccaccta ggcttttcag cagggactgt    18120
ccaggaaacc ccttctatgc gaagcaggtg tgggcgtggg aaggctcctt ggagatgaat    18180
caccgctgcc tcctccttgg tgaatcatgt tgaggcttgg gaacagctag ctggtggacc    18240
tggtggggga agagcggaga actacattgc tatgacacat ctccaccacc agaaggcaga    18300
agagggatag gcaaaacgaa ccagcaactg ctgtcgctca gagcttggga gggggtggat    18360
ggaccgggag gactcagctg gggctggatg tgggcagtca gagcctggga tgcctccact    18420
gcctgcctct gtccctgctt cttttgctgga gtatgtcaga acagattggg gcttgggggg    18480
gtgctgtgag gggggtgggc tcatctaccc gatgttgtct gtcctgtgat gtccaagtgc    18540
agatgtccaa ggtcacacag agagtcagag aggcaagtca gtctgctttt cgaagtttca    18600
gaagcgttgc cactggatgg ggcacagatc tggcctccat gtctgagatg aaacacccgt    18660
ctgaggtgtc ctgctgcctc tgtacagccc cctctctcat cttgtccctc ccttcctgct    18720
ttctctgtca ctatcgtgct ctctttgatc cattccctaa atttcttctt ttttgcccga    18780
tttccacctg acttttttctc tgacctcttt gtcagcctcc agtctccatc cctgccctct    18840
ggggactttg cttctccatc ccttttctgg gtccccatgg caggatgttt cctgtggcca    18900
ctcctcaggg atttgtagct ctctgaggct ctgttttcca actctgtctc attgccactc    18960
ctgggactca gagaagttat tatttactag tgtgatcact ggtgtgcttt caggcaggga    19020
gaaaagagac tcccccttccc ccactccctg ctcctaccta cccaccagtc ccagtgaccc    19080
ctgttgccag ttagcagtca taaaggctgg gcggcacctg gcgtgggcaa gatcctgtgc    19140
tcatgcagaa atgaataaga gccagcattc atcagtgagc tcaccacatg gctagggtga    19200
ggaaagtgga gtacacaagt gaatctgcct aaataggaag acgctaaaga ggggggggatg    19260
gtgggggggc acaaggagtg ctttgtatgt gccagagcag gtagaaatgc aatccagttg    19320
ggtgagagaa gccttttaag tggccttcaa agggtagatg ggatctcagc aggagacacc    19380
tgtgtgggag tgtgggtaca ttgtgagcag cagggtcatc agcgaagcca agggtcttgg    19440
cttcaccatg tgcttgtacc cttgttcact cagcgaggag tggcagggag ctggaaggc    19500
aggtgttagc gtgtggagtg tttcactgtg caccttatgg aagtgacaca atgttgtttc    19560
tgagcagaga ggggcctgcc gatggagggg cccctttgtt ccctgttggc ccctcctcgg    19620
ggtggagagt ttttattgcg ctctatctaa agaaggttgt gacaggaagg gaagcatcat    19680
gaggagggga ggagggtac tcatgtgctt tgggaagtgg gcggcggggg ggggggggg    19740
caccgagcag agagggcct gccgatggag gggcccctttt gttccctgtt ggcccctcct    19800
cggggtggag agttttttatt gcgctctatc taaagaaggt tgtgacagga agggaagcat    19860
catgaggagg ggaggagggg tactcatgtg ctttgggaag tgggcggcgg ggggggggac    19920
gacaccctgg gtggcttggc aaaggcatag aagaggatac tggaggaccc aagacacact    19980
``` taatctg 19987

<210> SEQ ID NO 2
<211> LENGTH: 19001
<212> TYPE: DNA
<213> ORGANISM: Cricetulus griseus
<220> FEATURE:
<223> OTHER INFORMATION: Downstream integration locus
<220> FEATURE:
<221> NAME/KEY: misc_feature
<222> LOCATION: 13163..13223
<223> OTHER INFORMATION: /note="n = unknown"

<400> SEQUENCE: 2

```
gagtttcttg aaaaccttcc ttctctggta gcttcctggt ctcactgcag tgagagggtc      60
cccgagccga cctccgtggc tctggaaaag tacgcttagg tcctcgtcca cacccagttg     120
ttgattcttt gggatgatcg ccctcttgtg gacagaggca ggttgcctat ggggaagcgg     180
gggtgtgggt gtgggtgtgg ggttgggagg tggggcccca ggaagggaa aaggagcttg      240
gtggagagag ggaggaaagt ctagttggct ttctgtgccc ctgaggaggg ggcaacaaag     300
atgaagctgg ggatgggagt caaagcttag gaagtctggg ctgttctagg ggagacacaa     360
ttcacttatt cagggaatgt cacatggggg catggtttag tttccagcaa acaattggat     420
ttcatctgag gcacatttgt tacaagcaac tcagggagg gcaggtttct gttaaaagag      480
gggaatctga gcctttccct ccagatacct ttccagggtt agaagaccaa gacagtcagc     540
ggggctcttg gaggggaggg ggagttgatt ggggtgcaga ggctggtggt ggaaagagat     600
gtctggtctc tcaggaggct gacaggctct gctgtgtgtg tgtggcccaa tgaagagagg     660
agcagaaggt gaaagagtcca tctgcaaaat aaaacttcat ctttctgggt gtggtggtgc     720
accttttttt ctattttaaa gatttgattt atttattatg tatacaacat tctgcttcca     780
tgtatatctg cacaccagaa gagggcagca gatctcataa cggatggttg tgagccacca     840
tgtggttgct gggaattgaa ctcaggacct ctggaagagc tcttaacctc tgagccatct     900
ctccagcctt gtggtgcccc tttttaatgc cagcactcag gaggcagaga cagatgaatc     960
tctattgagt tctgggctag cctggtctac acatcgaatt gcaggccagt cagggctgca    1020
tagtgagaca cagtcttaat ggagaaaaag gggtgcggct taaaaaaaaa aacagaacaa    1080
aacaaagtga aataaaataa gtaacaaaac ttttgtctgg tttggggata tagtttaaaa    1140
ctgagaagtg aagaggcatt tacacgggaa attttggtgg gtgcagcagg caggggtag     1200
aattgggtgt ggtcaggtgc acactgactg tttcatttat ccacaagatt tcaagttggc    1260
tcttgagcat ggcctaggtt ccagggaagg ggtagagctg gggacttggc agtagattcc    1320
ttcctctccc aagggcatc cgccaccttt tcaggcttgt cagagcgagt ggctatgttg     1380
gtcagaggga gaggccctgc taccccttt cccgtagtag aggttctgtt cttccctccc     1440
actgcatact tggcagtaat cccatagtct agtcacccctt acaccatga tgctggaaca    1500
gcagcatctg tttccataaa gtggtcaggc cccaggtggg gggttggggt gagactggct    1560
caggatgcgt tactggtcct ctgtcaagca catctgaaac tgtcaagaac gaagcaccac    1620
ttcccacagt gtcagtgtcc cacagctctt gcatttgtac aaggagtcac tgtacctact    1680
gtggcctcat ctccgaagaa ttatgtctac tgtgtgttac taaccgcatt caagtgacag    1740
gacagagttg caggacctcc accaaggtgg gggaatagga gatctgggag ggactgcgcc    1800
ctcctgaccc aggccagctc ctcctccagt ttctctgctg tttccagatt taatgtcact    1860
```

-continued

```
attccttctt tgtatcattc tcttaaatgt tttaattaaa tatcgagaat atacaaacag    1920
cttatatatg acacctaaag tatacaaatt gcaacatgaa acacccactt taagaaacaa    1980
acatttggtt gagatggctc agtgggtaaa ggcatttgct tccagcctgc tgacctgcat    2040
ttaattccta ggatccgcat ggtaaaagga gagtgcacac atgcatgtgc acacataaat    2100
aaatgcatgt aatataataa ataaataaac aggcttggag agatagctca gcagaggcct    2160
ggaactgggt tcccagcacc caagtgggca gctcacaaca gcctcaacgt cagatcagat    2220
gccctcttct ggccacagca tgcatgtgca ctcaattgca cattttcccc ctccaacatg    2280
tatacacgtc taattaaaaa ctaaacttaa atctttaaaa gagagaaaca ctgtagaaga    2340
tatagagcga gtggctcaaa gggccagaga cacaccattt gtgcactggt tcattaggga    2400
tataataaag gaaggagaac aagagcagga tggaaaatat gcccgaggcc aggcatgtga    2460
ggtggagtga agcccactct tgccctcttt gggagctcta ctctcaagga acctctatca    2520
tccagctatc tgagccctct tatttgtttg gttttattca gggtctcatg cactcccaga    2580
agcccttgac cttgctattc cgttaaggct ggctctgctt tgaattcccc attctcttct    2640
ctctcccttc caagtgctga gattacaggt gcatgtcact atacctggct taagcctgat    2700
ccctgtaggt tatttataga aacttcatta ggaagcatga ttgattacat tcctagtcat    2760
tgaccaagtt tgccttcagt cctggagggt ggcaggtggg gatgaaagtg tcaatcatct    2820
aacatctggg tctagttagg gttactattg ttatgatgaa acaccatgaa caaaagcaag    2880
gtggggagga aaggtttat ttgtcttaca cttccatgta gtagtccatt actgaagcca    2940
gggcaggaac gcaaacaggg caggaacctg gagtcaggag ctgatgcaga ggccacagag    3000
gggtgctgct tactggcttg taccttatag cttgctcagt cttatagaac ccaagaccac    3060
cagctcaggg atggcaccat ccacaatgaa ctgggccctc ccccattgat cactaattaa    3120
gaaaacacgt tgcaggcttg actatagctc cttttattta ttttatatat tttatttttg    3180
agacaggatt tctctatgta accaccgtag ctatcctgga actacctctg tagaccaggc    3240
tggccttgaa ctcatagaga tctgactgcc tctgcctcct gagtgctggt attaaaggca    3300
agtgccacca ccatctggtt atagctcaac attatatttt ctcaattggg gttcccttct    3360
ctcagatgac tctagcttgt gtcaagtttg acataaaact gtctagtaca catataaaac    3420
actttcttat ctctctgtag atcccaaggg ttccagaaac ctttgggtgt ctgaaatggg    3480
aggaagacca taagtccact ttagaatgtc acagtacgtc tgtttctggc tttcttttcc    3540
ttttccccag ctgatctatt tcaatgccga tacaaggcat cccggtatat cttacaataa    3600
tgtttgagat ctcccacttg ttcttcattt gcaggatatt ttatctatta ttggcttctg    3660
ctttaagata tacactttag gggactggag agatggttaa gagcgcttgc ccttcccata    3720
gtggacttgg gttatggtag ttcacaaagg cctgaaactc cagttcctgg aggagctcat    3780
gccatcttct ggcatccgtg ggaactgcat gcatgtggta cacttacatg ccaacaagac    3840
accaatacac ataatacaaa aaatgaataa gccaggcacg gtagcacagg cctttcatct    3900
agcactcagc aggcagatct ctatgagttc caggctaact gaggctatgc agagagaccc    3960
tgtctcaaaa caaataaaa caaacccac acaacaaccc tccctaagta aataaatacg    4020
atatatatat ttcagtgtga gatgttcaaa tccacaatgc aacatttag aattttgttt    4080 ggcattgcat tgattctgta gagcaaattt tggagaatat tgactcttca aacctatgaa    4140
catgattgat ctcttttctg tttgtttttt gagacagggt ttctctgtgt agccttggct    4200
gtcctggaac tagttctgta gatcacgctg gcctcaaact cagagatgtg tctgcctctg    4260
```

```
cctcccaagt gctgggatta aagatgtgtg catgccacca tgcctacatc tcttcatttt    4320
ttaagggtat tttcaatatc tttgaatgac atgttatcat ttctaatgtt taagaacttg    4380
tattagcttt ctggtgctgt aaaaaaagac atgagacata tctattttag ttcagttttg    4440
aagacttaaa tccacggtag gttggccctg ttgcttttgg gtctttggca aggcagtgcg    4500
ctgtattggg agcccgtggt ggaacccttt gccccatggc ctcgatgtga agagaagag     4560 gaaggggcca gaccccaat atcccctta aggctatgcc tccattgatg agaagaacgc      4620
tcactagttt ctacatttc accttgtgtg gtatgtgcta ggcaagcaaa agcacaaatc     4680
ttgtggttta aaatacttat tcatttgctc ccaccaagat tgtccctttg tgcaacctgt    4740
actaggtccc tagaaaaaaa cctaaggtca aggacactg gtgtcatggc cactgctagt     4800
gctctgtcat cccaggagcc aagctccaca agccccacca ttctagcctc cagtcaagac    4860
tccaccctct tggcctgtgt ttagcaaagc ctctatgtac agctttgaat gtgtgtctgc    4920
ccttctcctg cccccctccc ttgaagtcca cccaggttat gtagagtctc accagcagtt    4980
ggcagaactt gtctctcagt ctaccctgct caggctccag acgttcttgc tgccgtggcc    5040
ttcaaggtcc catcttttga aagtcctccc agctcttcct catccccagc ctggaaatga    5100
gactttcaaa ccccattatc gcctatgagt gttacgagtg tcaagctttt taaaggaagc    5160
tgctttgtag agatgtcaga gatgccagga aaggctgctc tcattgactg ctaatggaag    5220
tgtgaactgt tattactgtt tgagaaagta atatagcaag agccacttaa attaaatatg    5280
catgtgcccg gcacccagca gtatcacact ggggttcata ttattgaaat aaaagcatca    5340
tccctcaaag atgcaaatat ataaacactt gggtgaaaat attaattgct ttcagtaggg    5400
ggagaaaaat gaagcgagga agggctctgc atctagggag ttagcaaaag gctagaggaa    5460
ttgtggcgct tctcagaaca acatacgcta accttaaaaa gcaccagagt ctgctgtggt    5520
ggcacatgcc cctagtctca gcactcaaga tgtagaggca gggggaatcc tacaagtgtg    5580
aggccattct ggattttact gtgtccccat ctcagaagcc aggtggtccc aaccctcata    5640
ggtagagctg tgggaagggc agaactccgg gaagggtggg aaggagctag ctgtgctctt    5700
tttggaggtg tggtaggtga actggagca aggaggaacc tgggagtcac tggctgttgc     5760
agaggtatgt ccaaagagtt cccctagtgc ccacaccta gcagtgccct ttcagagctt     5820
agggagggca actcatttat gtccagaaga agagaggagt ggggaagccg tgggcttctg    5880
cttccatcct tctctcacag gacgactaga accaccaatc ggtaggacct tctgcctgca    5940
gggtcactta gagctttcag atggggaggg tctcacatgg tgcttcctct cagtgacacc    6000
cctcctccct cttcaaacct aaagctctgc gagctcacat tcatcccat ctcactcctt     6060 acagaaggat attcccactg tagtccctgg ggtgttagaa tgaagccgca tggcttttcc    6120
catgatgctt tgcctggacc cagcatggag gatgacagca cactgatccc cagtcttctt    6180
ttctgcatga aggctgttcc tgatttcctc atgagctatt tagaagaagg tccactatga    6240
cttccacctg ctccatgctc ttgcccctct gggttatttc ctccagagaa aagaattagt    6300
aagccaagat gtcacacacc cactagtata gcttctttt ctatcacata tttatttatt     6360
ttgtgtgtgt gagagagaga gagagagagg gagggggagg gaagagagag agagggagag    6420 gggagggag ggagagagag agagggagag ggaagggag aggagagagg gggagagaga      6480
ggaggagaca gagggaggga gagagaggga tggagggaga gagagaagga ggaagagaga    6540
ggtggcgggg agacactttt ttcggtgtaa tttatttatt tatttattta tttatttatt    6600
```

-continued

```
tatttattttt ttatatattt gagttacaaa caagattgaa ttacatgaca atcccagttc      6660
ccttctccct cccttcctcc cacccccccc aactaaaatc ctacctgtca tatgtccttt      6720
cttctaatct acacctgact caaaatttct gcttcctcat gacctctgca tccttccttt      6780
tcttcccttc tcactctcat agcttcctcc ccctcttcc catgttctca atttgctcag       6840
gggatggtga ccctctcccc ttctccaggg acaaagttt atctctttta gggtctactt       6900
tgtttactag tatctctggc agtgtggatt gtaggctggt aatcccttac tctgtgtcta     6960
aaatccgcat atgagtgagt acatatcatg tttgtctttt tgtgactggg ttacctctct     7020
cagaatggtt tctttgagtt ccatccattt tcctgcaaat ttcaagattc cattgttttt     7080
tttttttttc ctgctgagta gtactccatt gtgtaaatgt accacatttt ctctatccat     7140
tcttcggttg aggggcatct aggctgcttc cagtttctgg ctattacaaa taatgctgct    7200
atgaacattg ttgaacatat gtccttgttg tatgaatgtg cttctttggg gtatatgcct    7260
aggagtggaa ttgctggatc ttgtgggggg ggagacactt ttgagagctg tttccttctg    7320
ccatgtggtc ccagggattg aactctgatc atcaagtttg cctgcaggcc cctttaccca    7380
caggaccatc tccctgaccc atttcttcgt ttaacaaagc taaaatgcct tacagtgtgc    7440
acccagtggt gagtgagtat cttccccatt ttctttttaa gagaaaaaca gcctagtttt    7500
cctcttctgt ttttgtaaaa acagcttat tcaggtataa ttcacacgcc acaaactgac     7560
cctatgaaag tgttcagtaa ttcagtgccg agtatgatgt atcacacctg tgaccctggc    7620
actcgagagg cagaagcggg aggcccacca cacattagag gccagcctag gctacacagt    7680
gaatgtcagg ccagacaggg gcatataatg agattctgcc tcaaaagca ctcccgaacc     7740 cagacaccct caaaatgttc agtgttgtaa attttaaga atacgttttg gtgttttact     7800
tgtatgtata tctgtgagct actgtgcggt gctgggaaaa atcaggggcc tctactctga    7860
actgctgagc cacctctcca ggtccgatgg agaggtgttt aataagcttg gcattctgta    7920
agcttcacca cgatttgatt tcaggtattt taatccctt agcaacctga tgcccattgg     7980
cagtccttcc ctctggcctc tgacagccac caactttccg tctctatgca tttgtctact    8040
cggggaattg catataaatg aaccactcag tagccttca cgactacttc acttgttttc     8100
agttcatttc tgctgcagca cacatcagca cttagttctt tttatgagta gcatcccata    8160
tgtacatgct acaatgtgtt catatatgta caatggctga tgaacatctg tgttatttct    8220
acatttaaaa aaaatgctgt tctaaacatg agtgttcaca taggtttgt gcagatacat     8280 ttccaattca tctgctgagg gacatatgca ggcatggatg agctccttct tgtgcacaga    8340
aagcaaatta catggatttt cacatcgctc accctctttg tgaggtagaa acaagggcat    8400
taccgtggcc cttggtttcc tgtgagcttc ttatcagggt caacctcatt agtgctgtac    8460
aattctacct ccactattgg ggtgtttggc tcagtctcca aacacacttt ccagtccaca    8520
tatcttctga gcagagcaga gaagacctat ttgtctacaa cctgggagaa tccagctgtc    8580
tgatctgtgg gtggtgctga aagtacagc tcaccagaaa taggggtcct caggccatgc     8640
tgccacagtg gttcttgcca ggcttagcag aagtgttatg taggtgcctc aatgcccttc    8700
ccagagcttt ctgaagctgg gagggcaaag gagcctcaga ggccctgctg tgttagtaca    8760
gtcacagtag ctgcataaag aaacaaaaag ccccaagaaa caaaaatcac ctgctgagtg    8820
aaatccccta atgaacccag cagctgggag gcaggaggca ggctgccaag gtcaccatag    8880
caaccagaaa cagagccttt catacagtct ccctgactct tcagagagaa agacctgtg     8940 acctcttttgt gaccttttgg cttctcttgg ctgctcaggt tgtttcccct ctcatcccag   9000
```

```
gtttgacaac tcttctctga ttggtgatac ttttcccacc ttatttgcat acccatatgc    9060
agctagctag ctcccctacc cccgccctg cacatctatg aatcttggca gagctagagg    9120
tgctccagga gcccaccaag gaggaagaga aggaagactt caaagcctgc cccctgggtg    9180
gccagcagcc tgattccaga tgttcctgct tgctccagag atccttcctg aagacttcag    9240
ggtctggctc ctccctggct tgctcattgg agaaggaaga atgccttcca gaatcaccag    9300
ggacaaagag tagaaggtcc ttgggtccaa ggcttctgcc ctggtcagga agcttgctgg    9360
attccaggat ttgatgagca ggtgcagtgc aggtgcaggt gagggacttg tgtttgtctc    9420
agcctccaag attcttctca cttggtgacc tacagatggg aatttccctc tgcagcagct    9480
tttaccctct gagactagtc ttctgagctc agcagctcca aactttcaga cccgctttgg    9540
agacttgaga ttcagctttt ggagatccaa tgctccagag atctgtgact tcagccttct    9600
cggaggcctg ctggagacag aaggcctgct tctgttattc ccattgctgc cctgcaggct    9660
tgctccacaa ggcagcagtg ttggcacaag aaggcctcca gcctttgaag ttttaacaat    9720
tcccagaatt ctaacacttc tcagagctag taccccagtg ctagcttaaa ccttttgccat   9780 ttaaatcctg catggaccac ctgtttaaat ttttatccta tttaaaggga actaacaatg    9840
aagtaccccc ccccctgca atttgtactc gtcactgccc actccatcgt ggaggaagac    9900
ggaacaaaaa cctggttgga gacagatggt ggtctctgct gattgttcca gaagggctgt    9960
ctgtggtaaa aagttaggtt ttggaatatg cagaattaag ctgaagcctc attgtgagct    10020
tggtgtggtg ctcatgcctg acttcgggaa cttagaagtc aaggtgggag aattaccagg    10080
agttccaggc caggatggcc tacacagtgg gcaagacagg gctacagtga gaccgtctca    10140
accaaactaa accaaaccta ccatgccaca tgaaaacaaa acaaagcaga tcaagcccac    10200
aaaacaaaat aaccccagat tggaaccaaa ccatatcaaa tcttcccttt gccttagatg    10260
tgggcatagc tgtgtggagg ctgaaaaaat tctcaaggct cagtttggtc atcttcaaat    10320
ggagataaac atggcttcct gttagggatg ctttgtggtt gaaaggaaag aaagcattta    10380
catcccttag catcaaatag agttaatgat aactattgct ggtgtagtaa aaatgttact    10440
agttagtata gtaaatactt atgaggtagt ggttagagta ggttgaaagg caatagcagt    10500
accattccac aattagatcc ctcaaaactc gaggtgggtg agggtggggt gggagccgag    10560
aggccatcac ttctttttat atttatttat ttatttattt atttatttat ttatttattt    10620 ggttttttcga acagggtttt ctctgtgtag cttggggcc tatcctggca ctcgctctgg    10680
agaccaggct ggcctcaaac tcacagagat ccgcctgcct ctgcctcctg agtgctggga    10740
ttaaaggcgt gcgccaccaa cgcccagccg aggccatcac ttctatggag gagaaagcct    10800
catgttggtg gctggtcgag gaggtaccag ggttctggtg agcatcaggc tgaagggacc    10860
aggcctgggg ctgagaccag aagtagtgag caaaagtgtg agcaaacagt gactgaagtg    10920
ggacatgggg gcagggtcct tttaagggac acggggatcc ttctttcaaa ccttgttaac    10980
acgacaccag cacccgaaag ctgatggatg ggatagtata ggaataaaca tgatacctgt    11040
gcaaatagaa gttgtcccca gaagaatgcc attttgtaac cgttcaaaaa agtcagccac    11100
agggccacag ggcccagctg tcaccagctg ttgctatctt ttttttttgc tgtaaacagt    11160
aagaacaaaa ctcaacaaaa gatggaagcc agctggggca gagtgaggcg gaggtgtgag    11220
cccactgtat caggaggtcc tgcagagggg agcgcttggg gagggagtgg gctgtgggag    11280
gctgttgaga cgcttccagg aggagatgcg tgtggatgcg ggcatccaga agaagcagtg    11340
```

```
tggccagtca gaggaggagg ctggcatgaa tgacactgta atgccatcta caggggcgag    11400
ggactggtga ccaaggtggc aacagtcata gacagtggat atgggctgtg gtggacagtc    11460
aggcctgcac ttcctgaggg ataagggcag ggccagcaac cttcacaaga aaattgaaaa    11520
gccactcagt attccagata aaaaactcaa actgaaaatt ccaggctctt ccgcccccagc   11580
aatgatgggt tttcatattg tcttccaagg ctcttatgtc atcatatggt gactcacacg    11640
gctgggcatt ttatattttc tacttgacct gtggcatata ttgcccccac cacatgcata    11700
aagtattccg ggtacagtag aagggtcct ctccactaca ccaagaatcc ggggggtgccc    11760
attgctgtat agttgtctta ggggtctcag ggaagctgtc ctgctggtgt gtgtgtctgg    11820
ctgtgcaggt ctggctttcc ctgggcagag cagcaagagg gatttgaaca gagaccaaag    11880
ggttgaagaa tgaagggtca gccagaagag ctgtaggtgt accctacctc caggggtaca    11940
gtttctcttg ccctgaatcc cagcatcccc agagggtgac tgtggtctct ttgatattct    12000
tccaaccctg caagttccaa gtctccagac ctcaccccct tgtggacacc ctggtccttt    12060
tctgtttttt ttcctgacaa cccccaaatc tctttatcct ccactataga aacccagtgt    12120
taactgaggt ttaaacgtag agcaatggga aaaccggttg agcctgggag gcctcattct    12180
tagtgattgt tacaggggc aaaaggtcaa tacttgtact tatatgtttc acacggcagt     12240
aaaatatgga tggatacttt gtattttatg tagaagtttc cagaacctgt taagtgactg    12300
gaacaacata cttaatatat tttgaaaaaa attagaaaga tactataaaa aatcacataa    12360
aaggggaaaa aataactccc ctaccccccaa tcttcaacta agcaagaagt tccttgtgcc    12420
ttctcttagc tcaggtgaga gatgctcagt ctgctccagg gggctgctct tttattgcag    12480
tcctccctcc ccaccctgag gacagcactc gtgtttcctc atcaagtctt cccaggaaag    12540
catgattacc atttttaatgt tagaaagagc tatttgctgc tgccatgcag tggttgctaa    12600
tgtcccttcc tcctggacac ttgaggctgt ttctggttgc acttctctga attaccgagg    12660
gcttgtggag actctactaa caaaagcagc ttcaccagca ctgactttcc acagcaggag    12720
gcttcatcag atccctcact tctgtgactt tgtgctgagtc ctgcctagtt tgtcattttg    12780
ttttgacaag ccattcattt ctgcagccca gagcccacagt gttagtttag gaacactcac    12840
atctaactgt ttgaaacttg actgtttgct gatttacaaa tttggtagta aaaactactc    12900
caaggtggag ccaggggata gctcagatgg ggtcccctta aaaagctgtg tgtggtggtg    12960
agtgcttaga atcccagaac tggggaggtg accagtctta gagattccct aggactccct   13020
gaccagtcat cttagcctac ttagcaagcc ccaggccaat gagaaacccc atcttaaaaa    13080
aaaaggggg gggtggtttc tcagttttaa cagataacat ctataacaca gctctcaccc    13140
tgaggtttag ggatcatttt ggnnnnnnnn nnnnnnnnnn nnnnnnnnnn nnnnnnnnnn    13200
nnnnnnnnnn nnnnnnnnnn nnnagtggaa agattgtaag agccagaggg acaggaagtt    13260
tgctatgaga ttggtgggga catcgggtga gttgcagcaa atctcctgtg gccttcagat    13320
gctatttgac agtttgctta gctttgggtt ggtaggaact agtggtctgt cactacactt    13380
caggagggtt tacaagacag tcataggaag ttaagtgaga cacagggcca gaaatgaatg    13440
gttattaagg gaactaacga tagtctgaga tagtttggct ctaggtctgc acggttctga    13500
tgcttaatca caaagctctg agcagtccgt ccagcttgtg gatctgtaac aggtgtggct    13560
tcttttctgg aaacttcagt tcatactccc tattccaaat gtaggagtgt aagacgctcc    13620
cttttctcctt tgtgtcccg tctgagctca gagcctgagg gcaggaatga tggagcccac    13680
aggatctgca caggtgagga gactgtcttc ctcttctcca tcagacagga ggaagctgat    13740
```

```
cagcccgagg tgtctcattc cccatccttt agcacctcct gctggccact ctatccccat   13800
tcatgtggtc ctgccaggtg gtgctaaggg atctctgggg gagcccagtg gtcagctagt   13860
ttggacatta gctggttgga gcagaagtca gaccggtttg ttcctctcag ggttaagtta   13920
ttgggctaca gcagagcata ggctcccgta gggaagagct gagctaagct tttctgtgcc   13980
agaaagctat gcttttctgt atctgccgtg ttgcagttga atgtgctttt gttctctcag   14040
gccaaactga tcctgtaatt caaaccctcc atgggcttca gccacaggcc aggtcctaac   14100
tctaagtttg cacagtaagc cctccgcagt tgggtctctg gttctttcag ttcattttct   14160
gcagtttgta cttttctct gggccaaagt ttacagctgg gcagaaagat tcctggacac    14220
acacataaac caaaccaaaa cattcccaaa cacccccaac ccaataaaaa cacatcccct   14280
cccaataaac ccccccaaat ctttcctgtc agttatcttg agaaacctgg gtcttgatgg   14340
gatgtgtggg caaggtgcca tttgcctgac ggtgcaggca gaggcatcac agtcctctga   14400
gagactagct attgaaaaca agcaaaaaat gcacctggac ataacaaagc cagtgctaac   14460
acgttacaaa gaggatgcta agggcagata aatgggggag aatgtgtatc tttcatgcag   14520
aaaattttgt tgcaatgtag caattttgtt tgctaacagg tattttagga gaaaatgatc   14580
taacagcact aaactggaga caaggcatct actaacctca ctcggtagag cccagcctgt   14640
actgcactgc tgctggcaaa ggagcctggt ccatgccaca ctcgggactg ccctcttctg   14700
atcctgcacc cttcccacct ccctgtcatg ttccaaccct cccgaccttc tataaccagc   14760
tgaatgttgt ccactcagtg acatctcagg tcctgggctc tccactgtcc tgatgtgttc   14820
agttcctctc caacagtcct tgcttcaaga ggatgactct ggtttgcaag actgtccttc   14880
cttcactccc cccttcttcc tatctctccc ttgaatatga actgagatac ttgtgaaagg   14940
gccacatcac gctcctcttc atttagcgta agtcctgcca catagtgggt gctcagtaaa   15000
tcttggctca cacgaaggag ggttgtgggg aaaagggctg ggggtggggt tgtggaggga   15060
aggtgctttt aggtaggagt ctgatccatg aacgtcttgg agaatgagcc agaaagatga   15120
agcatgtgag attaggcctc atgggtgtgc ctgtgagact tcagtcacgg ggcaggggtg   15180
cctgtgagtc atcgtctcag ggatacctgg agggatcagt tctgaatgct gcattcattg   15240
ttgcgttcct gagtcaggta gagcaggtgc ctatgagtca cgatcactga cttcctgaag   15300
tgcaaatgca cacgagacct tgttctcttc aaacaacaca ctcccagcca ccatgctcta   15360
ccatggataa aatcatggct ggccccatag ccttcttagt gtctctgagc tcatgacttc   15420
caggggtaga gtctatctga aggtctctat accagttcca gtcaaagggc ttctactgct   15480
ccagctgagc ctgccctgca gtggggaggg gacatgtggg aagccttttc attctttag   15540 tcacctgtcc ccacactatg tgtctgcttg cttttctaag taggggaat agagacacaa    15600 gtctccatcc acactgttgt cctgtaggta ggccctattt ttcagggatc tttatctgac   15660
cttgggtctc caacaattac cctccacccc catcagatag cagcacagtt gagccatttt   15720
tcctcattgg ctttggggca ggcagctttt cattttaga atgtctcaca caccagtcag   15780
gatctgtttt ctttattttc cattcacgac ccagctcaag tcaattgaga ggttctctta   15840
gcgagcctct cgcttggtct gtggacacag tgcctgctct cctcctctat gggagtgagg   15900
tgggaacaaa tggcatcctc ctaacaccca gctctctctc tgaataatcc cagactgtct   15960
ttttcttgag gcgaggagag gtttattgtt tgctttgggg ttaacctcct atctaattcc   16020
catagaggac caagagcttc tctagaaagc tttgaaacat attcccttta cctgctattc   16080
```

```
ggggccactg taatcaaagc agtgccaata tttagcttcc tgtgtcattg gggtctgggg     16140
aatgagtgaa tgaatggaat tatagttggg aggtctcagg gtagtttcct ccaggagtga     16200
gaaatgaggc taataggagg agagaaggct ggcaaggagg cagcaaaagg ggctcagctc     16260
tgggttcccc tggggcagac ttggaggctt gggcttgaac ccgccatctt gccagctgtg     16320
tgctcttggt aaatgtactt gttttctgtg caagttgcct catcttgaaa actcagacaa     16380
tcatagaagc tgccacacag cgctagtcca tttgcaatta tgtcttcttc aggagatgct     16440
ttatgtcagg tgtcagcatt gttggaatga ttgatcctta aaggccaggg ctagcgtgcc     16500
agcaggtcag agagtggttg ggaggtgaga gtcctgggt gaggaatttg tgtagaaga      16560 gaagttggtg tctggctcct ggtggagtgg ctcctggaga agaaagctga agctgagcac     16620
tgttcaggct atgctgcata tgggtctcag cctgtcctgg aggatggagc tcagcctgtc     16680
ctggaagatg gaccacatcc tgcatgccag tgtctccacc gctgtctgtg agggccttcc     16740
attcagcctc aggcctggag agggcccag tggccagggt cttgtgcact ctaagtctgt      16800 tttttctccca ccccatcttc agggccagct cttacctcag gcccacagtc acaggggcct     16860
ggcctgggct catgggaact gattcatggc tctggcttct cctttgcctg gcttggagat     16920
ggaaatgctt gttcatggag ctagtgaagg agaccagctg cacagctgca tgaagctggt     16980
gagtccaatg ggactgggtg gtagttacaa aggacccagt aagttctgaa tacccagagg     17040
agggttggaa ggctaggtgg tccttgctgt catccttgca ctcatgttca tctgtccagc     17100
cactaccctc ttacctttct gatgctttgc ccctcatttc tagggcaaca atctttctga     17160
tttccatgca ctcctggcca tgcttaaaa tctaatactg agttaccaca gtgtggctgt      17220
gtgactacag acctggatgg tcctggtccc ttcatgccag gaggcctgga taagcctctt     17280
gtgtgtactt ccccaaagtt ctgacatgca ggaggcaccg tacagcagcc catgattgca     17340
gtgtggttta gcacacatag ctgatgaaac aagatgacac ttgtagctga ccctggggtt     17400
agagtgagag ggtgtggtta cttgagggtg agttttggaac cccattagag ttccagtaag    17460
acaaggctga ggatgtgagg ggaaaggggt gctgacccgt agctgacacc ctctgaaatg     17520
ttctgaggaa gtggaatcct ctggttattt tacacaccac caactcctca caaacgaagc     17580
atcagagggt gtccctttct ccaagccttt aatctagctt ttgtggatgc tgtcaccctg     17640
accacagtga ctgttcaaag aggtggacat gtgacctgaa tcagaccaat cagagctgta     17700
aattaacctg gtctttattt cctaaggtta taaaatcaca atatgaaaaa tattcctagt     17760 gtgacagagaa agaagaaat taacacacat aataaccact gactatagaa aaagaaggag    17820
cattcagagg acaaatattg catcttcaga gaggcagggg cagtggggca tgtgggggca     17880
tgtgttcagg aaatgatttt ggtggagatg attgcacaga gagctgggtt atatagtggt     17940
atgagcacct ttgcattgca aattagcata tatagctttc catcgagtag cggtgtaaac     18000
tccataggcc ttttgtttag caagagaaac tccacaaggc aattggaaac caaatgatac     18060
agaaactgtg caagccatgg tctaggaaga aagcacattg aaaacatgct attggacaaa     18120
tgatattgaa cgtcttaatg gttttagttt accagatggt gacaacaaag tactttagac     18180
ttggtgactt ccccgtgctg gaagctggca agtttcaaag gaccagaaga ttcattgttt     18240
ggtgaggcct attctcttggt gcatagtagt ttttagttgt tttcatccct agtcccctct    18300
ctcatctccc tccctctctt attgaaccct tcttccagca aaaccccctc ctatttttcat    18360 gtctttgtgt gtgtgtgtgt gtgtgtgtgt gtgtgtgtgt gtgacccact gggcttaatt     18420
agagttcttg ccagagagtg agtgggatgt tattttctgg aggatgggga acttactggc     18480
```

| | |
|---|---|
| tctacgatga agaaaatgga caccgtctac cataatagct gctaacttct catagtccct | 18540 |
| cagggaggtg gtcattggat ccctcccta tccatgttga aatgttgaag agtacagtca | 18600 |
| tgtgcacgtc ttgttcaggt gaacacagct gtgttgaggt catgtctgga agaggtcttt | 18660 |
| ttggatgcgt ccttatatag cagaaggatg aaggaacact gggggttcact aattcagtca | 18720 |
| tagggtctgt acctgcacag cctaattgcc cagtaatact gggggctaag ctttgacata | 18780 |
| tggaattggg ggctgtgggt ggcatagaca gcggtctata gcgaaatgaa gggaaaaagc | 18840 |
| gtttactttg cttaaaccat gaaagtccaa ggttgagatc atagatcact agacaaggag | 18900 |
| tgaagagtta actgtgcaat ttctgcctgt gtggcaagtg gtaatgatgc tgcaatttgt | 18960 |
| agctctacca tcccatacat ggtgtgtttg gcttccagtt g | 19001 |

<210> SEQ ID NO 3
<211> LENGTH: 7318
<212> TYPE: DNA
<213> ORGANISM: Cricetulus griseus
<220> FEATURE:
<223> OTHER INFORMATION: Upstream side cluster
<220> FEATURE:
<221> NAME/KEY: misc_feature
<222> LOCATION: 1303..1359
<223> OTHER INFORMATION: /note="n = unknown"

<400> SEQUENCE: 3

| | |
|---|---|
| ggatcccaac actgccactt atgactgaac tctgggcact cgcttatagt gtgtttcctc | 60 |
| atggggatgt gaatagtcct ctcataggag gaggacggga cacacgaagt tcttactgga | 120 |
| aagcctgaca ccgtgtgtac ctagtaagtg gaagttgaat gaaaatgagg acattgatat | 180 |
| ggtggaagag aaggtttta ttgtagatat gagggagaga gcagccagag gcatctggaa | 240 |
| gagtccagac tgaacagggc cagcagaata gacccagcca tgagagaaga gagagggaca | 300 |
| agagagggga ccaggaaagg cgaggaccaa gaggacaaag aagaaccaag agagcatgtg | 360 |
| gcaaaaatgg cgggttatat aggaaccata gctggggaaa gggaagcaaa gctcaagggc | 420 |
| tggagaggtt tagggtggga gtgggggtaa gaagtgctga gaggagccag gactttgtat | 480 |
| caggtacttg caatggagag agcctggctt tggtaggcta ataggcacc acagttagcc | 540 |
| atgtgtctgg gggtttcttt gggatctgac attccagtct tttgttgat gataacgagt | 600 |
| gatgtaatct cttctgtaac tgcttcttag ttaaaattgg ggcattgttg ttgggggcct | 660 |
| aagaaggctg gaagtttggt caaaggctgg gaagagaaga gtgcaggctg gaggacatct | 720 |
| gttttgctta ctgcccaggt tctgagggac cacctggggc tagtgaagtg caggctgctt | 780 |
| tggagtagtc taggatttcc aagaaacacc tggagctgga gcgttgcagg cagttttgga | 840 |
| gcggtctcca ctccagctga taagaaatct gctggggcag gtgtagacta gggacagaag | 900 |
| gtaaagttaa ggagcttagg ggaaattttt atcttgggtg tacatttgaa acttccaggc | 960 |
| ccatggtcct ggtagttgca gtgacagtac agggagaggt ggggagttgg gggcggggga | 1020 |
| gtaggtatca agaccagggg agagagagaa atcttaccct taggaatagg caggtaggga | 1080 |
| aactttgttt gacctgtgag aagtggaccc aagtctcaca actccctgaa gcttacaaga | 1140 |
| acattttaag tttatagata aaaatttat atatattagc attatcagtc tttgtaatct | 1200 |
| gtactgaaat ccacattgta gaaaagcag ctggctcaca ccttcaagtc acaataaaag | 1260 |
| cttggaaacc gccgcccccc cgcccccccc accatgatga ggnnnnnnnn nnnnnnnnnn | 1320 |
| nnnnnnnnnn nnnnnnnnnn nnnnnnnnnn nnnnnnnna tgatgagtta aaagcacgaa | 1380 |

```
catgctttcc tctatccaga agactgggtg tataaaaaca cttttaaggc catacttaga    1440
aaacaaccag acaggtggta gtggtacatg cctttaattc cagcacttgg gaggtagagg    1500
caggcagaat tctgtgagtc tgaggccagc ctggtctaca aagggagttc caggacagcc    1560
aggactgtta tctagagaaa cctccctgtc ttgaaaaacc aaaacccaag ccaaacagaa    1620
tcaaaacaaa acaccttttt agaccctcac aactaactta agctttcaca tcctttacat    1680
cttgcacgca tataaacttc acttttttcag accctctagaa cttatacaag cttcaaacct    1740
ttctttctac ccaaacattt actatgagac acacgtggtt ggttcctgag agcagtcatt    1800
gcaaagcaag ttcctttaaa taaggaata gtaaaaagtt acactgaaac ctgttttggg    1860
agtttatctt tttcagtgtg aagtcttcca ggaagataaa gtctgtctac ctttctcagc    1920
gggataccta gtagctcata tcatatgaaa tggactgacc aagcagctgc agccttggag    1980
aaggaactga tttgcttgct gctgttaaca taaagctaca gttagtcatc aacagtatcg    2040
gagactcgag agggataaat tatagcagaa agttaatcca aatggcccct gtaccagtta    2100
aagtgacaga tttattggct acctagatgg ttagcctaag tgttccatgg tggtcttgat    2160
ggctttgttg ggggcagaag tatttggtct ttggctgtca cacaggatag cattaaatct    2220
tcagctacca cacaggacaa cattggtctt tggctgctag acccagagat atgagagatt    2280
ttcctgtgga ggaagacctt ggaaaactgg catccttga tgaggaagag taggatagtc    2340
aacccaacaa tgtccacagc ttgggcagaa acattgtggt tgaggcatgg gtcagttctt    2400
tgcccagtgg ttagtgttac cacaatctag gtggagtagt ctgtgcccca ttatcttctt    2460
tggagacttt agggtcattg ctaggggtgg cagttctgtt tatcacagga agttttttt    2520 ctattaaaca tttaaagtgc catattcagc agatctctga ggagtttgag gaccatcatc    2580
tattaagtat acttgagtta aggaagcttt acctggtttc agttacttgc tttaggctta    2640
accttgaaaa acatatagag agcccagtgg tggcgcatgt tgggaggcag aggcaggtgg    2700
atctctgaga gttcgagacc agcctggtct acaataacta gttccaggac agcctctaaa    2760
gccacggaga aacccagtct caaaaaacca aaacaacaac aacaacaaaa caaaaaccca    2820 aaacccaaa ccaaataaaa ccatatgcag aaggctaaat aaaacttgtc cctgtaaaca    2880
aattgcattt gtacttagta tggcttatga gcatagtttt gagtaaagaa tttgatcatt    2940
tataaggtgt ctggctgttg acttgcatgt cttaattatc tttaacagta tacaacaagt    3000
tagtacttat ttttaaaaaa taagatcagg attttatgat tttagccctg ttaagtttga    3060
gcattaaaaa ttgaagttta agaaacttta gcatcaaaat gaaactttaa accataaata    3120
aattctgcag agagaccggg gacttaacaa aaccataaat acagtccaag ggggattggc    3180
aaccttattt cttgatccct tttttttttt tctttttgag atgggggtttc tctgtatagt    3240 tttggctgga actcactcta tagacaaggc tgtccttgaa ctcacagaga tctgccacct    3300
gcctgcctct gcctcctgag agcttttaaac ctgacatctt gatccttta tagtaaaaga    3360 ctacagaatc agtttcttgc atgattcagt ttattccaga agacagagct tagaaaagtt    3420
agcaaagaag aagaggtgag acttacatct gcaagtcagc tactgttaac ctgagtggat    3480
cttaggaatt tataaacctt atttatcaaa tacacattat ttatcaaact tgttgtttag    3540
tatttaaaat gttccagaag cctggtattg aacagttagt aaagacaaaa gcagttagac    3600
ttatgtctca atgaagggggc cagctcccct ttcggcagtc ataacggccg aacacgtgct    3660
ctatgacctt gtcctagaca ctagaaagtc agatgcctgc ctcttgacaa ggaaccaatc    3720
agaagttagc tggtggcgct atgctttacg accctgggtg tactttcgga caagcacaca    3780
```

```
gcaatgatgc agagcatagc aaccacccta tgggccataa caaccagttg gccaatcaac    3840
acagggcaag ccctccaagc ctggaggtta caccaatagt gacccttttgc gtaccctag     3900 acactcccct tacgctgccc tataagatct cggtcctgtg gcttctcaga gtcttttgcg    3960
agccctccgc catggagggt gggtgaaaga cccaagctaa catggggtta gctcgttaaa    4020
ttacaataaa gcctcatgca gtttgcagcc agctctcaaa tctgcctggt gatttgggtg    4080
actgtggtcg tggcctggga ccccggatac ctgagttttc cggggggggtc taacaaatcc    4140 aagttacata tatagtattg tctaaacaag aatagaatca ttgctggtct gtggtggtcc    4200
atgcttttaa tctcagcatt tgggaggcag aggcagtctg atttctgtga gttcaaggct    4260
agtctggtct acagaacgag ttccaggaca ggctccaaag ctacacagag aaaccctgtc    4320
ttgaaaaaca aacagacaaa caaaaaaccc aaatacacac acacacacac acacacatac    4380
acacacttat atatgttgca gcaaattaaa attacctatg tatagatttg taaatataaa    4440
ccttttgtta taagttttaa gttaaatttt gttacagatt ttaaaaacat acccaatgaa    4500
tttacaaatt ttgaggttaa caacatagtc ttaagatatt ttttgagaac agaaagcaaa    4560
gaaacagtaa agataatttt tttccagaca gggtttctct atgtagccct gaaactcact    4620
ctgcagacca ggctggcctc aaactcagag attctcctgt ttctgctggc ctagtgctgg    4680
gattaaaggc atgtgtcctc actggctgag ataaaagatt tttaagagtg gaaaatagaa    4740
aaaccttaag agttgagact tttttggaag tgtaggggag agaaagttta gatatgagat    4800
ttggggaatc atttgtttgt gcagtggcag aggttgttac catatgagag tatttgaaac    4860
cccgtaatat tgtcaagttt tggctgttga ttgagctgta ctgagaccaa gccgtttgca    4920 gtaagcacg aggctttaat gaagtctcta agtctgagga agaagagaga aaagggtcat    4980
ataaggccca ggagaatgta aggaagcagt ggggcttcca ggtggaagct gagagacaga    5040
aggaacaagg gtcacagaca gggactccgc ctgagggagg attccaatat tgtagaggcc    5100
cagaaggatg aaaggaagcc atgggactgc aattcctagg gagaggggaa gaagttccag    5160
gaacagtgga gaacaaagga agcagaggag gtgtcatgat gataaggatt tcaacctggg    5220 gcatcccaa tggaactgag agacttgtca gagagaaatg tcctagatca tagagggagag    5280 gcatcatttt ccatgtgata ggggctcggt aggatgagag gagctttctg gcataccagt    5340
gtggcttttg tagtaataat agacaaatta ggcaactcca gggtgacact tactcagtag    5400
aggagaagag acaagtggtt agatcagcta gaggagaaaa cagctggagt ggactaggag    5460
aggcttttgt gagaagggaa ggttccagta gaacagtggt tcccaaactt cccaatgctg    5520
caacccttta atacagttcc tcatgttgtg gtgaccctca atcataaaat tattttcatt    5580
gatacttcat aactgtaatt ttgctattgt tatgaatcat aatgtaaatg tctgtgttttt    5640 ctgatggtct taggcaaccc tgtgaaaggg ttatttgacc cccagagggg ttgtgaccca    5700
caggttgaga accactgcaa tagagggaga ggagtaagta gcagagagat gcccaagtgg    5760
ttgttgccct caagggcaca gcaggcacca ggagccacac agacgctttc tgagtagatg    5820
agaagagatg gatagttaga acaggtggag gggagaaaag aatgaagagg caggctgtag    5880
aatttgtagt caaatttgat gggtggcaga agccaacaga aacaaatgat ctgtacatac    5940
ttcagtagag tcaaatcagc aggttggttc tgttaagaga gaggctgatc caataaaaaa    6000
atggagtaca gatctaaaca gagaattctc aacagaaaat ctcatatggt ggaaagacac    6060
ttaaggaaat gctcaatatc cttagtcatt agggaaatgc aaattgaaac aactctgaga    6120
```

```
taccatctta cactgatcag aatggctaag atcaaaaaca ccaaagacag cttatgctgg      6180
agaggatgtg gagtaagggg aacactcttg cattgctggt gggagtgcaa acttgtcaat      6240
ttctcagaaa attagcaatc aacctacctc aagaccctgc gatacatact tttgggcata      6300
tacccatgta ctcatattac aaggatattt gctcaactat gttcacagca acattattca      6360
taatagccag atcttagaaa caacctagat gcccctcaac caaagaatgg ataaagaaaa      6420
tgtggcacat ttacacaatg gactactact cagcagtaaa caacaatgac atcctaaaat      6480
ttgcaggcaa atggacagaa ctagaaaaaa aaaaaacaca aatgagtgag gtaacccaga      6540
aagacaaata tagtatgtac tcacttataa gtggatgcca gacataaagc aaaagatacc      6600
cagcctataa tccacaaccc tagagaagct agaactctct tccagaaaca gatagaagca      6660
gatgcagaaa tccacaacta accattgggc tgagttcctg gagtacaatc aaagtgaagg      6720
aggagtgaaa atatgaacaa aggagtcaag accatggtga ggaaacccac agaatcagtg      6780
gaccggagct agtgagagat cactgactca ggtctgacaa atgggggaacc tgcataagac      6840 tgacctgact cccttaatat agatgacagt ggtgtggttg gggtaatata tgaggccact      6900
gacaatgggt ccaagttcta actctaatgc gcaaactgac ttagtggagc ccattctata      6960
ccttgctcag tctagacaca ggggtggggt ggggtggaga ggtaccttgg tcctgcctca      7020
aggagatgat gggacagact tagacttcct agggaaggcc ttcccttctc tgaggagcag      7080
atgggaggtg ggggggggcag tgggggggagc agaaggagag gaggaggaag ggggaactgg      7140
gattggaatg caaaaaatta attaaattga gaaagagaga gagagagaga gaggctgagc      7200
cctttggaag gaaggaggat catatgtgcc ctcctgggtt tcgaacatca gatgaatgaa      7260
aacgaaggtg aggacattga ctgctcctag gtcaggctga ggagagggtt ttattgta       7318
```

<210> SEQ ID NO 4
<211> LENGTH: 27456
<212> TYPE: DNA
<213> ORGANISM: Cricetulus griseus
<220> FEATURE:
<223> OTHER INFORMATION: Main cluster coding area
<220> FEATURE:
<221> NAME/KEY: misc_feature
<222> LOCATION: 25795..26498
<223> OTHER INFORMATION: /note="n = unknown"

<400> SEQUENCE: 4

```
tgctgtgcag gctggtcccc atggtgaccc tggcagagta ctgggggtcc cattctgcta        60
gctctcagat ttcagtgggg tcaccatcct catctccctc gtgccgcctg gtgaggggct       120
tcacactggt gcttgtgggg tggtgttcct ggctgcagct ctggccctgg ggagcagggt       180
gtgccgctga ctcaccacct gggcatctgg gcctggaacc atgggtgagt cacccagcac       240
tgggggagca gagagaggct gcttgaagtc tggagaggga agagaactgg gcccacagga       300
agggtggtgc ctactgggga tgggataaag agcagaaggg ggcagtgtgg agtctgaagt       360
cttgaggtca gctcttccct gaggcccagt tgaaggacac agtgtttgtt tttctccatg       420
aagaagacac tggggacagg tgagggcctg agggatagcc atggttgggt tcaggctcct       480
gttttcagct cggggttggg gagccattcc cacccactca cctttctgtg aaagaaagaa       540
gacgaggttc atgtctcctt ttcttcctct tttgcattct atacagactg ctgctcactg       600
cgtctgtgcc tggtgcggaa caattgccgt tgctcatttt gcagtagttt taagcacacc       660
cactcacttt gctaccctct ttaagaggga ttctggtgcc ggacattcaa aacaaaataa       720
acaccaaaag atttcttaga cctcctgaca tcgtcctcta gatgcctcca gctgctcttt       780
```

```
tggacccggc tttctaaggg tggcctggac tgattctctc catctctttc tgtctctctc    840
actcacacgc acatgcaccc atgagcacag gctgtgaagt ttcctcccac cctgtgtccc    900
tgcaccctct gacacaggac ggagctgtga ctcacaggca tactatgaga accaggcttg    960
gaatgattct ctaggcccca gaaaaaaagc tgtcccccca cccccacccc cagtccctga   1020
ctaggctccc cttttcccaca atgcctctgt ctccttgctg aggcctgggt gagctcaggg   1080
atgcccttgg ctgggcctgg aggatcctcc agttggtgct gaggccagta ctgtctgaga   1140
gggagtggac aagagggagt gagcccagta aaggatgtc agattttatc aagatcaggt   1200
tgggacaggt tctgtttccc aaaaatgaca aactggaggc cagtctggca tataattccc   1260
tgcccttgga gtcttggcta ctttgctccc tcctgggcat ctctgcaacc tggttgtgag   1320
tgtctctgtc ctacagagga cctgggtttc gatctttgtt ccgatatctt gatccttgtc   1380
catgtagttt tctctgcctt ccaagtggga tctcccattt gaaggactct ctgtgaagtt   1440
ttgaatggga gggccttacc cagattcctc tgccagggct tagtggttaa tctgtggtct   1500
gttctcctat ctctgggaga ggtctctgtg tttctcactt tagatatgtc catctacagc   1560 cccattttg gggtttaggc ctaggactag gtcatggtta tgtaaggagg cttttataa   1620 gaatccctag tttgagccag atgcaactgc aaaggagtgt atttgtaatc ccgcactcag   1680
gagactgagg taggaaagtc atgaagtcaa ggtctgactg gctgcacag caagatgttg   1740 tcacaaaaac aatcaacact aagtttgttt tgcttttgct tttgcaaagt cctggattct   1800
gttaggacta agaagccaaa gatagacttt cagtgcttag ccctgactgg ttcctgggcc   1860
ctgtgtggtg gcagagcctt gcccaaggct gcttccggtg cttttcaaag tgggtgaggg   1920
tggggctggc agggcagggc aggcctggca gggaacaccc aaggctcctc tggccttacc   1980
ctggaaccca cccaatattt ttagaggaat ttggaaaaag tgacttctga actctgacct   2040
catctcttca gcatctagcc tgatcccaag atactagcca tttacatttt ttagttctaa   2100
ccccaacaga atccttcctg atggggaggg tgttcagtct cctccatcct gccatctgtc   2160
tgcaaagagc ctgcctgtca cccagaggga gtccctggtc taaaggagga agcattcctg   2220
cctaagggag cttcccttta gatggcagag actctgattt tagtagatta gagtttgggc   2280
aaaggttctg cctcttcagg gagcctcata cttctggact gttcccatgg ctactgccaa   2340
gctctacatt cctggcacag ataggagtca aattgagact ctagtcatcc tgcaacctcc   2400
tcctgtcccc tctctgcctc ctaaagacac tcaagtaggg aggcctaccc tcagaagtgt   2460
gtccttagga cacaaggttc tgctttatgt gactcccaga ccacaggaga ggtttaacat   2520
ctgattacag tgtgaagcag cagtgtggac ccgaatcctt ggggaggcac agttccaggg   2580
caggatgcag gcactgactt gccattccta gaggggctta gtggagcaga agcaggcctt   2640
gtagactggc cttgtagact gttcttttgt gtctcaagat ccaagatgtc cagtcccctg   2700
gaagaggcca tggatgtgac ggtctccacc ttccacaagt actccagtca agagggtgac   2760
aagttcaaac tcagcaaggg aaagatgaag gaacttttga taaggaact gcctagtgtt   2820 gtaggggtaa gtgaggcagg cccaaaggga agagtcccgg agagtggggg tgggggcagg   2880
acacaggaca caggacacag agtaaatctt ttccagcttt cattctcaag gtgccagtgc   2940
cagggtgggg ctcaggatct ctctatcagc tttcatttca cctgttcttg gggtggctgt   3000
taggtctaca tgtgaatggg cttattgatg gctgttgcct tctgtattcc tgagcacatt   3060
gctgttgggg acttcagagt ccatcagtct aatcctgtta tttgctagtt gaacagtcac   3120
```

```
aaactcacag aagggtagca gctggcccag ggtcacagga ggacataact agggcattaa    3180
tttctccttt tattttacac atgtatatgg caagccaaga aagtgttcag agagaatgaa    3240
ttctagctaa gacatgcacc ctgggacttt tgcaaatgag atacagctag ctctcatttg    3300
cttcctgccc tagagtcagg tctcaggccg taatatatga agcaggtttt tttttttttt    3360
gcttcatttg gggttagctc tctcattgtt gtggctggat taaaaagttt gtcttttctg    3420
aattcatcct gctgatgcag ggggcagaaa gctttgattt ttctcatcgt caggatgaag    3480
ctgggctcta gtggaggttg gagttacagt ctgaggaaca cccagcatcc ttcactccag    3540
caggagtgct ggagactctt atatcacaca tctgtctgtc tgtcctcact ggccttcttg    3600
gtacctcact ggggtcgaac ctgactgtcc agtgaggaga ggacactgga ggctgctgta    3660
aaggggaggt tttggtggtg ggtagggcag ggaccagctt ggtgatagct cccctgcctg    3720
tcatcttcag gagaaggagg atgaggaggg gctagagaag ctgatgggcg accttgatga    3780
gaacagtgac tggcactgtt tctggcactc attgctatga tgtgcaatga cttcttcctg    3840
gggtccccag cctggccctg gagtagagag ctccactctc tgtcacatgt cttcttggct    3900
aacgggctc tctatctttc tgaatcttgt actaaataaa cttttgtttg tttgttcatt    3960
tgtggatgat attgcaatgg ctagcgatgc tttgtgcttc tgctagatca gtcaaagggc    4020
tggaaacaga aattgctatg atttccaaaa ccttctgctc tccaactctc ctgaggccaa    4080
aggctctgct cttttggatt tcacataaac atcaagaaag tgggcttctc tctttttatt    4140
accatgaaca aaggccattt gccccagagg tcctgcctgg ccttgtctcc cagccctaca    4200
tatgtagaga ggtcagagca ctgagagcaa gtggctgtcc catggtttgt cactgggctc    4260
catcctcctc ttcagagctc tgtctgctct actctgcaag tggcccacac acatcagagt    4320
ttcccaggga aaagagaaaa cagtcagaaa agcactgcct ttacttgtgt ttttatggtt    4380
attatccatc tcctctttta ttaaaaaaac aacagctttt ttccccttct cttaagatgt    4440
caacatcccc agctagaagt agccatatta ctttgctaag ccccaaaaga tgtaggtgaa    4500
gccctgcaca gagaggtcat ttctgccata ttaacaaggc aaaggctctt gaggacaaag    4560
tttttcagct ctcatcatca ctctgtcttc cacctagagc atggacaatg agacttggag    4620
gtatagcagc cgtgttgtga tcaggaatca acaaacacgg tatagcggaa cgtgtgttgt    4680
aggtttaaag aacaaaacaa tgaaaggaca ctagatttca catgtgtccc tgggccctct    4740
acccaacccc aactacctac agcagactta ttatgtaaaa tgattaaaga cactgtcagc    4800
caagttttct acaatttacc gctgaaaata aaactccaaa ttagtaaaga atttgacatt    4860
gtggatatat atttgtgtgt gtgtgtgtgt gtgtgtgtgt gtgtgatgag ggtgttgtgt    4920
atgctgtggt gtacatgtga agattagatg acaactcctt tatgtgggtt cctcctgaat    4980
ctgatttgtg caaatctcaa tgatttgtgc aatgaataaa ctacagcaga agtgatacag    5040
ctccctaagg tatgtcagaa gctaaggggcc atgctctgag aagcccacac tatgtgagga    5100
gacaagttgg acctttcttc cctgggactg tcctccgtgt gtgagccact ggagagtag    5160
atcacacaga gttctgaaga ggaggcaggg gcccggtgag aggccttgtg acagcaactt    5220
agtctcagtg ccctgtcctc cctacacatc tagggctggg agacaaggcc aggcaggccc    5280
tctgggacaa atggtttctt tccatggtaa taaaaagaga gaagcccacc ttcttgacac    5340
ctgttggaga gggatcggta agtatgagag tcatgatgcc agtaattagc atcctggggc    5400
agttctcaaa gctcctgtga gcacactgtc atttcagccc catggtaagt ccaaggggc    5460
tatcattaaa gctttttac agatgggaaa gcagagaggg gcagcttcag ccatttgtgg    5520
```

```
agtgctgctt ctgactaggt acttggccta ctcatgcagc agccatttaa tcctcaccat    5580
acctgtggat gaaacagagg ctgcaagaca ttaaggacta gtgtctggac ttgacctaaa    5640
tctataagaa aactcctcat ccctgtggga cactgggctg gcagactggg cctctttcta    5700
ctttctgaag ctatctccag aactttgggc tttgtgtgac ctggagggga cctggctgaa    5760
tatggttcag atgtacccgg tacattaacc cggagtcaca gggagatggg acctccttgc    5820
aggtggtttg ctctgtgaac tctaattttt cttttagtgt tgcatgggtg caggctcctc    5880
ggttttggat ttgacagtc agttgggcta gcaagaccag acttaccttg ctgcctccaa    5940
ggtttcacac acttggagag gttccaaagt ggctaaacat tccttttggt atttgacaaa    6000
ctgacatcag actgttgaat ccagactaac aagcctctct cttccttgtg ctgaggcaga    6060
ggagggtctg gacatcactc tgcttgtcag ggatctgtgg ccagatctcc cccactcctc    6120
ctggaattgt gctgggatga gaaatgtagc aagctcacct cctgttatac caccatttta    6180
ttgtgtggct caaccacaga aaggtctcta atgtctgtg gaaggaaga ttgaaggcca    6240 aggtgagtta attgccacat ccaagctgat tgcttgctca gccactcaga ctggagccca    6300
gggaacaaga caagtaaaaa gtaaaaagat ctagtccaga aaaacagaag gatggtcgga    6360
tagacatcac cttaatccag cagtcaaggc ccttctatcg ttaaacaaga gggaaagatg    6420
ttcgccatag atagggtgg ctcccgattc cctgtaccct cctcgtgatc tggagtagga    6480
cattgtgcag tcacaaggca gtgatgtgtc tgtgaatctt gaaaacatct tagttactct    6540
tatcttggtg tctttagtct tggaccggga ggaaagaggt tagggtaagt tgctcttgtc    6600
ctgggagtcc aggcaaatat tcaccaaatg actaatgtgt ctatgtgcat agttcagcag    6660
aatctgaccc aaaggttaag gcagcacagg agacaagcac aaatagtgga agcccctggc    6720
attttcaccc ttatttattt atttatttga dacaagacat tgctatgaaa cctaggttgt    6780
gctcaaactt tcagcgatca tcctgcctta gccttcccag ttctaagagt agagcatgca    6840
gtgccaacct tgattgtatc ttgtggtagt catccattag acactcccga ggaccagagg    6900
ggcagtgtgt acagtgaagt ggcttcccta ggtgactttt gttttgtttt tttgagacag    6960 ggttctctg tgtagccctg actgtcctgg aacttgttct gtagatcagg ctggcctcaa    7020
actcacaggg atccgcctgc ctctgcctcc tgagtgctgg gattaaaggt atatgtcact    7080
ggtgcccagc acctaggtga cttttgtagtt aattaaatcc gtgtgtcttt tacatcatga    7140
atcttgatcc cattcattcc ctgtcccttc acatcagccc tctgcccta cacgcccctt    7200 gaaataaaac aaaatttaag agaaaaaga aaaaattaa gggaaaaatt taaaatatct    7260
cattatggaa gctgcagtgt gacccagtga gccacacagt aaacacatat agctttactt    7320
gcaagtgttc attgcagagt cattggtctg gttcaaggcc tctgatttct actacactgt    7380
caacactggg ccccactagc gctcttcttc catgccctgt tgtcgccctg tgttgtggag    7440
gtcctgcagc attgggtctg tgggtctggt cccttcgtgt gctccagcag atcacagggc    7500
agaccaaatc ataaccctgg gtctgggcct gagcaactgt gtagttggtc cgctagatga    7560
gaactaggga aagctctccc atgtttacaa ctttagggct ggctcgtcca cacctgggct    7620 aacaggggttg gttctctgct cttataccac aggggggcagc tctccctcct gtccctggca    7680
ttgaagggca ggggtggagg gtgggggggga gggtaatagg gacagttctc ccatgcttac    7740
aattctaggg ctggctcacc tatgcctgtg ccaggtgtga tgggccaggt gtgtggtggg    7800
ggctaggtga cttttataat tttaagccag aaatgtcagt tgaattagga gacttgctta    7860
```

-continued

```
gctcatcgcc tccaaagcta ctgattttca aagtcaacta agagcaagca aagcttgaat    7920
ttttagatgg ctccacccct aagaacaccc acataccacc gagttatggg ttctgggaca    7980
atgggatgaa ctggtaccct actccacagc tcccacgtgg gtcacttgat tgctctacca    8040
actcgctgtt ctcatctgtg cagtggacac aaccagccac tggcttgatt ttcagagcaa    8100
gcagtagatc taatctctgc aggctcttct tggtcctagc ttagattctc ttcccttttt    8160
ctagctccaa ttctgtagct tcagctccgg ttcaaaattc ctccctggcc ccagtgctgg    8220
tcccggtaat cagatactcc tttccatatg ttctccatcc ttggcccaga agatcagaaa    8280
ggaggttgat tgtttcagtc aagttaactt aacctcatgg ggccattaga tttgggtggt    8340
cactttggct ttagggctcg ggcccctttg ccagaaataa attgagtgtc cagattcttg    8400
ggacactcta tcttattttt ccctgaggtg caggatcaga cactgccctt tagaggggtg    8460
atgtgttttc cagggatctt aggcgatggt ggtgatagtg aggagccaga ggggagccaa    8520
gggagagtca gggtttcggc ttgtaagaag tcctgccaga tcggctagca tctgctttcg    8580
cctttgcaca ctctcttgct gatcttttga ggtgatgctc ctagccgcat ttctcagcgg    8640
tcagctcacc tgtcctcggg gagctatgca aggtgagggc tcagcctaag ggtggagatg    8700
gagcatgtgt gtgggagaga gtgggaagga aggaggatga ctctagtcca ggccctggaa    8760
ctggtgtcca cttctgcgca ttggggtcac ccgcaagaaa gggcttctgg gtagatgctg    8820
gaaaacttcc aggatgacag gaagatacca ggtactttaa gaaggttttt tgggaacaag    8880
ggaagagaat ttagagtcct gacctccatc tttgtggagg cagaagctga gaaagatgac    8940
ccggtgagga aggtctggtt ccactgttcc catgtaggga attcagtgtg ttctgttgag    9000
ttagacttgg gggccagagc cctcacattg cctcagtaac aactagtaac aaaaagtact    9060
ttgaaaaaaa ttttgagac aagatctcac tatgtacttc tgactggctt gaaacttgct    9120
atgtagacta ggctgggctt gaactcacca agatcaactt gtccctgcca ttcaagtgct    9180
gggatgaaag acctgctcta tcatacaagg caatactttg gattcttagg gtaagaatct    9240
tccaaaccct cttcagagat aaggaaatta tatttctaac aaggaaattc aatctctaac    9300
aaatcttcaa acatgttgaa gtcaggtggt gagcagggat ggaattttga gtgaaggcca    9360
attaagtgtt cttttccatgt gcattaagtg ttttttccat gtgcatcctc caaccccaca    9420
tctctaccaa gacaagtctc ttagcctctc ccagctttct ccccatggac aaagatgcag    9480
tgttcctagg agctgtggct gtgcccagga gcaggaaggg ctgttggata agaaagtggg    9540
ctcaggagct aggctatgga actccagc ttattaaaca ttagtttgtt attgtctgtt    9600
tctcccacta gattgtcatt tcccttgaga gggtctgcgt ctgttttgtt tatgctatac    9660
cccggatgcc tagtatcagt gcctctaatt acttgtatga atagtgaata tcgagtctgc    9720
cactcactag ttacatgacc ctgggtaagt cactacctcc ctgggttagc atttaccaag    9780 tcctactat atttagcaa catttgttcc atgagcctgg cttgtgataa actccacaat    9840
aaccctatga gatggctact actttttattt ccatcaatca ggaaaatcag gtcccaagag    9900
tggagatgac ttgcttaagg tgactggtgg ctggtgggaa taagtcattg acctagaagc    9960
aaattaattg ctggtcatct ctggtacctc cttttgctgc tgtgtgacca tctctgtcct   10020
gtgtcccaaa ctgctcataa ctccttgcca ataaaacagg gctaatcaca gctcttcctt   10080
ccttttgcct ccattgctca ctcccctcac ccacatggct ggcaacctcc aggaggagat   10140
ggtggcctgg gcaaagctgg gtgctgggtc cagggtgagg tcaagggctc tcagactgcc   10200
catacaggca tgagggtttt gtcactggcc aggaactcag gctgctcttc tccttctggt   10260
```

```
gctcttctgg gtgttttttc ccctttcttt tgtgtgtgtg tgtgtgtgtg tgtgtgtgtg    10320
tgtgtgtgtg tgtgtgtgtg tgtgtgtgca cactcatgtg acatggaagc ttaggggttg    10380
ggagtgaaca gagaggaggc agcaggagag gaggattttc acatctggtg aatggtggtc    10440
tgacctttgc cagctaagaa tggcagggaa tgctggacag aattaaaatg atcttttca    10500 aaacatcaaa gaataacaag gtattaagag aaagccagaa cagacatggt gtcacacacc    10560
tttgatccca acagaggcag aggcaggtgg atctctgtga atttgagtca gcctggtcta    10620
catagtgagc tctaggatag ccggggctat gtagagagac tctgtctcat aaaacaaaac    10680
aaaacaagcc ccttgtgtct agagagatgg ctcagaggtt aggagtactt gctgtttttt    10740
gccgaggact cagctttggt tcccagcacc cacatcgtgg ctcacaaccc cctattactc    10800
tagttttagg gcatccaaca ccctcttctg accttcctgg gagaaggcat gtgtaggcac    10860
tcattcacac atgtaaaata aaaataaatg catctaaaaa aacagtttca gaagaagaaa    10920
ggaagaaatg aggaaagtaa aagaaagaaa gaagaaaaga aagaaagaaa gaaggaaga    10980 aagagagact ctaccagaat ctctggagag attgtttagc tgttaaagcg tgtactgctt    11040
ttgcagagga ccagagtttg gctcctagca cccacattag gtgactcaca accacctgta    11100
accccatctc catgggggac tcaacgtctg tgacctctgt gggtgcctgc actaatgtgc    11160
acatcactga tgcacataca caaaagtaaa aataagtaaa aacaacaaaa aacaaaacaa    11220
acacctcata aaaaaactta ggtgatggca aaatctggga agttgagtag ggaacctgag    11280
ggctcttggc aagcctaaac ttgaatttgg gtttgatgat ctggggagtg aggaagacaa    11340
agttggagcc cagggctcac acaggagggg acaaaagtag acagacgatg ccgaaccccc    11400
atggggcaac tctcttaagc taaaaggcaa atgaatgctc tacccctgg actgcttgga    11460 aagttgacct agtgctaagc agagcagcag gctatgaaac cagtttcctc aggagctggg    11520
gacatgccag ctctcacctg aatctgtggc ccaaattcat ccacatcact gggagtagag    11580
aggcaagaaa gttcaagccc tgacagctgg aggctcccca ggaggaactc ccttcctcta    11640
ggtctcgaaa atacctcacc acgatttcct ccagtgaaat aagcaattca cagccaaagg    11700
ccaccaaaca ctctgtgatc tggaggctgg gcacagaggg tgtcctatgg cctcagactt    11760
ctcacctgta aatagggggcc ttagccaggt gttcccaagg tctgccctgt acagggactc    11820
tggaggtaca acttaagaga atccaaggta tgttcccatt ttgtattctg ggtatcttta    11880
tgacaaagag ctcaggagag ggatgtatgt ggctggaagt ggctaccaga aagctgttgc    11940
ctgttctccg ctttagggaa gggcagtggg aatgagttgg gagtggtgtc tgagactcag    12000
actgggtctt tgatctgtgc gttgctaggt gggtggtggg cctgtaatag aagctactga    12060
gggaagaagg caggggaccc tggggggcagc ctcagtgttg acctacttgg gtccttataa    12120 ttgctcccctt catctcttga gaggctacaa ataggggacac ccagttgtta ggctcctaca    12180
gctgagacac cagcagcagt ggtgagtgtg gctgtttggg aacagctttg gctaggtgt    12240 tggggcagct caggtaccta tccacagcta gcctgctcct ggatacaggg cccgggtatg    12300
gaagcagaaa ggttaagtta ggaggtgatg ggtgaggaaa atcagatgtg gtgaactcag    12360 aggttcccctt gaacactaag ggtctgtagg agtttggcct ggggagtgtg cccagcaaa    12420 atgcccactg atgtggggac agtggcctag ctatggttct gatgcagacc ttaagtgagc    12480
tccttgtctc tttgcttcat tcttggggat gagttgggac aggccagggc ttctgaaata    12540
gcaacagaag tggtgccatg caggctggga ggtgctcaga agggctctga ggtgctgagc    12600
```

```
tcttgggatc atggcccttc cctctattcg gatatggatc cttgttccgg cctgggctgt    12660
catgaagaag tagaccccag caatgcttgc cacttctgcc catccccata cttccttgct    12720
gcccatttgc tcccagcaga ggaaactcac caagtcttgg ctctggctgc cctgtgctgc    12780
aggactccag tccctgaggg agtgaagagt gagtcattgg actcacatgg aaacaactct    12840
attgcctctc ggcctgccca gggtttgccc aggctggatg gcaatggaa gggaacaaca     12900 gaaaggggc gagggaaggg attctaggaa gtgcttccct cccatcagag tgggggactt     12960
ttctcaaagc cttctttctg tgttaagact accccaccc cctcagttcc aggggaaggg     13020
aggatggctg taagattggg caggtcataa acgagtagat ctgtgagctg atgaacttct    13080
cagagaccgt ctggtccaca tttctgacta ggcctgtgag gccgcattaa cccactttac    13140
agaaaagaca attgagaccc agagagaaac agttcaccca gggctgcaga gtgagcaaga    13200
ggatgagggt ccccaactgc agggaagaag gccaagtgag gtggcagggg atcccctcaa    13260
gctaccatcc ctactgacat tagcctcgct agggcaaagc agcactgggc agggcttcct    13320
gagcaaggct tacaggatgg agcttcaggt gcccatgggg cagaggtatt taggaccagg    13380
gactgcatcg tgcccaatgg ggagacagag ttcccaggag ttggggtgag aaaggacttg    13440
agggaatcag agctcagtga gggtgaaggt gacagagtgt gatattctgt tcctgaggaa    13500
tttatggaaa tgttggggaa atgaaacgtc tgtccagaaa aatcacaaca ggcacaatgg    13560
ggaggtgaat cagtgtgggt atgtgtggta tgtgtgtatg tggtgtgtgt gtgtatgggt    13620
gtgtgtgtgt gtgtgagtgt gtgtatgtgc ggtgtgtgtg tatgtggtgt gtgtgtgtgt    13680
gtgagtatga atgtgtgtat aagtcatgtg tgtgttgagt gtgtgtatgt gtggtatgtg    13740
tgtatgtggt gggtttgtat gtgtgtatgt gtttgagtgt gtgatgtgtg tatgtgtggt    13800
gtgtgtgtat gtgtgtgagt atatgtgtgt gtgtgagtgt gtgtatatgt gatgtatgtg    13860
tgagtgtgta tgtgtggtgt gtgtgtgtgt gtgtgtgtgt gtgtgtgtgt gtgtgtgtaa    13920
gcagttgtca aggaggggttg ctcagaggaa gggaaacttc agcatggtgg aagttgacag    13980
gtttggaatt agctcctggg aaacactgac ttggctttcc ttgtgagtca catccctttt    14040
ttgtgacagt gaggatgacc cggcccctgg agcaggcagt agctgccatc gtgtgcacct    14100
tccaggagta tgctgggcgc tgtggggaca agtacaagat ctgtcagtcg gagctcaagg    14160
agctgctgca gaaggagctg cccacttgga ccccggtgag caccttcata ccccttcccc    14220
ctagtggaag gtaccacttg gactctgcaa agaatggcct gggaccaaac accagcatag    14280
ggcagcaaga gggagaggct ggactgtgga gaggggacac gaggaagtga gctgacatgg    14340
ctgcatgagc ctcagcaaaa tggaatgtaa agtagggtga cagggccaga tgttggtggc    14400
gcacgccttt aatcccagca ctcagaagac agaggcaggg ggatatctgt gcgtttgagg    14460
ccagcctggt ctatagagca agttccagga caggctccaa aacaatccag agaaaccctg    14520
tctcgaaaaa ccaaaaaaac tgaaaaacca aaaaccaaa aagaaacaaa acaaaaccaa    14580
aaaacaaaaa aggagggtga cagtcactct tactgtcctg tggataatac ctatctcata    14640
gcaaactctc catggcaagg agtcggtgct cagcaagtga gccgagaagc agggctggga    14700
gatgggtgtc ttatcaggat gggtaggatg aggttggccc ccaggagggt gtggttggga    14760
atggggcagg cccacccctcg gagggagtg gcgtggaaag ctgcttaggc tcctcatccc    14820
aggtttcctg accttccctt ctcatccctt ccacagagtg agttccggga gtgtgactac    14880
aataaattca tgagtgttct ggataccaac aaggactgcg aggtggactt tggggagtac    14940
gtgcgcgcgc ttgccagcct ctgtctctac tgccacgagt acttcaaaga ctgccccct    15000
```

```
gagccccctt gccccagta gcctctgatc cagaaggta tgccattctg aaggtcagg    15060
gtctgctcta gtgctccgtc tttgtccctg aggtgatcct gagtgtgtag ccacacccct 15120
cctaccctct ctgtggtatc ctttcagtcg gggcttgcca ggtccctgat gtgctaaccc 15180
tggctactca tgcacagtag aagctttcct agggatgtca agtagtgag gggtggaaca  15240
gtagcttctc ttcttggaag ggagaacatt tgctctctca ctttggaggc tcagccatgt 15300
gcacactgtg gcaggggcct gctcaactcc taataaagaa atgtcagctt ggcttggttt 15360
ggttcttctg atgggacaca ctggattttg ggactgagtc cttgggagtc tttacccctc 15420
tatgttccat atcgctggag gaaggcagct gaaggcaggg gccctaaagg cagttccaga 15480
ccccatagga atgcataagt ctcagtattc agtaggaagg tggggccatt acaagtcccc 15540
atcaggtgag gctgggggtc tttgtctcca tctctctgtc ccctgtcttg aggtggaagc 15600
ccttgttttg ggctttctag gagggcaaga ggctccttgg gagaaactca gtacttgtga 15660
ttagagcatc gaggtatgtg ggtatgggtg tggcatagct gtgggaaacc agagagcagt 15720
agcaatagga ttggggcctc tgaggtattt gctgccagcc agggagggag cctctgtatt 15780
tactgcaagg ggaaagggat actttgagtc agtcctcatc tctgaaacca cagcccctga 15840
gggtcccaag ttcccatttc tgaccattgc tcaatcccg tatttgtacc ccatccttag  15900
agattaatcc tgactcccca ttttacctgt ttctcctgta actctcttct ccaagctgag 15960
tgttcaaacc tgaatgctcc catcagcccc aatacCctcc ctggaccttc tacccattca 16020
tgaacctcga ggcctcatta ctgccctaac tccatcacgc cctcttaggc gtttcccact 16080
taatacctag ggtggtacca aggcccctcc cgacttgcca gtcttcactc tgggtcttac 16140
tgagcgtgac agagagctgt ttaggctgga gagaagggct gactgtccca ctggccgggg 16200
tcacctcccc aattcctggg ccatacattt ccatattccc ctcttgccca tcacctcccc 16260
atcttctttc ctgtggccca catcccatgc ccatgttgcc ccttctcaaa gcttccttaa 16320
aagttggctg agctgtggct actgggtggt atccacacca ttcaggtctc tcgtgtccac 16380
tggggcttac tcaatgctcg cctgtgcctg ctgggtagta ggaagcttgg ttctcaggtt 16440
gggctggtgg aggggcctgt gacatttact acatcagcca acagtaggaa catagtatcc 16500
aagctccccc catcccctgc atgggcaggg cccagcagag tataaatagg gcagacattt 16560
gagctttccc caaacctctc tgttcagcac ttcctctctc tgggtctggt gagttgtgtt 16620
ggcttcatag cagtattagt ggtgtcagag gctgaggctg ggacaggaga aagggaggct 16680
tctggggaga cagatgtttt tactagatcc agatgagaga ttctgatgtg gaggctttgt 16740
gtgtgtgtgt gtgtgtgtgt gtgtgtgtgt gtgtgtgtgt gtctgtgtgt              16800
ctgtgtgtct gtgtgtgtct gtgtgtgttg cacaagaatg aaaacagcaa caaaaaggtg 16860
tatagatgcc atttgagctc tcaagatttc taagatgctg aggcttacac gtgttgttgc 16920
tacagtgtac atctgtgttt gggagccatg gataggtacc ctgatgggtg tttgctgggt 16980
cattcaagcc agtgtgtgcg ggaaagcagg tgcaggaagc aaagtgaggg aacatgtagg 17040
ctttcttctt aacgttttaaa cttcagttat ttatttgtgt gcatgcatgc gtgggttggg 17100
gatgggggc tcatgccaag gtgcacttgt ggaggtaaga gggcaacttg tgggagggag  17160
tcagtctgct ccttctacca tgggctctgg ggatcaaact caggccatca agcttagtgg 17220
caggcacctc tacttacagg ctaccactcc agcactcacc tgtagacttc tgtgttcata 17280
ttagtgcctt atggacatcc agcaccccag gtcaagagag cctggcttcc ccaccctccc 17340
```

```
cttgtgcccc tacctctgcc acctcatctc actcctcact aagctggtca ataggcagct   17400
gggttttttc cgctgtgggc ccatgggcag gcagccagca gccgcgccca atgctgggag   17460
ggggaagaac gggccagagc ctggtgcttg tggttgagct gagcaaggac ggaaaactgc   17520
tgttgttgag gccaggcccg aggacagtca gcccaaaagc tgctggcacg aatctccaga   17580
gattgtatgg taggctctgc atgtttcaga gcccaaagca tacacgacca tcttgccatt   17640
agtgggtccc actcctctga tctctctggg aatgaggaca gtctcctgaa gtgttcctag   17700
agggtaggtt ggaatggagc atttaaaatg ggggcagaat gagtctatga cttgggtgat   17760
gagcagtgcc acatagccag ttcttgatac actgttggtg tgggttgggt aaggctacct   17820
ttgtgtctcc tgcccctagc tctcaactgt caccatggaa tacccttag aagaggccct    17880 ggatatgatg gtgtctacct tccacaaata ctcaggcaaa gagggtgata agttcaagct   17940
caacaagtct gagctgaagg agctgctgac cagggagctg cctagctttt tgggggtgag   18000
tgggtcctgc ctgtgtattt catgtgtggt gcatccccag gaggaggttg ggactctggt   18060
aggtagtgcc tagctacagt tggcgtatat ctctaaggtg gggaaatgga ggttggagag   18120
cttgctccgg gtgcttggtg tggaaccaca gtgaaccatc tatccctcat tagccctcag   18180
ctgagagaag gcttagaatg aacacaaccg aagagacaga gaaaaagcaa aacaactgcc   18240
taacatagtc agtgtctgaa ctgcaggcta gatcaggact gttggcaaga gaaattgagt   18300
ttctgtttgt gaagacacga tggtggaggc acacaaacac ctgcagagtc tctcctcaat   18360
aacaccttgc attagttaat ttaatgcatc actgccatgg ctgctaccta atgagataat   18420
taaagcaaac aaggagaaga tgtggtcctc cccgttccca gctacctcaa gtgcccgcat   18480
ctagggcaca tcctcctcta catagcttag tcccaaggct tcctgagtgc cagaggcac    18540 tcaggtgttc ctgaacacct ggctggaggc agagatctag cttgggtctg gcttctaact   18600
gttcttcttc tactcccaga aaagagaga tgaagcagga ttccagaagc tgatgagcaa    18660
cctggacagc aacagggata acgaagtaga cttccaggag tactgcgtct tcctgtcctg   18720
cattgccatg atgtgcaatg aattctttga aggctgccca gataaacagc cccggaagaa   18780
gtgaagactc tgcagatgaa gtgtgggggc gtggtcttcg ggaggagggg gctcttccct   18840
tttggctctg agcatagtgc cttactctgg cttcttcata catatgcaca atgctgagcg   18900
agttcaataa agagtcttga aactatgtgc tgttgcctaa gagactggag attgtgggtt   18960
gggtgttgag ggagggtata tcacagggta gtggtgggga ctgcggggag ttgagctggg   19020
agttgagcct tgagggaaca aaactagaaa gggttgggta ggggttgagt ggctgattta   19080
actagcatgc aagtgtgtgt gtgtgtgtgt gtgtgtgtgt gcgcgcacat acgtgcaaca   19140
aagaaaactt tgggaatact taaggcagaa gccaccagag gcttggcttg aaaggctcca   19200
gatgtgggaa gttagccagt ccaccaccct cctttctctc tccagatctg cctctgggct   19260
caaactgaag ttgggatggg attgaaggtc acatctgttg ctggttggag tctggaggga   19320
agacaacggg cctgagtcac aaggaaggag tccagaagga tggggaggtg gactggcacc   19380
catccctgac atttatagtc caggtcctgc cctgctaccc attctagctc actagctcca   19440
aacagtggat taatccttc ctgtccatgg ctggatgaag aagggcagta tagagagatc    19500
atttgtgaga acataaatct ctctctctct ctctctctct ctctctctct ctctctctct   19560
ctcagagaag acgtctcact cttgtagcca aagctagctt tgaacttctg atcctcctag   19620
ccagcttccc aagttctggg attacagacg tatgctacca tggctgactg aaatagccat   19680
tctcttaaca tactgtcccc atactcagag ggctctggga caggatctac tatttcttag   19740
```

```
aatcatgttg cttagaggag acaagggac ctcaggaaaa taggtggggg tgggtaatgg    19800
cagtgaagca gatgatgggg agatgaccat agttttagac agagttttgg ccatatgatc    19860
tgacaaagaa aatcgagatc cccatatcct cactctctca cccctagaac atgaggcaaa    19920
tgttgcttct ccttagggta ggcttacggt cagtggttcc agagtgccaa gaatgggact    19980
gagattagat gtaaagccct tgcctctgtg atacagggat gcttaaggaa aggtacccac    20040
aagctgtctc aaggcaggtg agtttgctct ccaagcttcc cttctcatca tatctgcttt    20100
tcgctccagc ctcaggggag tggggtaggt gactcagttg ttcccttgga gtttgactat    20160
agagacttag gtccaggcta agcaagccca tcttctcttt ttttgcactc ccagtcaatc    20220
tgcccatctt tcatgggagt gtgctccccg gagcctcctc ctgcatcact ctctactttc    20280
ggaaactcct gttgcttaga gacaagtctc tgctgtatca ctcgtgtaat agctgtggtg    20340
gagtgacaaa gggggcagtg gagaggaact aggcaggcta gggtggaact ttagccaaga    20400
ttaggggtta tgcccctaac caaattctgt tcttagagtc atcgtgttcc cagaatgcag    20460
gaaactcacc ttgagccctg tgccacccat gcgtgactgt acctgaaact ggagcctctt    20520
ccacagtctc aacctagtcc tgaacctttc tttgaccctc ttccccaacc ctgaattctt    20580
agtcctctaa cccaggggtc ggtctctgac aactacttcc catcttttgc tttgtgttag    20640
ctagtgactt cagatgactg tccttggcag gaaatatctt ccttcactga tcccatccca    20700
agaatgggtc cttgtgcact tggaagggat gccaggatgg agggtctcaa tgtggagagg    20760
tatgggagga tttaccctgt gtttggactt tctactgttt cttttctgga gagcccaact    20820 tgccttttc aacctattac ttcaccggat gtgaggttta gtaggaaaac gtggttcctg    20880
gtattgaaag tgtgtctgtc atggtggact ccatgtgcta cctccagccc tgttggtaaa    20940
cagcaagtca aacttttccag agagggttcc cttccaccct ttctggattc ctcatatctc    21000
ggatcccttc tcattggtcc caccctcct gattctcctg ggctttgggg atgagggaat    21060
aaaagcagag agcattggta gggaggctgt ggctgcagcc tagattctcc tctgggttta    21120
cgtcttcctt ggtgagtcct tccttcggat gacctcctt atttctgctg gccagcctg    21180 ggtgaggaag aatgtgacaa gacgtggaaa cctccacaaa gaaggcctga ccttgcaagt    21240
gggagcatgc ttaggagga gaggcagag tatttgtgat tgtgactaag gattcctga    21300 gaagccaact ctaggagcaa gaaagctgag gcaggaggat catgagtttg agagtagtca    21360
taggatttat tgtgagatac tgtctcaggg agagagagaa gggaagagga gggaggaagt    21420 cgggggagc agagcctgct agcagaatca gcaagatgtt tctacagatg cttagagtcc    21480
ctttcttgcc ttgaactgtg gtccagctga gcctccatga ggtgggagaa gctgatggtg    21540
tgggtggcag gagatgaatg atgggctcag tccagctcaa gaacttcttg ggttggaggt    21600
aagagtcagc aatttctccc caccctccta cctagcccag ggttctccac cagatctaca    21660
gaaacctcca gttctgtggc cattgtttcc ttcccctta agaggaagtg gttttttaaac    21720 ccgaaccaca caagcttcag ctgtctgctc ttttggtggc gtgcctatgc tgacagaact    21780
gaagccatta ctcaaaccca acctctagag ccatatctca taagatcctg gccatgtcga    21840
tacccaccct tccccgcccc tgtcaggctg tgggtgaagt tctctgggca tcagactgga    21900
ggtcattagg caagtccagt cacctctctc ctgcttcctg ccgagatctt atctcccagt    21960
ttcagctcca ccccctctg acccctggac tccttttttg ccccctcccc ctcagtgaga    22020
cactctttca tttccagtga ctcagaggct ggagaaagga aggtgactag gtgagaactg    22080
```

```
tggctggaaa gccagagcct aaacttcatg gggaagagaa aaatcctgcc ccctcatctg    22140
ttgtagcagt tctttgggag aggctgtcct ataccctctt tgttcctgga cctctctgtc    22200
agcacctctt gatcagggaa gcctgcagcc tcctttgggg gctggacatt ctcactgctt    22260
tggctgggcc agtatatttg tcatggctct cattacaacc tgtctgtata tacgggatat    22320
tctcattggt gggatttggc ctcactatag gctcctggca atggcggttt ggaatggctg    22380
gtgaggagca ggcctagttt ctctagtgct cattgtctcc tctcccactc cagagttcac    22440
gtcgtgatgg agactcctct tgagaaggcc ttgaccacca tggtcaccac tttccataaa    22500
tattcaggga gagagggtag caagctgacc ctgagtagga aagaactgaa ggagttgatc    22560
acgacagaat tgagtcttgc agaggtaggt gactgttctc tcatatacca cactacacat    22620
tctgagtacc ccttctggga gatgcccacc tacttgcagg gaactctagc ctaggcaaag    22680
ggcaggatgg ctgaagggcc agaggcagag gaagtggtgg acatctctgg ctaccaaggc    22740 tctagaccte tgtgctgggg gatgaatccg tctcactgga aaggaggcaa ggctggggtg    22800
tgctactgcc tatgggaagc tatgggatca cataaaggag actttggtga tgggttgcat    22860
agcctatgtt agggatcttg agggtttggg ggatgtgggg taccgggttt ggctgtgtac    22920
aactcaagga tcaggattct tcttgattct tctctgtgcc tggcacagct aaggtgctaa    22980
gtgatactgt caagtaaact aacaggctaa tttatgaaca tggggtagga aggagacagc    23040
actgattcct attagatgga catgatggga gttgtggctg gctaacttga aggtctatga    23100
gatagagtaa ttgagcctta aatacatcag agaacttgtc ccttgaggct gagctgaaat    23160
tccaggctag tctctgcacc aacctcctat ctatctttac agtgaagttc caaattccac    23220
tgttccccca gggagagggt tccgggaaca tgtccatggg aagggggtgaa acaggtgcca    23280 ctgttctcag gtctctctgc ggcttcccca aggcatatgg agttcaccat gccttatata    23340
ttattctttc tttccttttt gagacaaagt ttctctgttg tagccttggt tgttctggaa    23400
cttgctctgt agtccctgac caggctggct tccaactcac agagatccac ctgcctccat    23460
ttcctgagtg ccactgtgcc tggcctggca tatacatatt caataccaga aaccactctg    23520
ccatcctgga actaatgaag gtagagggac cttttggtcca tcaggtgcta attactcagg    23580
gacagagccc cagggggagga gtctagtctg gggaccagga tcatgttaca gagaggcagt    23640
ttccagcatc ctgggtatca acatcctgta tccaagggag acctggaact gaactgatttt   23700 cgacagaggg agagcagggt ctacctgctt gtattttctt gctccaccct aaggctctgt    23760
cttcaacttc ctagaggagc cagggtacag ggaccaaact gagaggacat ctggtgccag    23820
gctggagctg agggcatgct ggcttctcag ctccagtgta ctgatcttac agagaagtat    23880
atagtgatgc ctgggtcctt ttccagcttg gccttacaat acggacaggt taagttggag    23940
acttggatga tgctcagggc tacagagcca ggactcaagc tgttttttagt agatatctgt    24000 ataaattgta gattataatt tctttggatg ggaagatgtc ccaggagcaa aggctaggct    24060
agccttcctc ttgtaattca tttaaaatca gcactcaggt catggacccc atttggtgtc    24120
aggtcccgtg taaaggtgtg ggttgggggct gagctgctga gcagtctcct cccctgggc    24180 ccttgcagaa gatgaaggag agcagcattg acaacttgat gaagagcctg acaagaaca    24240 gcgaccagga gatcgacttc aaggagtact ctgtgttcct gaccacactg tgcatggcct    24300
acaatgactt cttcctagag gacaacaaat aagcacggtc ctctctaccc acacctgcag    24360
ctccttgtct ttccctctgc agcctcttaa actgctcctc ttacgcccct ggcccttctc    24420
tttctcatgg gtggattctt ccagtagaga aataaagccc tttccccctt tccatgtgtt    24480
```

```
ggttttgagg tggtttgtct ccgttggctg agtcagggga gaacagacag acattttgag   24540
ccattcagcc tcaggtcaca cacaggtggc ctgtgggtgc aggggtgga ctttcacccc    24600 actccactgt ccgtcctttg ttgtggacac tgttgaatgt gtcctggctt tgttctgcac   24660
tgtaaaacaa caaagctggc ccaggcattt gcatgctttc ccaggcagta aagacacaga   24720
gaaaacaatg agaaaaagcg tgttgggagt gaggagacca gggtgattgc agtgatgccc   24780
agtgggtctc agttggggca cagcccacag gaggccactc tggcagccct agtaaaaagg   24840
aaagacacga acttagcacc cttccaactg agtgactcca ggaggctaat tccccctccc   24900
tcaacttcct cttctgaaga cttttcttca ggaggaaacg ttcaaaactt ttcacttaag   24960
atgataagta agcatgctgg ctgggctggg ctccattgtg tgcacattaa tttgtaagct   25020
gctctaaaga tgaacttcca ggcagtgagc tggaagaagc gagttagaca gaaatttatt   25080
gttggtgggg gatggtgtct gaaatccttt agactgtgtc cctccccctt ttttgagaca   25140
gggttttata tagcccaggt tggctcagaa ttctgcctcg tgggatcaac ctactgagct   25200
atatccccaa gtcttaaact agtgaggtca aaccaccta tcagaggggt tgcctaagat    25260
catcggaaaa cacaagtatt tacactgaga ttcataacag tagcaaaatt acggtgtgaa   25320
gcagcagtga aaataatttt atgattgggg gacaccacaa catgagaatc tgtgtccaag   25380
ggtcatagaa ttaggaaggt tgagaactat tagccaatct agtagaccac taggggcttc   25440
ccctccttcc ctggagctga ccttgccacc agagggcgac agcatcagtg aggttcccac   25500 tcccctcac attgatgctg actttaggga cacattgtgc tctgtctggc agatggccca    25560
gcacacatgc cggagtcacg agtcacgtgc cataagggca aactgaagta tggaaattag   25620
ggaaaactcg atgtctctgg tttgtgctgg tctcccagac cagggtcact aggctccctc   25680
atgccactcc caatccggga cagtcctggc agcagaggcg tggaaaactg aggggttgt    25740 tggggtgtgt tttgctagcc tcaggcgccg ggtggggctc ggggcgggc ggccnnnnnn    25800 nnnnnnnnnn nnnnnnnnnn nnnnnnnnnn nnnnnnnnnn nnnnnnnnnn nnnnnnnnnn   25860
nnnnnnnnnn nnnnnnnnnn nnnnnnnnnn nnnnnnnnnn nnnnnnnnnn nnnnnnnnnn   25920
nnnnnnnnnn nnnnnnnnnn nnnnnnnnnn nnnnnnnnnn nnnnnnnnnn nnnnnnnnnn   25980
nnnnnnnnnn nnnnnnnnnn nnnnnnnnnn nnnnnnnnnn nnnnnnnnnn nnnnnnnnnn   26040
nnnnnnnnnn nnnnnnnnnn nnnnnnnnnn nnnnnnnnnn nnnnnnnnnn nnnnnnnnnn   26100
nnnnnnnnnn nnnnnnnnnn nnnnnnnnnn nnnnnnnnnn nnnnnnnnnn nnnnnnnnnn   26160
nnnnnnnnnn nnnnnnnnnn nnnnnnnnnn nnnnnnnnnn nnnnnnnnnn nnnnnnnnnn   26220
nnnnnnnnnn nnnnnnnnnn nnnnnnnnnn nnnnnnnnnn nnnnnnnnnn nnnnnnnnnn   26280
nnnnnnnnnn nnnnnnnnnn nnnnnnnnnn nnnnnnnnnn nnnnnnnnnn nnnnnnnnnn   26340
nnnnnnnnnn nnnnnnnnnn nnnnnnnnnn nnnnnnnnnn nnnnnnnnnn nnnnnnnnnn   26400
nnnnnnnnnn nnnnnnnnnn nnnnnnnnnn nnnnnnnnnn nnnnnnnnnn nnnnnnnnnn   26460
nnnnnnnnnn nnnnnnnnnn nnnnnnnnnn nnnnnnnnga gtctgctttt ctggggtgca   26520
ggagggttcg ccctgggtgt gtcattgtcg tcgcagtgtg tggtcctgtc aggaagtgcc   26580
ctggagcagc ctccatctct tcctctgctc agtcatattc cccagctctc ttggaatccc   26640
tggagatcag tgttcagaca ccccaaagcc gcttccgttc ttacatccct gaccctagtt   26700
gccctgggct gcctgcacct gtgttggcta aggctagctg gttcagacag gcagcactga   26760 ctagccccctc tctgtcaaac agcttcttct agcccagtgg tcaattatgg catgcccct    26820
```

-continued

```
ggatcaggcc atcggccttc ttgtggccat cttccacaag tactctggta aagagggtga    26880
caagcacacc ttgagcaaga aggagctgaa ggagctgatc cagaaggagc tcaccattgg    26940
ctctgtaagt agcccctgcc caggttcccc ctcccacctc tgtccatcgg agcgctttta    27000
ctggcattta ctcttagttc ctgatcttac ttcccttgga gcttgtatgc tcccagcctg    27060
ctgagggagg agcaggggct gagaagtaaa tcaaggtaaa tccaagctga aggcccatcc    27120
ttggtgacaa tgagcagaga cacttacatg aacaaggact tccagggaag ggtaaggaa     27180 tccagggcgc tggccaccac tgaacgtgga cgtctccttc taatgtatta gaaactgcag    27240
gatgctgaga ttgcaaggct gatggacgac ctggaccgca acaaggacca ggaagtaaac    27300
ttccaggagt atgtcgcctt cctgggggcc ttggctttga tctacaatga agctctcaaa    27360
taaaatggga aggtagagat gcccttggga ggcctatctc agccaaatcc agtggtgggt    27420
aattgtacaa taaatacttt gttttgtta catcta                                27456
```

<210> SEQ ID NO 5
<211> LENGTH: 41
<212> TYPE: DNA
<213> ORGANISM: Cricetulus griseus
<220> FEATURE:
<223> OTHER INFORMATION: Targeted integration site ZFN 7

<400> SEQUENCE: 5
tttgcttact gcccaggttc tgagggacca cctggggcta g                          41

<210> SEQ ID NO 6
<211> LENGTH: 42
<212> TYPE: DNA
<213> ORGANISM: Cricetulus griseus
<220> FEATURE:
<223> OTHER INFORMATION: Targeted integration site ZFN 8

<400> SEQUENCE: 6
cagttccctc ttctgcaata ttctctagct ttagatgcag aa                         42

<210> SEQ ID NO 7
<211> LENGTH: 42
<212> TYPE: DNA
<213> ORGANISM: Cricetulus griseus
<220> FEATURE:
<223> OTHER INFORMATION: Targeted integration site ZFN 9

<400> SEQUENCE: 7
agcaactgct gtcgctcaga gcttgggagg gggtggatgg ac                         42

<210> SEQ ID NO 8
<211> LENGTH: 42
<212> TYPE: DNA
<213> ORGANISM: Cricetulus griseus
<220> FEATURE:
<223> OTHER INFORMATION: Targeted integration site ZFN 10

<400> SEQUENCE: 8
ccgcgcccaa tgctgggagg gggaagaacg ggccagagcc tg                         42

<210> SEQ ID NO 9
<211> LENGTH: 43
<212> TYPE: DNA
<213> ORGANISM: Cricetulus griseus
<220> FEATURE:
<223> OTHER INFORMATION: Targeted integration site ZFN 11

<400> SEQUENCE: 9

```
ctgggctgcc tgcacctgtg ttggctaagg ctagctggtt cag                   43

<210> SEQ ID NO 10
<211> LENGTH: 42
<212> TYPE: DNA
<213> ORGANISM: Cricetulus griseus
<220> FEATURE:
<223> OTHER INFORMATION: Targeted integration site ZFN 12

<400> SEQUENCE: 10
agcagcatct gtttccataa agtggtcagg ccccaggtgg gg                    42

<210> SEQ ID NO 11
<211> LENGTH: 43
<212> TYPE: DNA
<213> ORGANISM: Cricetulus griseus
<220> FEATURE:
<223> OTHER INFORMATION: Targeted integration site ZFN 13

<400> SEQUENCE: 11
cacaaactga ccctatgaaa gtgttcagta attcagtgcc gag                   43

<210> SEQ ID NO 12
<211> LENGTH: 42
<212> TYPE: DNA
<213> ORGANISM: Cricetulus griseus
<220> FEATURE:
<223> OTHER INFORMATION: Targeted integration site ZFN 14

<400> SEQUENCE: 12
ggcttctact gctccagctg agcctgccct gcagtgggga gg                    42

<210> SEQ ID NO 13
<211> LENGTH: 57
<212> TYPE: DNA
<213> ORGANISM: Cricetulus griseus
<220> FEATURE:
<223> OTHER INFORMATION: landing pad_upstream

<400> SEQUENCE: 13
aacagcctta ttcaggtata attcacacgc cacaaactga ccctatgaaa gtgttca    57

<210> SEQ ID NO 14
<211> LENGTH: 58
<212> TYPE: DNA
<213> ORGANISM: Cricetulus griseus
<220> FEATURE:
<223> OTHER INFORMATION: landing_pad downstream

<400> SEQUENCE: 14
tgaaagtgtt cagtaattca gtgccgagta tgatgtatca cacctgtgac cctggcac   58
```